(12) United States Patent
Gruskin et al.

(10) Patent No.: US 7,968,089 B2
(45) Date of Patent: Jun. 28, 2011

(54) PROTEOGLYCAN DEGRADING MUTANTS FOR THE TREATMENT OF CNS

(75) Inventors: Elliott A. Gruskin, Killingworth, CT (US); Anthony O. Caggiano, Larchmont, NY (US); Gargi Roy, Danbury, CT (US); Rohini D'Souza, Croton on Hudson, NY (US)

(73) Assignee: Acorda Therapeutics, Inc., Hawthorne, NY (US)

( * ) Notice: Subject to any disclaimer, the term of this patent is extended or adjusted under 35 U.S.C. 154(b) by 248 days.

(21) Appl. No.: 12/167,573

(22) Filed: Jul. 3, 2008

(65) Prior Publication Data
US 2009/0041728 A1    Feb. 12, 2009

Related U.S. Application Data

(63) Continuation of application No. 10/848,561, filed on May 17, 2004, now Pat. No. 7,429,375.

(60) Provisional application No. 60/471,239, filed on May 16, 2003, provisional application No. 60/471,300, filed on May 16, 2003, provisional application No. 60/474,372, filed on May 29, 2003, provisional application No. 60/471,240, filed on May 16, 2003.

(51) Int. Cl.
*A61K 38/51* (2006.01)
*C12N 15/60* (2006.01)
*C12N 9/88* (2006.01)

(52) U.S. Cl. .................. 424/94.5; 435/232; 536/23.2

(58) Field of Classification Search .................. None
See application file for complete search history.

(56) References Cited

U.S. PATENT DOCUMENTS

| | | | |
|---|---|---|---|
| 5,498,536 A | 3/1996 | Khandke | |
| 5,578,480 A | 11/1996 | Khandke | |
| 6,007,810 A | 12/1999 | Ishikawa et al. | |
| 7,008,783 B1 | 3/2006 | Sato et al. | |
| 2005/0233419 A1 | 10/2005 | Pojasek et al. | |
| 2006/0078959 A1 | 4/2006 | Prabhakar et al. | |
| 2006/0233782 A1 | 10/2006 | Gruskin et al. | |
| 2007/0104703 A1 | 5/2007 | Caggiano et al. | |

FOREIGN PATENT DOCUMENTS

| WO | WO 94/25567 A1 | 11/1994 |
|---|---|---|
| WO | WO 00/62067 A1 | 10/2000 |
| WO | 02/08285 A2 | 1/2002 |
| WO | 02/065136 A2 | 8/2002 |
| WO | 03/022882 A2 | 3/2003 |
| WO | 03/031578 A2 | 4/2003 |
| WO | WO 03/074080 A1 | 9/2003 |
| WO | WO 03/100031 A2 | 12/2003 |
| WO | WO 03/102160 A2 | 12/2003 |
| WO | 2004/103299 A2 | 12/2004 |
| WO | 2004/110359 A2 | 12/2004 |
| WO | WO 2004/110360 A2 | 12/2004 |
| WO | 2005/087920 A2 | 9/2005 |
| WO | 2005/112986 A2 | 12/2005 |
| WO | 2007/038548 A2 | 4/2007 |

OTHER PUBLICATIONS

Sato et al., Subunit Structure of Chondroitinase ABC from Proteus vulgaris, 1986, Agric. Biol. Chem. 50(4):1057-1059.
Fethiere et al., Crystal Structure of Chondroitin AC Lyase, a Representative of a family of Glycosaminoglycan Degrading Enzymes, 1999, J. Mol. Biol. 288:635-647.
Pojasek et al., Recombinant Expression, Purification, and Kinetic Characterization of Chondroitinase AC and Chondroitinase B from Flavobacterium heparinum, 2001, Biochem. Biophys. Res. Commun. 286:343-351.
Huang et al., Crystal Structure of Chondroitinase B from Flavobacterium heparinum and its Complex with a Disaccharide Product at 1.7 Å Resolution, 1999, J. Mol. Biol. 294:1257-1269.
Miura et al,, Analysis of Glycosaminoglycan-Degrading Enzymes by Substrate Gel Electrophoresis (Zymography), 1995, Anal. Biochem. 225:333-340.
Saito et al., Enzymatic Methods for the Determination of Small Quantities of Isomeric Chondroitin Sulfates, 1968, J. Biol. Chem. 243(7):1536-1542.
Sato et al., Cloning and expression in *Escherichia coli* of the gene encoding the Proteus vulgaris chondroitin ABC-lyase, 1994, Appl. Microbiol. Biotechnol. 41:39-46.
Frankel et al., Tat Protein from Human Immunodeficiency Virus Forms a Metal-Linked Dimer, 1988, Science 240:70-73.
Zuo et al., Regeneration of Axons After Nerve Transection Repair is Enhanced by Degradation of Chondroitin Sulfate Proteoglycan, 2002, Exp. Neurology 176:221-228.
Yamagata et al., Purification and Properties of Bacterial Chondroitinases and Chondrosulfatases, 1968, J. Biol. Chem. 243(7):1523-1535.
Bradbury et al., Chondroitinase ABC Promotes Functional Recovery After Spinal Cord Injury, Apr. 11, 2002, Nature 416:636-640.
Huang et al., Active Site of Chondroitin AC Lyase Revealed by the Structure of Enzyme-Oligosaccharide Complexes and Mutagenesis, Jan. 1, 2001, Biochemistry, 40(8):2359-2372.
Pojasek et al., Biochemical Characterization of the Chondroitinase B Active Site, Aug. 23, 2002, J. Biol. Chem., 277(34):31179-31186.
Roy et al., Generation of Substantially Smaller Deletion Mutants of Chondroitinase AC and B Those are Biologically Active, Society for Neuroscience Abstract Viewer and Itinerary Planner, 33rd Annual Meeting of the Society of Neuroscience, New Orleans, LA, Nov. 8-12, 2003, Database Biosis, (Abstract).
Accession P59807, Aug. 15, 2003 *UniProtKB/Swiss-Prot*.
Banker et al. "Modern Pharmaceutics" 1979, *Marcel Dekker, Inc.* (TOC).
Banker et al. "Modern Pharmaceutics" 4th Ed., 2002, *Informa Healthcare*, New York (TOC).
Ben-Bassat et al. "Processing of the Initiation Methionine from Proteins: Properties of the *Escherichia coli* Methionine Aminopeptidase and Its Gene Structure" 1987, *J. Bacteriol.* 169(2):751-757.
Blight et al. "Animal models of spinal cord injury" 2002, *Top Spinal Cord Inj. Rehabi.* 6(2):1-13.
Broach et al. "Experimental Manipulation of Gene Expression" M. Inouye ed., *Academic Press, New York*, pp. 83-117.

(Continued)

*Primary Examiner* — Rebecca E. Prouty
(74) *Attorney, Agent, or Firm* — Pepper Hamilton LLP

(57) ABSTRACT

The present disclosure relates to the preparation and deletion mutants of chondroitinase proteins and their use in methods for promoting the diffusion of therapeutic composition into tissues and their use for neurological functional recovery after central nervous system ("CNS") injury or disease.

34 Claims, 7 Drawing Sheets

OTHER PUBLICATIONS

Caggiano et al. "Chondroitinase ABCI Improves Locomotion and Bladder Function following Contusion Injury of the Rat Spinal Cord" 2005, *J. Neurotrauma* 22(2):226-239.

Fawcett et al. "The glial scar and central nervous system repair" 1999, *Brain Res. Bull.* 49(6):377-391.

Goodman et al. "The Pharmacological Basis of Therapeutics" 10th ed., 2001, *McGraw Hill, New York* (TOC).

Goodman et al. "The Pharmacological Basis of Therapeutics" 6th ed. 1980, *MacMillan Pub., New York* (TOC).

Hamai et al. "Two Distinct Chondroitin Sulfate ABC Lyases" 1997, *J. Biol. Chem.* 272(14):9123-9130.

Hirschberg et al. "Inflammation after axonal injury has conflicting consequences for recovery of function: rescue of spared axons is impaired but regeneration is supported" 1994, *J. Neuroimmunol.* 50(1):9-16(ABSTRACT).

Hoffman et al. "Chondroitin Sulfates" 1958, *Federation Proc.* 17:1078-1082.

Hou et al. "Endotoxin Removal by Anion-Exchange Polymeric Matrix" 1990, *Biotech. Appl. Biochem.* 12:315-324.

Huang et al. "Crystal Structure of Proteus vulgaris Chondroitin Sulfate ABC Lyase I at 1.9 A Resolution" 2003, *J. Mol. Biol.* 328:623-634.

Korn "The Degradation of Heparin by Bacterial Enzymes" 1957, *J. Biol. Chem.* 226:841-844.

Krekoski et al. "Axonal Regeneration into Acellular Nerve Grafts is Enhanced by Degradation of Chondroitin Sulfate Proteoglycan" 2001, *J. Neurosci.* 15:21(16):6206-6213.

Kwon et al. "Animal Models Used in Spinal Cord Regeneration Research" 2002, *Spine* 27(14):1504-1510.

Martinez et al. "Purification and Properties of the Enzyme Chondroitinase" 1959, *J. Biol. Chem.* 234(9):2236-2239.

Michelacci et al. "Chondroitinase C from Flavobacterium haparinum" 1976, *J. Biol. Chem.* 251(4):1154-1158.

Michelacci et al. "Isolation and characterization of an induced Chondroitinase ABC" 1987, *Biochem. Biophys. Acta* 923:291-301.

Michelacci et al., A Comparative Study Between a Chondroitinase B and a Chondroitinase AC from Flavobacterium heparinum, 1975, *Biochem. J.* 151:121-129.

Miller et al. "N-terminal methionine-specific peptidase in *Salmonella typhimurium*" 1987, *PNAS* 84:2718-2722.

Prabhakar et al. "Biochemical Characterization of the Chondroitinase ABC I Active Site" Aug. 23, 2005, *Biochem. J.* pp. 395-405.

Reich et al. "Small interfering RNA (siRNA) targeting VEGF effectively inhibits ocular neovascularization in a mouse model" 2003, *Molecular Vision* 9:210-216.

Sambrook et al. "Molecular Cloning" 2nd ed., 1989, *Cold Spring Harbor Laboratory Press*, Ch. 16 and 17.

Zuo et al. "Degradation of Chondroitin Sulfate Proteoglycan Enhances the Neurite-Promoting Potential of Spinal Cord Tissue" 1998, *Exp. Neurol.* 154(2):654-662.

(A) Anti-His-tag Western blot (top) and Zymogram (bottom) demonstrating Chondroitinase B deletion NΔ120 CΔ120 mutant expression and activity ← Anti-His-tag immunoblot ← zymography (B) Anti-His-tag Western blot (top) and Zymogram (bottom) demonstrating Chondroitinase AC deletion NΔ50 CΔ275 mutant expression and activity ← Anti-His-tag immunoblot ← zymography (A)

(B)

SEQUENCE LISTING

```
<160> NUMBER OF SEQ ID NOS: 50

<210> SEQ ID NO 1
<211> LENGTH: 997
<212> TYPE: PRT
<213> ORGANISM: Artificial
<220> FEATURE:
<223> OTHER INFORMATION: Synthetic polypeptide, chondoritinase ABC I
      protein

<400> SEQUENCE: 1

Ala Thr Ser Asn Pro Ala Phe Asp Pro Lys Asn Leu Met Gln Ser Glu
1               5                   10                  15

Ile Tyr His Phe Ala Gln Asn Asn Pro Leu Ala Asp Phe Ser Ser Asp
            20                  25                  30

Lys Asn Ser Ile Leu Thr Leu Ser Asp Lys Arg Ser Ile Met Gly Asn
        35                  40                  45

Gln Ser Leu Leu Trp Lys Trp Lys Gly Gly Ser Ser Phe Thr Leu His
    50                  55                  60

Lys Lys Leu Ile Val Pro Thr Asp Lys Glu Ala Ser Lys Ala Trp Gly
65                  70                  75                  80

Arg Ser Ser Thr Pro Val Phe Ser Phe Trp Leu Tyr Asn Glu Lys Pro
                85                  90                  95

Ile Asp Gly Tyr Leu Thr Ile Asp Phe Gly Glu Lys Leu Ile Ser Thr
            100                 105                 110

Ser Glu Ala Gln Ala Gly Phe Lys Val Lys Leu Asp Phe Thr Gly Trp
        115                 120                 125

Arg Thr Val Gly Val Ser Leu Asn Asn Asp Leu Glu Asn Arg Glu Met
    130                 135                 140

Thr Leu Asn Ala Thr Asn Thr Ser Ser Asp Gly Thr Gln Asp Ser Ile
145                 150                 155                 160

Gly Arg Ser Leu Gly Ala Lys Val Asp Ser Ile Arg Phe Lys Ala Pro
                165                 170                 175

Ser Asn Val Ser Gln Gly Glu Ile Tyr Ile Asp Arg Ile Met Phe Ser
            180                 185                 190

Val Asp Asp Ala Arg Tyr Gln Trp Ser Asp Tyr Gln Val Lys Thr Arg
        195                 200                 205

Leu Ser Glu Pro Glu Ile Gln Phe His Asn Val Lys Pro Gln Leu Pro
    210                 215                 220

Val Thr Pro Glu Asn Leu Ala Ala Ile Asp Leu Ile Arg Gln Arg Leu
225                 230                 235                 240

Ile Asn Glu Phe Val Gly Gly Lys Glu Thr Asn Leu Ala Leu Glu
                245                 250                 255

Glu Asn Ile Ser Lys Leu Lys Ser Asp Phe Asp Ala Leu Asn Thr His
            260                 265                 270

Thr Leu Ala Asn Gly Gly Thr Gln Gly Arg His Leu Ile Thr Asp Lys
        275                 280                 285

Gln Ile Ile Ile Tyr Gln Pro Glu Asn Leu Asn Ser Gln Asp Lys Gln
    290                 295                 300
```

```
Leu Phe Asp Asn Tyr Val Ile Leu Gly Asn Tyr Thr Thr Leu Met Phe
305                 310                 315                 320

Asn Ile Ser Arg Ala Tyr Val Leu Glu Lys Asp Pro Thr Gln Lys Ala
                325                 330                 335

Gln Leu Lys Gln Met Tyr Leu Leu Met Thr Lys His Leu Leu Asp Gln
            340                 345                 350

Gly Phe Val Lys Gly Ser Ala Leu Val Thr Thr His His Trp Gly Tyr
        355                 360                 365

Ser Ser Arg Trp Trp Tyr Ile Ser Thr Leu Leu Met Ser Asp Ala Leu
    370                 375                 380

Lys Glu Ala Asn Leu Gln Thr Gln Val Tyr Asp Ser Leu Leu Trp Tyr
385                 390                 395                 400

Ser Arg Glu Phe Lys Ser Ser Phe Asp Met Lys Val Ser Ala Asp Ser
                405                 410                 415

Ser Asp Leu Asp Tyr Phe Asn Thr Leu Ser Arg Gln His Leu Ala Leu
            420                 425                 430

Leu Leu Leu Glu Pro Asp Asp Gln Lys Arg Ile Asn Leu Val Asn Thr
        435                 440                 445

Phe Ser His Tyr Ile Thr Gly Ala Leu Thr Gln Val Pro Pro Gly Gly
    450                 455                 460

Lys Asp Gly Leu Arg Pro Asp Gly Thr Ala Trp Arg His Glu Gly Asn
465                 470                 475                 480

Tyr Pro Gly Tyr Ser Phe Pro Ala Phe Lys Asn Ala Ser Gln Leu Ile
                485                 490                 495

Tyr Leu Leu Arg Asp Thr Pro Phe Ser Val Gly Glu Ser Gly Trp Asn
            500                 505                 510

Asn Leu Lys Lys Ala Met Val Ser Ala Trp Ile Tyr Ser Asn Pro Glu
        515                 520                 525

Val Gly Leu Pro Leu Ala Gly Arg His Pro Phe Asn Ser Pro Ser Leu
    530                 535                 540

Lys Ser Val Ala Gln Gly Tyr Tyr Trp Leu Ala Met Ser Ala Lys Ser
545                 550                 555                 560

Ser Pro Asp Lys Thr Leu Ala Ser Ile Tyr Leu Ala Ile Ser Asp Lys
                565                 570                 575

Thr Gln Asn Glu Ser Thr Ala Ile Phe Gly Glu Thr Ile Thr Pro Ala
            580                 585                 590

Ser Leu Pro Gln Gly Phe Tyr Ala Phe Asn Gly Gly Ala Phe Gly Ile
        595                 600                 605

His Arg Trp Gln Asp Lys Met Val Thr Leu Lys Ala Tyr Asn Thr Asn
    610                 615                 620

Val Trp Ser Ser Glu Ile Tyr Asn Lys Asp Asn Arg Tyr Gly Arg Tyr
625                 630                 635                 640

Gln Ser His Gly Val Ala Gln Ile Val Ser Asn Gly Ser Gln Leu Ser
                645                 650                 655

Gln Gly Tyr Gln Gln Glu Gly Trp Asp Trp Asn Arg Met Glu Gly Ala
            660                 665                 670

Thr Thr Ile His Leu Pro Leu Lys Asp Leu Asp Ser Pro Lys Pro His
        675                 680                 685

Thr Leu Met Gln Arg Gly Glu Arg Gly Phe Ser Gly Thr Ser Ser Leu
    690                 695                 700

Glu Gly Gln Tyr Gly Met Met Ala Phe Asn Leu Ile Tyr Pro Ala Asn
705                 710                 715                 720

Leu Glu Arg Phe Asp Pro Asn Phe Thr Ala Lys Lys Ser Val Leu Ala
```

```
                       725                 730                 735
Ala Asp Asn His Leu Ile Phe Ile Gly Ser Asn Ile Asn Ser Ser Asp
            740                 745                 750

Lys Asn Lys Asn Val Glu Thr Thr Leu Phe Gln His Ala Ile Thr Pro
        755                 760                 765

Thr Leu Asn Thr Leu Trp Ile Asn Gly Gln Lys Ile Glu Asn Met Pro
    770                 775                 780

Tyr Gln Thr Thr Leu Gln Gln Gly Asp Trp Leu Ile Asp Ser Asn Gly
785                 790                 795                 800

Asn Gly Tyr Leu Ile Thr Gln Ala Glu Lys Val Asn Val Ser Arg Gln
                805                 810                 815

His Gln Val Ser Ala Glu Asn Lys Asn Arg Gln Pro Thr Glu Gly Asn
            820                 825                 830

Phe Ser Ser Ala Trp Ile Asp His Ser Thr Arg Pro Lys Asp Ala Ser
        835                 840                 845

Tyr Glu Tyr Met Val Phe Leu Asp Ala Thr Pro Glu Lys Met Gly Glu
    850                 855                 860

Met Ala Gln Lys Phe Arg Glu Asn Asn Gly Leu Tyr Gln Val Leu Arg
865                 870                 875                 880

Lys Asp Lys Asp Val His Ile Ile Leu Asp Lys Leu Ser Asn Val Thr
                885                 890                 895

Gly Tyr Ala Phe Tyr Gln Pro Ala Ser Ile Glu Asp Lys Trp Ile Lys
            900                 905                 910

Lys Val Asn Lys Pro Ala Ile Val Met Thr His Arg Gln Lys Asp Thr
        915                 920                 925

Leu Ile Val Ser Ala Val Thr Pro Asp Leu Asn Met Thr Arg Gln Lys
    930                 935                 940

Ala Ala Thr Pro Val Thr Ile Asn Val Thr Ile Asn Gly Lys Trp Gln
945                 950                 955                 960

Ser Ala Asp Lys Asn Ser Glu Val Lys Tyr Gln Val Ser Gly Asp Asn
                965                 970                 975

Thr Glu Leu Thr Phe Thr Ser Tyr Phe Gly Ile Pro Gln Glu Ile Lys
            980                 985                 990

Leu Ser Pro Leu Pro
        995

<210> SEQ ID NO 2
<211> LENGTH: 977
<212> TYPE: PRT
<213> ORGANISM: Artificial
<220> FEATURE:
<223> OTHER INFORMATION: Synthetic polypeptide, N(delta)20 ABC I

<400> SEQUENCE: 2

Ala Gln Asn Asn Pro Leu Ala Asp Phe Ser Ser Asp Lys Asn Ser Ile
1               5                   10                  15

Leu Thr Leu Ser Asp Lys Arg Ser Ile Met Gly Asn Gln Ser Leu Leu
            20                  25                  30

Trp Lys Trp Lys Gly Gly Ser Ser Phe Thr Leu His Lys Lys Leu Ile
        35                  40                  45

Val Pro Thr Asp Lys Glu Ala Ser Lys Ala Trp Gly Arg Ser Ser Thr
    50                  55                  60

Pro Val Phe Ser Phe Trp Leu Tyr Asn Glu Lys Pro Ile Asp Gly Tyr
65                  70                  75                  80

Leu Thr Ile Asp Phe Gly Glu Lys Leu Ile Ser Thr Ser Glu Ala Gln
                85                  90                  95
```

```
Ala Gly Phe Lys Val Lys Leu Asp Phe Thr Gly Trp Arg Thr Val Gly
            100                 105                 110
Val Ser Leu Asn Asn Asp Leu Glu Asn Arg Glu Met Thr Leu Asn Ala
        115                 120                 125
Thr Asn Thr Ser Ser Asp Gly Thr Gln Asp Ser Ile Gly Arg Ser Leu
    130                 135                 140
Gly Ala Lys Val Asp Ser Ile Arg Phe Lys Ala Pro Ser Asn Val Ser
145                 150                 155                 160
Gln Gly Glu Ile Tyr Ile Asp Arg Ile Met Phe Ser Val Asp Asp Ala
                165                 170                 175
Arg Tyr Gln Trp Ser Asp Tyr Gln Val Lys Thr Arg Leu Ser Glu Pro
            180                 185                 190
Glu Ile Gln Phe His Asn Val Lys Pro Gln Leu Pro Val Thr Pro Glu
        195                 200                 205
Asn Leu Ala Ala Ile Asp Leu Ile Arg Gln Arg Leu Ile Asn Glu Phe
    210                 215                 220
Val Gly Gly Glu Lys Glu Thr Asn Leu Ala Leu Glu Glu Asn Ile Ser
225                 230                 235                 240
Lys Leu Lys Ser Asp Phe Asp Ala Leu Asn Thr His Thr Leu Ala Asn
                245                 250                 255
Gly Gly Thr Gln Gly Arg His Leu Ile Thr Asp Lys Gln Ile Ile
            260                 265                 270
Tyr Gln Pro Glu Asn Leu Asn Ser Gln Asp Lys Gln Leu Phe Asp Asn
        275                 280                 285
Tyr Val Ile Leu Gly Asn Tyr Thr Thr Leu Met Phe Asn Ile Ser Arg
    290                 295                 300
Ala Tyr Val Leu Glu Lys Asp Pro Thr Gln Lys Ala Gln Leu Lys Gln
305                 310                 315                 320
Met Tyr Leu Leu Met Thr Lys His Leu Leu Asp Gln Gly Phe Val Lys
                325                 330                 335
Gly Ser Ala Leu Val Thr Thr His His Trp Gly Tyr Ser Ser Arg Trp
            340                 345                 350
Trp Tyr Ile Ser Thr Leu Leu Met Ser Asp Ala Leu Lys Glu Ala Asn
        355                 360                 365
Leu Gln Thr Gln Val Tyr Asp Ser Leu Leu Trp Tyr Ser Arg Glu Phe
    370                 375                 380
Lys Ser Ser Phe Asp Met Lys Val Ser Ala Asp Ser Ser Asp Leu Asp
385                 390                 395                 400
Tyr Phe Asn Thr Leu Ser Arg Gln His Leu Ala Leu Leu Leu Glu
                405                 410                 415
Pro Asp Asp Gln Lys Arg Ile Asn Leu Val Asn Thr Phe Ser His Tyr
            420                 425                 430
Ile Thr Gly Ala Leu Thr Gln Val Pro Pro Gly Gly Lys Asp Gly Leu
        435                 440                 445
Arg Pro Asp Gly Thr Ala Trp Arg His Glu Gly Asn Tyr Pro Gly Tyr
    450                 455                 460
Ser Phe Pro Ala Phe Lys Asn Ala Ser Gln Leu Ile Tyr Leu Leu Arg
465                 470                 475                 480
Asp Thr Pro Phe Ser Val Gly Glu Ser Gly Trp Asn Asn Leu Lys Lys
                485                 490                 495
Ala Met Val Ser Ala Trp Ile Tyr Ser Asn Pro Glu Val Gly Leu Pro
            500                 505                 510
Leu Ala Gly Arg His Pro Phe Asn Ser Pro Ser Leu Lys Ser Val Ala
```

```
                515                 520                 525
Gln Gly Tyr Tyr Trp Leu Ala Met Ser Ala Lys Ser Pro Asp Lys
    530                 535                 540

Thr Leu Ala Ser Ile Tyr Leu Ala Ile Ser Asp Lys Thr Gln Asn Glu
545                 550                 555                 560

Ser Thr Ala Ile Phe Gly Glu Thr Ile Thr Pro Ala Ser Leu Pro Gln
                565                 570                 575

Gly Phe Tyr Ala Phe Asn Gly Ala Phe Gly Ile His Arg Trp Gln
                580                 585                 590

Asp Lys Met Val Thr Leu Lys Ala Tyr Asn Thr Asn Val Trp Ser Ser
            595                 600                 605

Glu Ile Tyr Asn Lys Asp Asn Arg Tyr Gly Arg Tyr Gln Ser His Gly
            610                 615                 620

Val Ala Gln Ile Val Ser Asn Gly Ser Gln Leu Ser Gln Gly Tyr Gln
625                 630                 635                 640

Gln Glu Gly Trp Asp Trp Asn Arg Met Glu Gly Ala Thr Thr Ile His
                645                 650                 655

Leu Pro Leu Lys Asp Leu Asp Ser Pro Lys Pro His Thr Leu Met Gln
            660                 665                 670

Arg Gly Glu Arg Gly Phe Ser Gly Thr Ser Ser Leu Glu Gly Gln Tyr
    675                 680                 685

Gly Met Met Ala Phe Asn Leu Ile Tyr Pro Ala Asn Leu Glu Arg Phe
690                 695                 700

Asp Pro Asn Phe Thr Ala Lys Lys Ser Val Leu Ala Ala Asp Asn His
705                 710                 715                 720

Leu Ile Phe Ile Gly Ser Asn Ile Asn Ser Ser Asp Lys Asn Lys Asn
                725                 730                 735

Val Glu Thr Thr Leu Phe Gln His Ala Ile Thr Pro Thr Leu Asn Thr
            740                 745                 750

Leu Trp Ile Asn Gly Gln Lys Ile Glu Asn Met Pro Tyr Gln Thr Thr
            755                 760                 765

Leu Gln Gln Gly Asp Trp Leu Ile Asp Ser Asn Gly Asn Gly Tyr Leu
    770                 775                 780

Ile Thr Gln Ala Glu Lys Val Asn Val Ser Arg Gln His Gln Val Ser
785                 790                 795                 800

Ala Glu Asn Lys Asn Arg Gln Pro Thr Glu Gly Asn Phe Ser Ser Ala
                805                 810                 815

Trp Ile Asp His Ser Thr Arg Pro Lys Asp Ala Ser Tyr Glu Tyr Met
            820                 825                 830

Val Phe Leu Asp Ala Thr Pro Glu Lys Met Gly Glu Met Ala Gln Lys
            835                 840                 845

Phe Arg Glu Asn Asn Gly Leu Tyr Gln Val Leu Arg Lys Asp Lys Asp
    850                 855                 860

Val His Ile Ile Leu Asp Lys Leu Ser Asn Val Thr Gly Tyr Ala Phe
865                 870                 875                 880

Tyr Gln Pro Ala Ser Ile Glu Asp Lys Trp Ile Lys Lys Val Asn Lys
                885                 890                 895

Pro Ala Ile Val Met Thr His Arg Gln Lys Asp Thr Leu Ile Val Ser
            900                 905                 910

Ala Val Thr Pro Asp Leu Asn Met Thr Arg Gln Lys Ala Ala Thr Pro
    915                 920                 925

Val Thr Ile Asn Val Thr Ile Asn Gly Lys Trp Gln Ser Ala Asp Lys
    930                 935                 940
```

-continued

```
Asn Ser Glu Val Lys Tyr Gln Val Ser Gly Asp Asn Thr Glu Leu Thr
945                 950                 955                 960

Phe Thr Ser Tyr Phe Gly Ile Pro Gln Glu Ile Lys Leu Ser Pro Leu
            965                 970                 975

Pro

<210> SEQ ID NO 3
<211> LENGTH: 937
<212> TYPE: PRT
<213> ORGANISM: Artificial
<220> FEATURE:
<223> OTHER INFORMATION: Synthetic polypeptide, N(delta)60 ABC I

<400> SEQUENCE: 3

Phe Thr Leu His Lys Lys Leu Ile Val Pro Thr Asp Lys Glu Ala Ser
1               5                   10                  15

Lys Ala Trp Gly Arg Ser Ser Thr Pro Val Phe Ser Phe Trp Leu Tyr
            20                  25                  30

Asn Glu Lys Pro Ile Asp Gly Tyr Leu Thr Ile Asp Phe Gly Glu Lys
            35                  40                  45

Leu Ile Ser Thr Ser Glu Ala Gln Ala Gly Phe Lys Val Lys Leu Asp
50                  55                  60

Phe Thr Gly Trp Arg Thr Val Gly Val Ser Leu Asn Asn Asp Leu Glu
65                  70                  75                  80

Asn Arg Glu Met Thr Leu Asn Ala Thr Asn Thr Ser Ser Asp Gly Thr
            85                  90                  95

Gln Asp Ser Ile Gly Arg Ser Leu Gly Ala Lys Val Asp Ser Ile Arg
            100                 105                 110

Phe Lys Ala Pro Ser Asn Val Ser Gln Gly Glu Ile Tyr Ile Asp Arg
            115                 120                 125

Ile Met Phe Ser Val Asp Asp Ala Arg Tyr Gln Trp Ser Asp Tyr Gln
130                 135                 140

Val Lys Thr Arg Leu Ser Glu Pro Glu Ile Gln Phe His Asn Val Lys
145                 150                 155                 160

Pro Gln Leu Pro Val Thr Pro Glu Asn Leu Ala Ala Ile Asp Leu Ile
            165                 170                 175

Arg Gln Arg Leu Ile Asn Glu Phe Val Gly Gly Glu Lys Glu Thr Asn
            180                 185                 190

Leu Ala Leu Glu Glu Asn Ile Ser Lys Leu Lys Ser Asp Phe Asp Ala
            195                 200                 205

Leu Asn Thr His Thr Leu Ala Asn Gly Gly Thr Gln Gly Arg His Leu
210                 215                 220

Ile Thr Asp Lys Gln Ile Ile Tyr Gln Pro Glu Asn Leu Asn Ser
225                 230                 235                 240

Gln Asp Lys Gln Leu Phe Asp Asn Tyr Val Ile Leu Gly Asn Tyr Thr
            245                 250                 255

Thr Leu Met Phe Asn Ile Ser Arg Ala Tyr Val Leu Glu Lys Asp Pro
            260                 265                 270

Thr Gln Lys Ala Gln Leu Lys Gln Met Tyr Leu Leu Met Thr Lys His
            275                 280                 285

Leu Leu Asp Gln Gly Phe Val Lys Gly Ser Ala Leu Val Thr Thr His
            290                 295                 300

His Trp Gly Tyr Ser Ser Arg Trp Trp Tyr Ile Ser Thr Leu Leu Met
305                 310                 315                 320

Ser Asp Ala Leu Lys Glu Ala Asn Leu Gln Thr Gln Val Tyr Asp Ser
            325                 330                 335
```

```
Leu Leu Trp Tyr Ser Arg Glu Phe Lys Ser Ser Phe Asp Met Lys Val
                340                 345                 350

Ser Ala Asp Ser Ser Asp Leu Asp Tyr Phe Asn Thr Leu Ser Arg Gln
        355                 360                 365

His Leu Ala Leu Leu Leu Glu Pro Asp Asp Gln Lys Arg Ile Asn
    370                 375                 380

Leu Val Asn Thr Phe Ser His Tyr Ile Thr Gly Ala Leu Thr Gln Val
385                 390                 395                 400

Pro Pro Gly Gly Lys Asp Gly Leu Arg Pro Asp Gly Thr Ala Trp Arg
                405                 410                 415

His Glu Gly Asn Tyr Pro Gly Tyr Ser Phe Pro Ala Phe Lys Asn Ala
            420                 425                 430

Ser Gln Leu Ile Tyr Leu Leu Arg Asp Thr Pro Phe Ser Val Gly Glu
        435                 440                 445

Ser Gly Trp Asn Asn Leu Lys Lys Ala Met Val Ser Ala Trp Ile Tyr
    450                 455                 460

Ser Asn Pro Glu Val Gly Leu Pro Leu Ala Gly Arg His Pro Phe Asn
465                 470                 475                 480

Ser Pro Ser Leu Lys Ser Val Ala Gln Gly Tyr Tyr Trp Leu Ala Met
                485                 490                 495

Ser Ala Lys Ser Ser Pro Asp Lys Thr Leu Ala Ser Ile Tyr Leu Ala
            500                 505                 510

Ile Ser Asp Lys Thr Gln Asn Glu Ser Thr Ala Ile Phe Gly Glu Thr
        515                 520                 525

Ile Thr Pro Ala Ser Leu Pro Gln Gly Phe Tyr Ala Phe Asn Gly Gly
    530                 535                 540

Ala Phe Gly Ile His Arg Trp Gln Asp Lys Met Val Thr Leu Lys Ala
545                 550                 555                 560

Tyr Asn Thr Asn Val Trp Ser Ser Glu Ile Tyr Asn Lys Asp Asn Arg
                565                 570                 575

Tyr Gly Arg Tyr Gln Ser His Gly Val Ala Gln Ile Val Ser Asn Gly
            580                 585                 590

Ser Gln Leu Ser Gln Gly Tyr Gln Gln Glu Gly Trp Asp Trp Asn Arg
        595                 600                 605

Met Glu Gly Ala Thr Thr Ile His Leu Pro Leu Lys Asp Leu Asp Ser
    610                 615                 620

Pro Lys Pro His Thr Leu Met Gln Arg Gly Glu Arg Gly Phe Ser Gly
625                 630                 635                 640

Thr Ser Ser Leu Glu Gly Gln Tyr Gly Met Met Ala Phe Asn Leu Ile
                645                 650                 655

Tyr Pro Ala Asn Leu Glu Arg Phe Asp Pro Asn Phe Thr Ala Lys Lys
            660                 665                 670

Ser Val Leu Ala Ala Asp Asn His Leu Ile Phe Ile Gly Ser Asn Ile
        675                 680                 685

Asn Ser Ser Asp Lys Asn Lys Asn Val Glu Thr Thr Leu Phe Gln His
    690                 695                 700

Ala Ile Thr Pro Thr Leu Asn Thr Leu Trp Ile Asn Gly Gln Lys Ile
705                 710                 715                 720

Glu Asn Met Pro Tyr Gln Thr Thr Leu Gln Gln Gly Asp Trp Leu Ile
                725                 730                 735

Asp Ser Asn Gly Asn Gly Tyr Leu Ile Thr Gln Ala Glu Lys Val Asn
            740                 745                 750

Val Ser Arg Gln His Gln Val Ser Ala Glu Asn Lys Asn Arg Gln Pro
```

-continued

```
                755                 760                 765
Thr Glu Gly Asn Phe Ser Ser Ala Trp Ile Asp His Ser Thr Arg Pro
    770                 775                 780

Lys Asp Ala Ser Tyr Glu Tyr Met Val Phe Leu Asp Ala Thr Pro Glu
785                 790                 795                 800

Lys Met Gly Glu Met Ala Gln Lys Phe Arg Glu Asn Asn Gly Leu Tyr
                805                 810                 815

Gln Val Leu Arg Lys Asp Lys Val His Ile Ile Leu Asp Lys Leu
            820                 825                 830

Ser Asn Val Thr Gly Tyr Ala Phe Tyr Gln Pro Ala Ser Ile Glu Asp
            835                 840                 845

Lys Trp Ile Lys Lys Val Asn Lys Pro Ala Ile Val Met Thr His Arg
    850                 855                 860

Gln Lys Asp Thr Leu Ile Val Ser Ala Val Thr Pro Asp Leu Asn Met
865                 870                 875                 880

Thr Arg Gln Lys Ala Ala Thr Pro Val Thr Ile Asn Val Thr Ile Asn
                885                 890                 895

Gly Lys Trp Gln Ser Ala Asp Lys Asn Ser Glu Val Lys Tyr Gln Val
            900                 905                 910

Ser Gly Asp Asn Thr Glu Leu Thr Phe Thr Ser Tyr Phe Gly Ile Pro
            915                 920                 925

Gln Glu Ile Lys Leu Ser Pro Leu Pro
    930                 935

<210> SEQ ID NO 4
<211> LENGTH: 858
<212> TYPE: PRT
<213> ORGANISM: Artificial
<220> FEATURE:
<223> OTHER INFORMATION: Synthetic polypeptide, N(delta)60  C(delta)80
      ABC I (F[sub]85 - A[sub]942)

<400> SEQUENCE: 4

Phe Thr Leu His Lys Lys Leu Ile Val Pro Thr Asp Lys Glu Ala Ser
1               5                   10                  15

Lys Ala Trp Gly Arg Ser Ser Thr Pro Val Phe Ser Phe Trp Leu Tyr
                20                  25                  30

Asn Glu Lys Pro Ile Asp Gly Tyr Leu Thr Ile Asp Phe Gly Glu Lys
            35                  40                  45

Leu Ile Ser Thr Ser Glu Ala Gln Ala Gly Phe Lys Val Lys Leu Asp
    50                  55                  60

Phe Thr Gly Trp Arg Thr Val Gly Val Ser Leu Asn Asn Asp Leu Glu
65                  70                  75                  80

Asn Arg Glu Met Thr Leu Asn Ala Thr Asn Thr Ser Ser Asp Gly Thr
                85                  90                  95

Gln Asp Ser Ile Gly Arg Ser Leu Gly Ala Lys Val Asp Ser Ile Arg
            100                 105                 110

Phe Lys Ala Pro Ser Asn Val Ser Gln Gly Glu Ile Tyr Ile Asp Arg
    115                 120                 125

Ile Met Phe Ser Val Asp Asp Ala Arg Tyr Gln Trp Ser Asp Tyr Gln
130                 135                 140

Val Lys Thr Arg Leu Ser Glu Pro Glu Ile Gln Phe His Asn Val Lys
145                 150                 155                 160

Pro Gln Leu Pro Val Thr Pro Glu Asn Leu Ala Ala Ile Asp Leu Ile
                165                 170                 175

Arg Gln Arg Leu Ile Asn Glu Phe Val Gly Gly Glu Lys Glu Thr Asn
```

```
                    180                 185                 190
Leu Ala Leu Glu Glu Asn Ile Ser Lys Leu Lys Ser Asp Phe Asp Ala
            195                 200                 205
Leu Asn Thr His Thr Leu Ala Asn Gly Gly Thr Gln Gly Arg His Leu
            210                 215                 220
Ile Thr Asp Lys Gln Ile Ile Tyr Gln Pro Glu Asn Leu Asn Ser
225                 230                 235                 240
Gln Asp Lys Gln Leu Phe Asp Asn Tyr Val Ile Leu Gly Asn Tyr Thr
                245                 250                 255
Thr Leu Met Phe Asn Ile Ser Arg Ala Tyr Val Leu Glu Lys Asp Pro
            260                 265                 270
Thr Gln Lys Ala Gln Leu Lys Gln Met Tyr Leu Leu Met Thr Lys His
            275                 280                 285
Leu Leu Asp Gln Gly Phe Val Lys Gly Ser Ala Leu Val Thr Thr His
            290                 295                 300
His Trp Gly Tyr Ser Ser Arg Trp Trp Tyr Ile Ser Thr Leu Leu Met
305                 310                 315                 320
Ser Asp Ala Leu Lys Glu Ala Asn Leu Gln Thr Gln Val Tyr Asp Ser
                325                 330                 335
Leu Leu Trp Tyr Ser Arg Glu Phe Lys Ser Ser Phe Asp Met Lys Val
                340                 345                 350
Ser Ala Asp Ser Ser Asp Leu Asp Tyr Phe Asn Thr Leu Ser Arg Gln
                355                 360                 365
His Leu Ala Leu Leu Leu Glu Pro Asp Asp Gln Lys Arg Ile Asn
            370                 375                 380
Leu Val Asn Thr Phe Ser His Tyr Ile Thr Gly Ala Leu Thr Gln Val
385                 390                 395                 400
Pro Pro Gly Gly Lys Asp Gly Leu Arg Pro Asp Gly Thr Ala Trp Arg
                405                 410                 415
His Glu Gly Asn Tyr Pro Gly Tyr Ser Phe Pro Ala Phe Lys Asn Ala
                420                 425                 430
Ser Gln Leu Ile Tyr Leu Leu Arg Asp Thr Pro Phe Ser Val Gly Glu
            435                 440                 445
Ser Gly Trp Asn Asn Leu Lys Lys Ala Met Val Ser Ala Trp Ile Tyr
450                 455                 460
Ser Asn Pro Glu Val Gly Leu Pro Leu Ala Gly Arg His Pro Phe Asn
465                 470                 475                 480
Ser Pro Ser Leu Lys Ser Val Ala Gln Gly Tyr Tyr Trp Leu Ala Met
                485                 490                 495
Ser Ala Lys Ser Ser Pro Asp Lys Thr Leu Ala Ser Ile Tyr Leu Ala
            500                 505                 510
Ile Ser Asp Lys Thr Gln Asn Glu Ser Thr Ala Ile Phe Gly Glu Thr
        515                 520                 525
Ile Thr Pro Ala Ser Leu Pro Gln Gly Phe Tyr Ala Phe Asn Gly Gly
        530                 535                 540
Ala Phe Gly Ile His Arg Trp Gln Asp Lys Met Val Thr Leu Lys Ala
545                 550                 555                 560
Tyr Asn Thr Asn Val Trp Ser Ser Glu Ile Tyr Asn Lys Asp Asn Arg
                565                 570                 575
Tyr Gly Arg Tyr Gln Ser His Gly Val Ala Gln Ile Val Ser Asn Gly
            580                 585                 590
Ser Gln Leu Ser Gln Gly Tyr Gln Gln Glu Gly Trp Asp Trp Asn Arg
            595                 600                 605
```

```
Met Glu Gly Ala Thr Thr Ile His Leu Pro Leu Lys Asp Leu Asp Ser
610                 615                 620

Pro Lys Pro His Thr Leu Met Gln Arg Gly Glu Arg Gly Phe Ser Gly
625                 630                 635                 640

Thr Ser Ser Leu Glu Gly Gln Tyr Gly Met Met Ala Phe Asn Leu Ile
                645                 650                 655

Tyr Pro Ala Asn Leu Glu Arg Phe Asp Pro Asn Phe Thr Ala Lys Lys
                660                 665                 670

Ser Val Leu Ala Ala Asp Asn His Leu Ile Phe Ile Gly Ser Asn Ile
            675                 680                 685

Asn Ser Ser Asp Lys Asn Lys Asn Val Glu Thr Thr Leu Phe Gln His
690                 695                 700

Ala Ile Thr Pro Thr Leu Asn Thr Leu Trp Ile Asn Gly Gln Lys Ile
705                 710                 715                 720

Glu Asn Met Pro Tyr Gln Thr Thr Leu Gln Gln Gly Asp Trp Leu Ile
                725                 730                 735

Asp Ser Asn Gly Asn Gly Tyr Leu Ile Thr Gln Ala Glu Lys Val Asn
                740                 745                 750

Val Ser Arg Gln His Gln Val Ser Ala Glu Asn Lys Asn Arg Gln Pro
            755                 760                 765

Thr Glu Gly Asn Phe Ser Ser Ala Trp Ile Asp His Ser Thr Arg Pro
770                 775                 780

Lys Asp Ala Ser Tyr Glu Tyr Met Val Phe Leu Asp Ala Thr Pro Glu
785                 790                 795                 800

Lys Met Gly Glu Met Ala Gln Lys Phe Arg Glu Asn Asn Gly Leu Tyr
                805                 810                 815

Gln Val Leu Arg Lys Asp Lys Asp Val His Ile Ile Leu Asp Lys Leu
                820                 825                 830

Ser Asn Val Thr Gly Tyr Ala Phe Tyr Gln Pro Ala Ser Ile Glu Asp
            835                 840                 845

Lys Trp Ile Lys Lys Val Asn Lys Pro Ala
850                 855

<210> SEQ ID NO 5
<211> LENGTH: 700
<212> TYPE: PRT
<213> ORGANISM: Pedobacter Heparinus

<400> SEQUENCE: 5

Met Lys Lys Leu Phe Val Thr Cys Ile Val Phe Phe Ser Ile Leu Ser
1               5                   10                  15

Pro Ala Leu Leu Ile Ala Gln Gln Thr Gly Thr Ala Glu Leu Ile Met
                20                  25                  30

Lys Arg Val Met Leu Asp Leu Lys Lys Pro Leu Arg Asn Met Asp Lys
            35                  40                  45

Val Ala Glu Lys Asn Leu Asn Thr Leu Gln Pro Asp Gly Ser Trp Lys
50                  55                  60

Asp Val Pro Tyr Lys Asp Ala Met Thr Asn Trp Leu Pro Asn Asn
65                  70                  75                  80

His Leu Leu Gln Leu Glu Thr Ile Ile Gln Ala Tyr Ile Glu Lys Asp
                85                  90                  95

Ser His Tyr Tyr Gly Asp Asp Lys Val Phe Asp Gln Ile Ser Lys Ala
                100                 105                 110

Phe Lys Tyr Trp Tyr Asp Ser Asp Pro Lys Ser Arg Asn Trp Trp His
            115                 120                 125
```

```
Asn Glu Ile Ala Thr Pro Gln Ala Leu Gly Glu Met Leu Ile Leu Met
    130                 135                 140
Arg Tyr Gly Lys Lys Pro Leu Asp Glu Ala Leu Val His Lys Leu Thr
145                 150                 155                 160
Glu Arg Met Lys Arg Gly Glu Pro Glu Lys Lys Thr Gly Ala Asn Lys
                165                 170                 175
Thr Asp Ile Ala Leu His Tyr Phe Tyr Arg Ala Leu Leu Thr Ser Asp
            180                 185                 190
Glu Ala Leu Leu Ser Phe Ala Val Lys Glu Leu Phe Tyr Pro Val Gln
        195                 200                 205
Phe Val His Tyr Glu Gly Leu Gln Tyr Asp Tyr Ser Tyr Leu Gln
    210                 215                 220
His Gly Pro Gln Leu Gln Ile Ser Ser Tyr Gly Ala Val Phe Ile Thr
225                 230                 235                 240
Gly Val Leu Lys Leu Ala Asn Tyr Val Arg Asp Thr Pro Tyr Ala Leu
                245                 250                 255
Ser Thr Glu Lys Leu Ala Ile Phe Ser Lys Tyr Tyr Arg Asp Ser Tyr
            260                 265                 270
Leu Lys Ala Ile Arg Gly Ser Tyr Met Asp Phe Asn Val Glu Gly Arg
        275                 280                 285
Gly Val Ser Arg Pro Asp Ile Leu Asn Lys Lys Ala Glu Lys Lys Arg
    290                 295                 300
Leu Leu Val Ala Lys Met Ile Asp Leu Lys His Thr Glu Glu Trp Ala
305                 310                 315                 320
Asp Ala Ile Ala Arg Thr Asp Ser Thr Val Ala Gly Tyr Lys Ile
                325                 330                 335
Glu Pro Tyr His His Gln Phe Trp Asn Gly Asp Tyr Val Gln His Leu
            340                 345                 350
Arg Pro Ala Tyr Ser Phe Asn Val Arg Met Val Ser Lys Arg Thr Arg
        355                 360                 365
Arg Ser Glu Ser Gly Asn Lys Glu Asn Leu Leu Gly Arg Tyr Leu Ser
    370                 375                 380
Asp Gly Ala Thr Asn Ile Gln Leu Arg Gly Pro Glu Tyr Tyr Asn Ile
385                 390                 395                 400
Met Pro Val Trp Glu Trp Asp Lys Ile Pro Gly Ile Thr Ser Arg Asp
                405                 410                 415
Tyr Leu Thr Asp Arg Pro Leu Thr Lys Leu Trp Gly Glu Gln Gly Ser
            420                 425                 430
Asn Asp Phe Ala Gly Gly Val Ser Asp Gly Val Tyr Gly Ala Ser Ala
        435                 440                 445
Tyr Ala Leu Asp Tyr Asp Ser Leu Gln Ala Lys Ala Trp Phe Phe
    450                 455                 460
Phe Asp Lys Glu Ile Val Cys Leu Gly Ala Gly Ile Asn Ser Asn Ala
465                 470                 475                 480
Pro Glu Asn Ile Thr Thr Leu Asn Gln Ser Trp Leu Asn Gly Pro
                485                 490                 495
Val Ile Ser Thr Ala Gly Lys Thr Gly Arg Gly Lys Ile Thr Thr Phe
            500                 505                 510
Lys Ala Gln Gly Gln Phe Trp Leu Leu His Asp Ala Ile Gly Tyr Tyr
        515                 520                 525
Phe Pro Glu Gly Ala Asn Leu Ser Leu Ser Thr Gln Ser Gln Lys Gly
    530                 535                 540
Asn Trp Phe His Ile Asn Asn Ser His Ser Lys Asp Glu Val Ser Gly
545                 550                 555                 560
```

```
Asp Val Phe Lys Leu Trp Ile Asn His Gly Ala Arg Pro Glu Asn Ala
            565                 570                 575

Gln Tyr Ala Tyr Ile Val Leu Pro Gly Ile Asn Lys Pro Glu Glu Ile
            580                 585                 590

Lys Lys Tyr Asn Gly Thr Ala Pro Lys Val Leu Ala Asn Thr Asn Gln
            595                 600                 605

Leu Gln Ala Val Tyr His Gln Gln Leu Asp Met Val Gln Ala Ile Phe
            610                 615                 620

Tyr Thr Ala Gly Lys Leu Ser Val Ala Gly Ile Glu Ile Glu Thr Asp
625                 630                 635                 640

Lys Pro Cys Ala Val Leu Ile Lys His Ile Asn Gly Lys Gln Val Ile
            645                 650                 655

Trp Ala Ala Asp Pro Leu Gln Lys Glu Lys Thr Ala Val Leu Ser Ile
            660                 665                 670

Arg Asp Leu Lys Thr Gly Lys Thr Asn Arg Val Lys Ile Asp Phe Pro
            675                 680                 685

Gln Gln Glu Phe Ala Gly Ala Thr Val Glu Leu Lys
            690                 695                 700

<210> SEQ ID NO 6
<211> LENGTH: 478
<212> TYPE: PRT
<213> ORGANISM: Artificial
<220> FEATURE:
<223> OTHER INFORMATION: Synthetic polypeptide, C(delta)200
      chondroitinase AC (Q[sub]23 - T[sub]500)

<400> SEQUENCE: 6

Gln Gln Thr Gly Thr Ala Glu Leu Ile Met Lys Arg Val Met Leu Asp
1               5                   10                  15

Leu Lys Lys Pro Leu Arg Asn Met Asp Lys Val Ala Glu Lys Asn Leu
            20                  25                  30

Asn Thr Leu Gln Pro Asp Gly Ser Trp Lys Asp Val Pro Tyr Lys Asp
        35                  40                  45

Asp Ala Met Thr Asn Trp Leu Pro Asn Asn His Leu Leu Gln Leu Glu
50                  55                  60

Thr Ile Ile Gln Ala Tyr Ile Glu Lys Asp Ser His Tyr Tyr Gly Asp
65                  70                  75                  80

Asp Lys Val Phe Asp Gln Ile Ser Lys Ala Phe Lys Tyr Trp Tyr Asp
            85                  90                  95

Ser Asp Pro Lys Ser Arg Asn Trp Trp His Asn Glu Ile Ala Thr Pro
            100                 105                 110

Gln Ala Leu Gly Glu Met Leu Ile Leu Met Arg Tyr Gly Lys Lys Pro
        115                 120                 125

Leu Asp Glu Ala Leu Val His Lys Leu Thr Glu Arg Met Lys Arg Gly
130                 135                 140

Glu Pro Glu Lys Lys Thr Gly Ala Asn Lys Thr Asp Ile Ala Leu His
145                 150                 155                 160

Tyr Phe Tyr Arg Ala Leu Leu Thr Ser Asp Glu Ala Leu Leu Ser Phe
            165                 170                 175

Ala Val Lys Glu Leu Phe Tyr Pro Val Gln Phe Val His Tyr Glu Glu
            180                 185                 190

Gly Leu Gln Tyr Asp Tyr Ser Tyr Leu Gln His Gly Pro Gln Leu Gln
        195                 200                 205

Ile Ser Ser Tyr Gly Ala Val Phe Ile Thr Gly Val Leu Lys Leu Ala
        210                 215                 220
```

```
Asn Tyr Val Arg Asp Thr Pro Tyr Ala Leu Ser Thr Glu Lys Leu Ala
225                 230                 235                 240

Ile Phe Ser Lys Tyr Tyr Arg Asp Ser Tyr Leu Lys Ala Ile Arg Gly
            245                 250                 255

Ser Tyr Met Asp Phe Asn Val Glu Gly Arg Gly Val Ser Arg Pro Asp
        260                 265                 270

Ile Leu Asn Lys Lys Ala Glu Lys Arg Leu Leu Val Ala Lys Met
    275                 280                 285

Ile Asp Leu Lys His Thr Glu Glu Trp Ala Asp Ala Ile Ala Arg Thr
290                 295                 300

Asp Ser Thr Val Ala Ala Gly Tyr Lys Ile Glu Pro Tyr His His Gln
305                 310                 315                 320

Phe Trp Asn Gly Asp Tyr Val Gln His Leu Arg Pro Ala Tyr Ser Phe
            325                 330                 335

Asn Val Arg Met Val Ser Lys Arg Thr Arg Arg Ser Glu Ser Gly Asn
        340                 345                 350

Lys Glu Asn Leu Leu Gly Arg Tyr Leu Ser Asp Gly Ala Thr Asn Ile
    355                 360                 365

Gln Leu Arg Gly Pro Glu Tyr Tyr Asn Ile Met Pro Val Trp Glu Trp
370                 375                 380

Asp Lys Ile Pro Gly Ile Thr Ser Arg Asp Tyr Leu Thr Asp Arg Pro
385                 390                 395                 400

Leu Thr Lys Leu Trp Gly Glu Gln Gly Ser Asn Asp Phe Ala Gly Gly
            405                 410                 415

Val Ser Asp Gly Val Tyr Gly Ala Ser Ala Tyr Ala Leu Asp Tyr Asp
        420                 425                 430

Ser Leu Gln Ala Lys Lys Ala Trp Phe Phe Phe Asp Lys Glu Ile Val
    435                 440                 445

Cys Leu Gly Ala Gly Ile Asn Ser Asn Ala Pro Glu Asn Ile Thr Thr
450                 455                 460

Thr Leu Asn Gln Ser Trp Leu Asn Gly Pro Val Ile Ser Thr
465                 470                 475

<210> SEQ ID NO 7
<211> LENGTH: 458
<212> TYPE: PRT
<213> ORGANISM: Artificial
<220> FEATURE:
<223> OTHER INFORMATION: Synthetic polypeptide, C(delta)220
      chondroitinase AC (Q[sub]23 - A[sub]480)

<400> SEQUENCE: 7

Gln Gln Thr Gly Thr Ala Glu Leu Ile Met Lys Arg Val Met Leu Asp
1               5                   10                  15

Leu Lys Lys Pro Leu Arg Asn Met Asp Lys Val Ala Glu Lys Asn Leu
            20                  25                  30

Asn Thr Leu Gln Pro Asp Gly Ser Trp Lys Asp Val Pro Tyr Lys Asp
        35                  40                  45

Asp Ala Met Thr Asn Trp Leu Pro Asn Asn His Leu Leu Gln Leu Glu
    50                  55                  60

Thr Ile Ile Gln Ala Tyr Ile Glu Lys Asp Ser His Tyr Tyr Gly Asp
65                  70                  75                  80

Asp Lys Val Phe Asp Gln Ile Ser Lys Ala Phe Lys Tyr Trp Tyr Asp
            85                  90                  95

Ser Asp Pro Lys Ser Arg Asn Trp Trp His Asn Glu Ile Ala Thr Pro
        100                 105                 110
```

Gln Ala Leu Gly Glu Met Leu Ile Leu Met Arg Tyr Gly Lys Lys Pro
            115                 120                 125

Leu Asp Glu Ala Leu Val His Lys Leu Thr Glu Arg Met Lys Arg Gly
130                 135                 140

Glu Pro Glu Lys Lys Thr Gly Ala Asn Lys Thr Asp Ile Ala Leu His
145                 150                 155                 160

Tyr Phe Tyr Arg Ala Leu Leu Thr Ser Asp Glu Ala Leu Leu Ser Phe
                165                 170                 175

Ala Val Lys Glu Leu Phe Tyr Pro Val Gln Phe Val His Tyr Glu Glu
            180                 185                 190

Gly Leu Gln Tyr Asp Tyr Ser Tyr Leu Gln His Gly Pro Gln Leu Gln
        195                 200                 205

Ile Ser Ser Tyr Gly Ala Val Phe Ile Thr Gly Val Leu Lys Leu Ala
    210                 215                 220

Asn Tyr Val Arg Asp Thr Pro Tyr Ala Leu Ser Thr Glu Lys Leu Ala
225                 230                 235                 240

Ile Phe Ser Lys Tyr Tyr Arg Asp Ser Tyr Leu Lys Ala Ile Arg Gly
                245                 250                 255

Ser Tyr Met Asp Phe Asn Val Glu Gly Arg Gly Val Ser Arg Pro Asp
            260                 265                 270

Ile Leu Asn Lys Lys Ala Glu Lys Arg Leu Leu Val Ala Lys Met
        275                 280                 285

Ile Asp Leu Lys His Thr Glu Glu Trp Ala Asp Ala Ile Ala Arg Thr
    290                 295                 300

Asp Ser Thr Val Ala Ala Gly Tyr Lys Ile Glu Pro Tyr His His Gln
305                 310                 315                 320

Phe Trp Asn Gly Asp Tyr Val Gln His Leu Arg Pro Ala Tyr Ser Phe
                325                 330                 335

Asn Val Arg Met Val Ser Lys Arg Thr Arg Ser Glu Ser Gly Asn
            340                 345                 350

Lys Glu Asn Leu Leu Gly Arg Tyr Leu Ser Asp Gly Ala Thr Asn Ile
        355                 360                 365

Gln Leu Arg Gly Pro Glu Tyr Tyr Asn Ile Met Pro Val Trp Glu Trp
    370                 375                 380

Asp Lys Ile Pro Gly Ile Thr Ser Arg Asp Tyr Leu Thr Asp Arg Pro
385                 390                 395                 400

Leu Thr Lys Leu Trp Gly Glu Gln Gly Ser Asn Asp Phe Ala Gly Gly
                405                 410                 415

Val Ser Asp Gly Val Tyr Gly Ala Ser Ala Tyr Ala Leu Asp Tyr Asp
            420                 425                 430

Ser Leu Gln Ala Lys Lys Ala Trp Phe Phe Asp Lys Glu Ile Val
        435                 440                 445

Cys Leu Gly Ala Gly Ile Asn Ser Asn Ala
    450                 455

<210> SEQ ID NO 8
<211> LENGTH: 458
<212> TYPE: PRT
<213> ORGANISM: Artificial
<220> FEATURE:
<223> OTHER INFORMATION: Synthetic polypeptide, N(delta)20 C(delta)200
      chondroitinase AC (L[sub]43 - T[sub]500)

<400> SEQUENCE: 8

Leu Arg Asn Met Asp Lys Val Ala Glu Lys Asn Leu Asn Thr Leu Gln
1               5                   10                  15

```
Pro Asp Gly Ser Trp Lys Asp Val Pro Tyr Lys Asp Asp Ala Met Thr
            20                  25                  30
Asn Trp Leu Pro Asn Asn His Leu Leu Gln Leu Glu Thr Ile Ile Gln
        35                  40                  45
Ala Tyr Ile Glu Lys Asp Ser His Tyr Tyr Gly Asp Asp Lys Val Phe
50                  55                  60
Asp Gln Ile Ser Lys Ala Phe Lys Tyr Trp Tyr Asp Ser Asp Pro Lys
65                  70                  75                  80
Ser Arg Asn Trp Trp His Asn Glu Ile Ala Thr Pro Gln Ala Leu Gly
                85                  90                  95
Glu Met Leu Ile Leu Met Arg Tyr Gly Lys Lys Pro Leu Asp Glu Ala
            100                 105                 110
Leu Val His Lys Leu Thr Glu Arg Met Lys Arg Gly Glu Pro Glu Lys
        115                 120                 125
Lys Thr Gly Ala Asn Lys Thr Asp Ile Ala Leu His Tyr Phe Tyr Arg
130                 135                 140
Ala Leu Leu Thr Ser Asp Glu Ala Leu Leu Ser Phe Ala Val Lys Glu
145                 150                 155                 160
Leu Phe Tyr Pro Val Gln Phe Val His Glu Glu Gly Leu Gln Tyr
                165                 170                 175
Asp Tyr Ser Tyr Leu Gln His Gly Pro Gln Leu Gln Ile Ser Ser Tyr
            180                 185                 190
Gly Ala Val Phe Ile Thr Gly Val Leu Lys Leu Ala Asn Tyr Val Arg
        195                 200                 205
Asp Thr Pro Tyr Ala Leu Ser Thr Glu Lys Leu Ala Ile Phe Ser Lys
210                 215                 220
Tyr Tyr Arg Asp Ser Tyr Leu Lys Ala Ile Arg Gly Ser Tyr Met Asp
225                 230                 235                 240
Phe Asn Val Glu Gly Arg Gly Val Ser Arg Pro Asp Ile Leu Asn Lys
                245                 250                 255
Lys Ala Glu Lys Lys Arg Leu Leu Val Ala Lys Met Ile Asp Leu Lys
            260                 265                 270
His Thr Glu Glu Trp Ala Asp Ala Ile Ala Arg Thr Asp Ser Thr Val
        275                 280                 285
Ala Ala Gly Tyr Lys Ile Glu Pro Tyr His His Gln Phe Trp Asn Gly
290                 295                 300
Asp Tyr Val Gln His Leu Arg Pro Ala Tyr Ser Phe Asn Val Arg Met
305                 310                 315                 320
Val Ser Lys Arg Thr Arg Arg Ser Glu Ser Gly Asn Lys Glu Asn Leu
                325                 330                 335
Leu Gly Arg Tyr Leu Ser Asp Gly Ala Thr Asn Ile Gln Leu Arg Gly
            340                 345                 350
Pro Glu Tyr Tyr Asn Ile Met Pro Val Trp Glu Trp Asp Lys Ile Pro
        355                 360                 365
Gly Ile Thr Ser Arg Asp Tyr Leu Thr Asp Arg Pro Leu Thr Lys Leu
370                 375                 380
Trp Gly Glu Gln Gly Ser Asn Asp Phe Ala Gly Gly Val Ser Asp Gly
385                 390                 395                 400
Val Tyr Gly Ala Ser Ala Tyr Ala Leu Asp Tyr Asp Ser Leu Gln Ala
                405                 410                 415
Lys Lys Ala Trp Phe Phe Phe Asp Lys Glu Ile Val Cys Leu Gly Ala
            420                 425                 430
Gly Ile Asn Ser Asn Ala Pro Glu Asn Ile Thr Thr Thr Leu Asn Gln
```

```
                435                 440                 445
Ser Trp Leu Asn Gly Pro Val Ile Ser Thr
    450                 455

<210> SEQ ID NO 9
<211> LENGTH: 427
<212> TYPE: PRT
<213> ORGANISM: Artificial
<220> FEATURE:
<223> OTHER INFORMATION: Synthetic polypeptide, N(delta)500 C(delta)200
      of chondroitinase AC (T[sub]74 - T[sub]500)

<400> SEQUENCE: 9

Thr Asn Trp Leu Pro Asn Asn His Leu Leu Gln Leu Glu Thr Ile Ile
1               5                   10                  15

Gln Ala Tyr Ile Glu Lys Asp Ser His Tyr Tyr Gly Asp Asp Lys Val
            20                  25                  30

Phe Asp Gln Ile Ser Lys Ala Phe Lys Tyr Trp Tyr Asp Ser Asp Pro
        35                  40                  45

Lys Ser Arg Asn Trp Trp His Asn Glu Ile Ala Thr Pro Gln Ala Leu
    50                  55                  60

Gly Glu Met Leu Ile Leu Met Arg Tyr Gly Lys Pro Leu Asp Glu
65                  70                  75                  80

Ala Leu Val His Lys Leu Thr Glu Arg Met Lys Arg Gly Glu Pro Glu
                85                  90                  95

Lys Lys Thr Gly Ala Asn Lys Thr Asp Ile Ala Leu His Tyr Phe Tyr
            100                 105                 110

Arg Ala Leu Leu Thr Ser Asp Glu Ala Leu Leu Ser Phe Ala Val Lys
        115                 120                 125

Glu Leu Phe Tyr Pro Val Gln Phe Val His Tyr Glu Glu Gly Leu Gln
    130                 135                 140

Tyr Asp Tyr Ser Tyr Leu Gln His Gly Pro Gln Leu Gln Ile Ser Ser
145                 150                 155                 160

Tyr Gly Ala Val Phe Ile Thr Gly Val Leu Lys Leu Ala Asn Tyr Val
                165                 170                 175

Arg Asp Thr Pro Tyr Ala Leu Ser Thr Glu Lys Leu Ala Ile Phe Ser
            180                 185                 190

Lys Tyr Tyr Arg Asp Ser Tyr Leu Lys Ala Ile Arg Gly Ser Tyr Met
        195                 200                 205

Asp Phe Asn Val Glu Gly Arg Gly Val Ser Arg Pro Asp Ile Leu Asn
    210                 215                 220

Lys Lys Ala Glu Lys Lys Arg Leu Leu Val Ala Lys Met Ile Asp Leu
225                 230                 235                 240

Lys His Thr Glu Glu Trp Ala Asp Ala Ile Ala Arg Thr Asp Ser Thr
                245                 250                 255

Val Ala Ala Gly Tyr Lys Ile Glu Pro Tyr His His Gln Phe Trp Asn
            260                 265                 270

Gly Asp Tyr Val Gln His Leu Arg Pro Ala Tyr Ser Phe Asn Val Arg
        275                 280                 285

Met Val Ser Lys Arg Thr Arg Arg Ser Glu Ser Gly Asn Lys Glu Asn
    290                 295                 300

Leu Leu Gly Arg Tyr Leu Ser Asp Gly Ala Thr Asn Ile Gln Leu Arg
305                 310                 315                 320

Gly Pro Glu Tyr Tyr Asn Ile Met Pro Val Trp Glu Trp Asp Lys Ile
                325                 330                 335

Pro Gly Ile Thr Ser Arg Asp Tyr Leu Thr Asp Arg Pro Leu Thr Lys
```

```
                        340                 345                 350
Leu Trp Gly Glu Gln Gly Ser Asn Asp Phe Ala Gly Gly Val Ser Asp
                355                 360                 365

Gly Val Tyr Gly Ala Ser Ala Tyr Ala Leu Asp Tyr Asp Ser Leu Gln
            370                 375                 380

Ala Lys Lys Ala Trp Phe Phe Asp Lys Glu Ile Val Cys Leu Gly
385                 390                 395                 400

Ala Gly Ile Asn Ser Asn Ala Pro Glu Asn Ile Thr Thr Thr Leu Asn
                405                 410                 415

Gln Ser Trp Leu Asn Gly Pro Val Ile Ser Thr
            420                 425

<210> SEQ ID NO 10
<211> LENGTH: 378
<212> TYPE: PRT
<213> ORGANISM: Artificial
<220> FEATURE:
<223> OTHER INFORMATION: Synthetic polypeptide, N(delta)100 C(delta)200
      of chondroitinase AC (S[sub]123 - T[sub]500)

<400> SEQUENCE: 10

Ser Arg Asn Trp Trp His Asn Glu Ile Ala Thr Pro Gln Ala Leu Gly
1               5                   10                  15

Glu Met Leu Ile Leu Met Arg Tyr Gly Lys Lys Pro Leu Asp Glu Ala
            20                  25                  30

Leu Val His Lys Leu Thr Glu Arg Met Lys Arg Gly Glu Pro Glu Lys
        35                  40                  45

Lys Thr Gly Ala Asn Lys Thr Asp Ile Ala Leu His Tyr Phe Tyr Arg
    50                  55                  60

Ala Leu Leu Thr Ser Asp Glu Ala Leu Leu Ser Phe Ala Val Lys Glu
65                  70                  75                  80

Leu Phe Tyr Pro Val Gln Phe Val His Tyr Glu Glu Gly Leu Gln Tyr
                85                  90                  95

Asp Tyr Ser Tyr Leu Gln His Gly Pro Gln Leu Gln Ile Ser Ser Tyr
            100                 105                 110

Gly Ala Val Phe Ile Thr Gly Val Leu Lys Leu Ala Asn Tyr Val Arg
        115                 120                 125

Asp Thr Pro Tyr Ala Leu Ser Thr Glu Lys Leu Ala Ile Phe Ser Lys
    130                 135                 140

Tyr Tyr Arg Asp Ser Tyr Leu Lys Ala Ile Arg Gly Ser Tyr Met Asp
145                 150                 155                 160

Phe Asn Val Glu Gly Arg Gly Val Ser Arg Pro Asp Ile Leu Asn Lys
                165                 170                 175

Lys Ala Glu Lys Lys Arg Leu Leu Val Ala Lys Met Ile Asp Leu Lys
            180                 185                 190

His Thr Glu Glu Trp Ala Asp Ala Ile Ala Arg Thr Asp Ser Thr Val
        195                 200                 205

Ala Ala Gly Tyr Lys Ile Glu Pro Tyr His His Gln Phe Trp Asn Gly
    210                 215                 220

Asp Tyr Val Gln His Leu Arg Pro Ala Tyr Ser Phe Asn Val Arg Met
225                 230                 235                 240

Val Ser Lys Arg Thr Arg Arg Ser Glu Ser Gly Asn Lys Glu Asn Leu
                245                 250                 255

Leu Gly Arg Tyr Leu Ser Asp Gly Ala Thr Asn Ile Gln Leu Arg Gly
            260                 265                 270

Pro Glu Tyr Tyr Asn Ile Met Pro Val Trp Glu Trp Asp Lys Ile Pro
```

```
                    275                 280                 285
Gly Ile Thr Ser Arg Asp Tyr Leu Thr Asp Arg Pro Leu Thr Lys Leu
            290                 295                 300
Trp Gly Glu Gln Gly Ser Asn Asp Phe Ala Gly Gly Val Ser Asp Gly
305                 310                 315                 320
Val Tyr Gly Ala Ser Ala Tyr Ala Leu Asp Tyr Asp Ser Leu Gln Ala
                325                 330                 335
Lys Lys Ala Trp Phe Phe Asp Lys Glu Ile Val Cys Leu Gly Ala
            340                 345                 350
Gly Ile Asn Ser Asn Ala Pro Glu Asn Ile Thr Thr Thr Leu Asn Gln
            355                 360                 365
Ser Trp Leu Asn Gly Pro Val Ile Ser Thr
            370                 375

<210> SEQ ID NO 11
<211> LENGTH: 353
<212> TYPE: PRT
<213> ORGANISM: Artificial
<220> FEATURE:
<223> OTHER INFORMATION: Synthetic polypeptide, N(delta)50 C(delta)275
      of chondroitinase AC (T[sub]74 - L[sub]426)

<400> SEQUENCE: 11

Thr Asn Trp Leu Pro Asn Asn His Leu Leu Gln Leu Glu Thr Ile Ile
1               5                   10                  15
Gln Ala Tyr Ile Glu Lys Asp Ser His Tyr Tyr Gly Asp Asp Lys Val
            20                  25                  30
Phe Asp Gln Ile Ser Lys Ala Phe Lys Tyr Trp Tyr Asp Ser Asp Pro
        35                  40                  45
Lys Ser Arg Asn Trp Trp His Asn Glu Ile Ala Thr Pro Gln Ala Leu
50                  55                  60
Gly Glu Met Leu Ile Leu Met Arg Tyr Gly Lys Lys Pro Leu Asp Glu
65                  70                  75                  80
Ala Leu Val His Lys Leu Thr Glu Arg Met Lys Arg Gly Glu Pro Glu
                85                  90                  95
Lys Lys Thr Gly Ala Asn Lys Thr Asp Ile Ala Leu His Tyr Phe Tyr
            100                 105                 110
Arg Ala Leu Leu Thr Ser Asp Glu Ala Leu Leu Ser Phe Ala Val Lys
        115                 120                 125
Glu Leu Phe Tyr Pro Val Gln Phe Val His Tyr Glu Glu Gly Leu Gln
    130                 135                 140
Tyr Asp Tyr Ser Tyr Leu Gln His Gly Pro Gln Leu Gln Ile Ser Ser
145                 150                 155                 160
Tyr Gly Ala Val Phe Ile Thr Gly Val Leu Lys Leu Ala Asn Tyr Val
                165                 170                 175
Arg Asp Thr Pro Tyr Ala Leu Ser Thr Glu Lys Leu Ala Ile Phe Ser
            180                 185                 190
Lys Tyr Tyr Arg Asp Ser Tyr Leu Lys Ala Ile Arg Gly Ser Tyr Met
        195                 200                 205
Asp Phe Asn Val Glu Gly Arg Gly Val Ser Arg Pro Asp Ile Leu Asn
    210                 215                 220
Lys Lys Ala Glu Lys Arg Leu Leu Val Ala Lys Met Ile Asp Leu
225                 230                 235                 240
Lys His Thr Glu Glu Trp Ala Asp Ala Ile Ala Arg Thr Asp Ser Thr
                245                 250                 255
Val Ala Ala Gly Tyr Lys Ile Glu Pro Tyr His His Gln Phe Trp Asn
```

```
                    260                 265                 270
Gly Asp Tyr Val Gln His Leu Arg Pro Ala Tyr Ser Phe Asn Val Arg
            275                 280                 285

Met Val Ser Lys Arg Thr Arg Arg Ser Glu Ser Gly Asn Lys Glu Asn
        290                 295                 300

Leu Leu Gly Arg Tyr Leu Ser Asp Gly Ala Thr Asn Ile Gln Leu Arg
305                 310                 315                 320

Gly Pro Glu Tyr Tyr Asn Ile Met Pro Val Trp Glu Trp Asp Lys Ile
                325                 330                 335

Pro Gly Ile Thr Ser Arg Asp Tyr Leu Thr Asp Arg Pro Leu Thr Lys
            340                 345                 350

Leu

<210> SEQ ID NO 12
<211> LENGTH: 506
<212> TYPE: PRT
<213> ORGANISM: Pedobacter Heparinus

<400> SEQUENCE: 12

Met Lys Met Leu Asn Lys Leu Ala Gly Tyr Leu Leu Pro Ile Met Val
1               5                   10                  15

Leu Leu Asn Val Ala Pro Cys Leu Gly Gln Val Val Ala Ser Asn Glu
            20                  25                  30

Thr Leu Tyr Gln Val Val Lys Glu Val Lys Pro Gly Gly Leu Val Gln
        35                  40                  45

Ile Ala Asp Gly Thr Tyr Lys Asp Val Gln Leu Ile Val Ser Asn Ser
    50                  55                  60

Gly Lys Ser Gly Leu Pro Ile Thr Ile Lys Ala Leu Asn Pro Gly Lys
65                  70                  75                  80

Val Phe Phe Thr Gly Asp Ala Lys Val Glu Leu Arg Gly Glu His Leu
                85                  90                  95

Ile Leu Glu Gly Ile Trp Phe Lys Asp Gly Asn Arg Ala Ile Gln Ala
            100                 105                 110

Trp Lys Ser His Gly Pro Gly Leu Val Ala Ile Tyr Gly Ser Tyr Asn
        115                 120                 125

Arg Ile Thr Ala Cys Val Phe Asp Cys Phe Asp Glu Ala Asn Ser Ala
    130                 135                 140

Tyr Ile Thr Thr Ser Leu Thr Glu Asp Gly Lys Val Pro Gln His Cys
145                 150                 155                 160

Arg Ile Asp His Cys Ser Phe Thr Asp Lys Ile Thr Phe Asp Gln Val
                165                 170                 175

Ile Asn Leu Asn Asn Thr Ala Arg Ala Ile Lys Asp Gly Ser Val Gly
            180                 185                 190

Gly Pro Gly Met Tyr His Arg Val Asp His Cys Phe Phe Ser Asn Pro
        195                 200                 205

Gln Lys Pro Gly Asn Ala Gly Gly Ile Arg Ile Gly Tyr Tyr Arg
    210                 215                 220

Asn Asp Ile Gly Arg Cys Leu Val Asp Ser Asn Leu Phe Met Arg Gln
225                 230                 235                 240

Asp Ser Glu Ala Glu Ile Ile Thr Ser Lys Ser Gln Glu Asn Val Tyr
                245                 250                 255

Tyr Gly Asn Thr Tyr Leu Asn Cys Gln Gly Thr Met Asn Phe Arg His
            260                 265                 270

Gly Asp His Gln Val Ala Ile Asn Asn Phe Tyr Ile Gly Asn Asp Gln
        275                 280                 285
```

```
Arg Phe Gly Tyr Gly Gly Met Phe Val Trp Gly Ser Arg His Val Ile
    290                 295                 300
Ala Cys Asn Tyr Phe Glu Leu Ser Glu Thr Ile Lys Ser Arg Gly Asn
305                 310                 315                 320
Ala Ala Leu Tyr Leu Asn Pro Gly Ala Met Ala Ser Glu His Ala Leu
                325                 330                 335
Ala Phe Asp Met Leu Ile Ala Asn Asn Ala Phe Ile Asn Val Asn Gly
            340                 345                 350
Tyr Ala Ile His Phe Asn Pro Leu Asp Glu Arg Arg Lys Glu Tyr Cys
                355                 360                 365
Ala Ala Asn Arg Leu Lys Phe Glu Thr Pro His Gln Leu Met Leu Lys
370                 375                 380
Gly Asn Leu Phe Phe Lys Asp Lys Pro Tyr Val Tyr Pro Phe Lys
385                 390                 395                 400
Asp Asp Tyr Phe Ile Ala Gly Lys Asn Ser Trp Thr Gly Asn Val Ala
                405                 410                 415
Leu Gly Val Glu Lys Gly Ile Pro Val Asn Ile Ser Ala Asn Arg Ser
                420                 425                 430
Ala Tyr Lys Pro Val Lys Ile Lys Asp Ile Gln Pro Ile Glu Gly Ile
                435                 440                 445
Ala Leu Asp Leu Asn Ala Leu Ile Ser Lys Gly Ile Thr Gly Lys Pro
450                 455                 460
Leu Ser Trp Asp Glu Val Arg Pro Tyr Trp Leu Lys Glu Met Pro Gly
465                 470                 475                 480
Thr Tyr Ala Leu Thr Ala Arg Leu Ser Ala Asp Arg Ala Ala Lys Phe
                485                 490                 495
Lys Ala Val Ile Lys Arg Asn Lys Glu His
                500                 505

<210> SEQ ID NO 13
<211> LENGTH: 401
<212> TYPE: PRT
<213> ORGANISM: Artificial
<220> FEATURE:
<223> OTHER INFORMATION: Synthetic polypeptide, N(delta)80
      chondroitinase B (G[sub]1026 - H[sub]506)

<400> SEQUENCE: 13

Gly Asn Arg Ala Ile Gln Ala Trp Lys Ser His Gly Pro Gly Leu Val
1               5                   10                  15
Ala Ile Tyr Gly Ser Tyr Asn Arg Ile Thr Ala Cys Val Phe Asp Cys
                20                  25                  30
Phe Asp Glu Ala Asn Ser Ala Tyr Ile Thr Thr Ser Leu Thr Glu Asp
            35                  40                  45
Gly Lys Val Pro Gln His Cys Arg Ile Asp His Cys Ser Phe Thr Asp
        50                  55                  60
Lys Ile Thr Phe Asp Gln Val Ile Asn Leu Asn Asn Thr Ala Arg Ala
65                  70                  75                  80
Ile Lys Asp Gly Ser Val Gly Gly Pro Gly Met Tyr His Arg Val Asp
                85                  90                  95
His Cys Phe Phe Ser Asn Pro Gln Lys Pro Gly Asn Ala Gly Gly Gly
            100                 105                 110
Ile Arg Ile Gly Tyr Tyr Arg Asn Asp Ile Gly Arg Cys Leu Val Asp
        115                 120                 125
Ser Asn Leu Phe Met Arg Gln Asp Ser Glu Ala Glu Ile Ile Thr Ser
    130                 135                 140
```

Lys Ser Gln Glu Asn Val Tyr Tyr Gly Asn Thr Tyr Leu Asn Cys Gln
145                 150                 155                 160

Gly Thr Met Asn Phe Arg His Gly Asp His Gln Val Ala Ile Asn Asn
                165                 170                 175

Phe Tyr Ile Gly Asn Asp Gln Arg Phe Gly Tyr Gly Gly Met Phe Val
            180                 185                 190

Trp Gly Ser Arg His Val Ile Ala Cys Asn Tyr Phe Glu Leu Ser Glu
        195                 200                 205

Thr Ile Lys Ser Arg Gly Asn Ala Ala Leu Tyr Leu Asn Pro Gly Ala
    210                 215                 220

Met Ala Ser Glu His Ala Leu Ala Phe Asp Met Leu Ile Ala Asn Asn
225                 230                 235                 240

Ala Phe Ile Asn Val Asn Gly Tyr Ala Ile His Phe Asn Pro Leu Asp
                245                 250                 255

Glu Arg Arg Lys Glu Tyr Cys Ala Ala Asn Arg Leu Lys Phe Glu Thr
            260                 265                 270

Pro His Gln Leu Met Leu Lys Gly Asn Leu Phe Phe Lys Asp Lys Pro
        275                 280                 285

Tyr Val Tyr Pro Phe Phe Lys Asp Asp Tyr Phe Ile Ala Gly Lys Asn
    290                 295                 300

Ser Trp Thr Gly Asn Val Ala Leu Gly Val Glu Lys Gly Ile Pro Val
305                 310                 315                 320

Asn Ile Ser Ala Asn Arg Ser Ala Tyr Lys Pro Val Lys Ile Lys Asp
                325                 330                 335

Ile Gln Pro Ile Glu Gly Ile Ala Leu Asp Leu Asn Ala Leu Ile Ser
            340                 345                 350

Lys Gly Ile Thr Gly Lys Pro Leu Ser Trp Asp Glu Val Arg Pro Tyr
        355                 360                 365

Trp Leu Lys Glu Met Pro Gly Thr Tyr Ala Leu Thr Ala Arg Leu Ser
    370                 375                 380

Ala Asp Arg Ala Ala Lys Phe Lys Ala Val Ile Lys Arg Asn Lys Glu
385                 390                 395                 400

His

<210> SEQ ID NO 14
<211> LENGTH: 361
<212> TYPE: PRT
<213> ORGANISM: Artificial
<220> FEATURE:
<223> OTHER INFORMATION: Synthetic polypeptide, N(delta)120
      chondroitinase B (I[sub]146 - H[sub]506)

<400> SEQUENCE: 14

Ile Thr Thr Ser Leu Thr Glu Asp Gly Lys Val Pro Gln His Cys Arg
1               5                   10                  15

Ile Asp His Cys Ser Phe Thr Asp Lys Ile Thr Phe Asp Gln Val Ile
                20                  25                  30

Asn Leu Asn Asn Thr Ala Arg Ala Ile Lys Asp Gly Ser Val Gly Gly
            35                  40                  45

Pro Gly Met Tyr His Arg Val Asp His Cys Phe Phe Ser Asn Pro Gln
        50                  55                  60

Lys Pro Gly Asn Ala Gly Gly Ile Arg Ile Gly Tyr Tyr Arg Asn
65                  70                  75                  80

Asp Ile Gly Arg Cys Leu Val Asp Ser Asn Leu Phe Met Arg Gln Asp
                85                  90                  95

```
Ser Glu Ala Glu Ile Ile Thr Ser Lys Ser Gln Glu Asn Val Tyr Tyr
            100                 105                 110

Gly Asn Thr Tyr Leu Asn Cys Gln Gly Thr Met Asn Phe Arg His Gly
            115                 120                 125

Asp His Gln Val Ala Ile Asn Asn Phe Tyr Ile Gly Asn Asp Gln Arg
            130                 135                 140

Phe Gly Tyr Gly Gly Met Phe Val Trp Gly Ser Arg His Val Ile Ala
145                 150                 155                 160

Cys Asn Tyr Phe Glu Leu Ser Glu Thr Ile Lys Ser Arg Gly Asn Ala
                165                 170                 175

Ala Leu Tyr Leu Asn Pro Gly Ala Met Ala Ser Glu His Ala Leu Ala
            180                 185                 190

Phe Asp Met Leu Ile Ala Asn Asn Ala Phe Ile Asn Val Asn Gly Tyr
            195                 200                 205

Ala Ile His Phe Asn Pro Leu Asp Glu Arg Arg Lys Glu Tyr Cys Ala
            210                 215                 220

Ala Asn Arg Leu Lys Phe Glu Thr Pro His Gln Leu Met Leu Lys Gly
225                 230                 235                 240

Asn Leu Phe Phe Lys Asp Lys Pro Tyr Val Tyr Pro Phe Phe Lys Asp
                245                 250                 255

Asp Tyr Phe Ile Ala Gly Lys Asn Ser Trp Thr Gly Asn Val Ala Leu
            260                 265                 270

Gly Val Glu Lys Gly Ile Pro Val Asn Ile Ser Ala Asn Arg Ser Ala
            275                 280                 285

Tyr Lys Pro Val Lys Ile Lys Asp Ile Gln Pro Ile Glu Gly Ile Ala
            290                 295                 300

Leu Asp Leu Asn Ala Leu Ile Ser Lys Gly Ile Thr Gly Lys Pro Leu
305                 310                 315                 320

Ser Trp Asp Glu Val Arg Pro Tyr Trp Leu Lys Glu Met Pro Gly Thr
                325                 330                 335

Tyr Ala Leu Thr Ala Arg Leu Ser Ala Asp Arg Ala Ala Lys Phe Lys
            340                 345                 350

Ala Val Ile Lys Arg Asn Lys Glu His
            355                 360

<210> SEQ ID NO 15
<211> LENGTH: 463
<212> TYPE: PRT
<213> ORGANISM: Artificial
<220> FEATURE:
<223> OTHER INFORMATION: Synthetic polypeptide, C(delta)19
      chondroitinase B (Q[sub]26 - L[sub]488)

<400> SEQUENCE: 15

Gln Val Val Ala Ser Asn Glu Thr Leu Tyr Gln Val Val Lys Glu Val
1               5                   10                  15

Lys Pro Gly Gly Leu Val Gln Ile Ala Asp Gly Thr Tyr Lys Asp Val
            20                  25                  30

Gln Leu Ile Val Ser Asn Ser Gly Lys Ser Gly Leu Pro Ile Thr Ile
            35                  40                  45

Lys Ala Leu Asn Pro Gly Lys Val Phe Phe Thr Gly Asp Ala Lys Val
            50                  55                  60

Glu Leu Arg Gly Glu His Leu Ile Leu Glu Gly Ile Trp Phe Lys Asp
65                  70                  75                  80

Gly Asn Arg Ala Ile Gln Ala Trp Lys Ser His Gly Pro Gly Leu Val
                85                  90                  95
```

```
Ala Ile Tyr Gly Ser Tyr Asn Arg Ile Thr Ala Cys Val Phe Asp Cys
            100                 105                 110

Phe Asp Glu Ala Asn Ser Ala Tyr Ile Thr Thr Ser Leu Thr Glu Asp
        115                 120                 125

Gly Lys Val Pro Gln His Cys Arg Ile Asp His Cys Ser Phe Thr Asp
    130                 135                 140

Lys Ile Thr Phe Asp Gln Val Ile Asn Leu Asn Asn Thr Ala Arg Ala
145                 150                 155                 160

Ile Lys Asp Gly Ser Val Gly Pro Gly Met Tyr His Arg Val Asp
                165                 170                 175

His Cys Phe Phe Ser Asn Pro Gln Lys Pro Gly Asn Ala Gly Gly
        180                 185                 190

Ile Arg Ile Gly Tyr Tyr Arg Asn Asp Ile Gly Arg Cys Leu Val Asp
            195                 200                 205

Ser Asn Leu Phe Met Arg Gln Asp Ser Glu Ala Glu Ile Ile Thr Ser
        210                 215                 220

Lys Ser Gln Glu Asn Val Tyr Tyr Gly Asn Thr Tyr Leu Asn Cys Gln
225                 230                 235                 240

Gly Thr Met Asn Phe Arg His Gly Asp His Gln Val Ala Ile Asn Asn
                245                 250                 255

Phe Tyr Ile Gly Asn Asp Gln Arg Phe Gly Tyr Gly Gly Met Phe Val
            260                 265                 270

Trp Gly Ser Arg His Val Ile Ala Cys Asn Tyr Phe Glu Leu Ser Glu
        275                 280                 285

Thr Ile Lys Ser Arg Gly Asn Ala Ala Leu Tyr Leu Asn Pro Gly Ala
        290                 295                 300

Met Ala Ser Glu His Ala Leu Ala Phe Asp Met Leu Ile Ala Asn Asn
305                 310                 315                 320

Ala Phe Ile Asn Val Asn Gly Tyr Ala Ile His Phe Asn Pro Leu Asp
                325                 330                 335

Glu Arg Arg Lys Glu Tyr Cys Ala Ala Asn Arg Leu Lys Phe Glu Thr
            340                 345                 350

Pro His Gln Leu Met Leu Lys Gly Asn Leu Phe Phe Lys Asp Lys Pro
        355                 360                 365

Tyr Val Tyr Pro Phe Phe Lys Asp Asp Tyr Phe Ile Ala Gly Lys Asn
    370                 375                 380

Ser Trp Thr Gly Asn Val Ala Leu Gly Val Glu Lys Gly Ile Pro Val
385                 390                 395                 400

Asn Ile Ser Ala Asn Arg Ser Ala Tyr Lys Pro Val Lys Ile Lys Asp
                405                 410                 415

Ile Gln Pro Ile Glu Gly Ile Ala Leu Asp Leu Asn Ala Leu Ile Ser
            420                 425                 430

Lys Gly Ile Thr Gly Lys Pro Leu Ser Trp Asp Glu Val Arg Pro Tyr
        435                 440                 445

Trp Leu Lys Glu Met Pro Gly Thr Tyr Ala Leu Thr Ala Arg Leu
    450                 455                 460
```

<210> SEQ ID NO 16
<211> LENGTH: 365
<212> TYPE: PRT
<213> ORGANISM: Artificial
<220> FEATURE:
<223> OTHER INFORMATION: Synthetic polypeptide, C(delta)120
      chondroitinase B (Q[sub]26 - K[sub]390)

<400> SEQUENCE: 16

```
Gln Val Val Ala Ser Asn Glu Thr Leu Tyr Gln Val Val Lys Glu Val
1               5                   10                  15

Lys Pro Gly Gly Leu Val Gln Ile Ala Asp Gly Thr Tyr Lys Asp Val
            20                  25                  30

Gln Leu Ile Val Ser Asn Ser Gly Lys Ser Gly Leu Pro Ile Thr Ile
            35                  40                  45

Lys Ala Leu Asn Pro Gly Lys Val Phe Phe Thr Gly Asp Ala Lys Val
50                  55                  60

Glu Leu Arg Gly Glu His Leu Ile Leu Glu Gly Ile Trp Phe Lys Asp
65                  70                  75                  80

Gly Asn Arg Ala Ile Gln Ala Trp Lys Ser His Gly Pro Gly Leu Val
                85                  90                  95

Ala Ile Tyr Gly Ser Tyr Asn Arg Ile Thr Ala Cys Val Phe Asp Cys
            100                 105                 110

Phe Asp Glu Ala Asn Ser Ala Tyr Ile Thr Thr Ser Leu Thr Glu Asp
            115                 120                 125

Gly Lys Val Pro Gln His Cys Arg Ile Asp His Cys Ser Phe Thr Asp
            130                 135                 140

Lys Ile Thr Phe Asp Gln Val Ile Asn Leu Asn Asn Thr Ala Arg Ala
145                 150                 155                 160

Ile Lys Asp Gly Ser Val Gly Pro Gly Met Tyr His Arg Val Asp
                165                 170                 175

His Cys Phe Phe Ser Asn Pro Gln Lys Pro Gly Asn Ala Gly Gly
            180                 185                 190

Ile Arg Ile Gly Tyr Tyr Arg Asn Asp Ile Gly Arg Cys Leu Val Asp
            195                 200                 205

Ser Asn Leu Phe Met Arg Gln Asp Ser Glu Ala Glu Ile Ile Thr Ser
210                 215                 220

Lys Ser Gln Glu Asn Val Tyr Tyr Gly Asn Thr Tyr Leu Asn Cys Gln
225                 230                 235                 240

Gly Thr Met Asn Phe Arg His Gly Asp His Gln Val Ala Ile Asn Asn
                245                 250                 255

Phe Tyr Ile Gly Asn Asp Gln Arg Phe Gly Tyr Gly Gly Met Phe Val
            260                 265                 270

Trp Gly Ser Arg His Val Ile Ala Cys Asn Tyr Phe Glu Leu Ser Glu
            275                 280                 285

Thr Ile Lys Ser Arg Gly Asn Ala Ala Leu Tyr Leu Asn Pro Gly Ala
290                 295                 300

Met Ala Ser Glu His Ala Leu Ala Phe Asp Met Leu Ile Ala Asn Asn
305                 310                 315                 320

Ala Phe Ile Asn Val Asn Gly Tyr Ala Ile His Phe Asn Pro Leu Asp
                325                 330                 335

Glu Arg Arg Lys Glu Tyr Cys Ala Ala Asn Arg Leu Lys Phe Glu Thr
            340                 345                 350

Pro His Gln Leu Met Leu Lys Gly Asn Leu Phe Phe Lys
            355                 360                 365

<210> SEQ ID NO 17
<211> LENGTH: 245
<212> TYPE: PRT
<213> ORGANISM: Artificial
<220> FEATURE:
<223> OTHER INFORMATION: Synthetic polypeptide, N(delta)120 C(delta)120
      chondroitinase B (I[sub]146 - K[sub]390)

<400> SEQUENCE: 17
```

Ile Thr Thr Ser Leu Thr Glu Asp Gly Lys Val Pro Gln His Cys Arg
1               5                   10                  15

Ile Asp His Cys Ser Phe Thr Asp Lys Ile Thr Phe Asp Gln Val Ile
            20                  25                  30

Asn Leu Asn Asn Thr Ala Arg Ala Ile Lys Asp Gly Ser Val Gly Gly
        35                  40                  45

Pro Gly Met Tyr His Arg Val Asp His Cys Phe Phe Ser Asn Pro Gln
    50                  55                  60

Lys Pro Gly Asn Ala Gly Gly Ile Arg Ile Gly Tyr Tyr Arg Asn
65              70                  75                  80

Asp Ile Gly Arg Cys Leu Val Asp Ser Asn Leu Phe Met Arg Gln Asp
                85                  90                  95

Ser Glu Ala Glu Ile Ile Thr Ser Lys Ser Gln Glu Asn Val Tyr Tyr
            100                 105                 110

Gly Asn Thr Tyr Leu Asn Cys Gln Gly Thr Met Asn Phe Arg His Gly
            115                 120                 125

Asp His Gln Val Ala Ile Asn Asn Phe Tyr Ile Gly Asn Asp Gln Arg
        130                 135                 140

Phe Gly Tyr Gly Gly Met Phe Val Trp Gly Ser Arg His Val Ile Ala
145                 150                 155                 160

Cys Asn Tyr Phe Glu Leu Ser Glu Thr Ile Lys Ser Arg Gly Asn Ala
            165                 170                 175

Ala Leu Tyr Leu Asn Pro Gly Ala Met Ala Ser Glu His Ala Leu Ala
            180                 185                 190

Phe Asp Met Leu Ile Ala Asn Asn Ala Phe Ile Asn Val Asn Gly Tyr
            195                 200                 205

Ala Ile His Phe Asn Pro Leu Asp Glu Arg Arg Lys Glu Tyr Cys Ala
        210                 215                 220

Ala Asn Arg Leu Lys Phe Glu Thr Pro His Gln Leu Met Leu Lys Gly
225                 230                 235                 240

Asn Leu Phe Phe Lys
            245

<210> SEQ ID NO 18
<211> LENGTH: 2103
<212> TYPE: DNA
<213> ORGANISM: Pedobacter Heparinus

<400> SEQUENCE: 18
atgaagaaat tatttgtaac ctgtatagtc ttttctctcta ttttaagtcc tgctctgctt      60
attgcacagc agaccggtac tgcagaactg attatgaagc gggtgatgct ggaccttaaa     120
aagcctttgc gcaatatgga taaggtggcg gaaaagaacc tgaatacgct gcagcctgac     180
ggtagctgga aggatgtgcc ttataaagat gatgccatga ccaattggtt gccaaacaac     240
cacctgctac aattggaaac tattatacag gcttatattg aaaaagatag tcactattat     300
ggcgacgata aagtgtttga ccagatttcc aaagctttta gtattggta tgacagcgac     360 ccgaaaagcc gcaactggtg gcacaatgaa attgccactc gcaggccct tggtgaaatg     420 ctgatcctga tgcgttacgg taaaaagccg cttgatgaag cattggtgca taaattgacc     480
gaaagaatga agcggggcga accggagaag aaaacggggg ccaacaaaac agatatcgcc     540
ctgcattact ttatcgtgc tttgttaacg tctgatgagg ctttgctttc cttcgccgta     600
aaagaattgt tttatcccgt acagtttgta cactatgagg aaggcctgca atacgattat     660
tcctacctgc agcacggtcc gcaattacag atatcgagct acggtgccgt atttattacc     720

```
ggggtactga aacttgccaa ttacgttagg gatacccctt atgctttaag taccgagaaa    780
ctggctatat tttcaaagta ttaccgcgac agttatctga aagctatccg tggaagttat    840
atggatttta acgtagaagg ccgcggagta agccggccag acattctaaa taaaaaggca    900
gaaaaaaaga ggttgctggt ggcgaagatg atcgatctta agcatactga agaatgggct    960
gatgcgatag ccaggacaga tagcacagtt gcggccggct ataagattga gccctatcac   1020
catcagttct ggaatggtga ttatgtgcaa catttaagac tgcctattc ttttaatgtt    1080
cgtatggtga gtaagcggac ccgacgcagt gaatccggca ataagaaaa cctgctgggc    1140
aggtatttat ctgatggggc tactaacata caattgcgcg gaccagaata ctataacatt   1200
atgccggtat gggaatggga caagattcct ggcataacca gccgtgatta tttaaccgac   1260
agacctttga cgaagctttg gggagagcag gggagcaatg actttgcagg aggggtgtct   1320
gatggtgtat acgggccag tgcctacgca ttggattacg atagcttaca ggcaaagaaa    1380
gcctggttct tttttgacaa agagattgta tgtcttggtg ccggtatcaa cagcaatgcc   1440
cctgaaaaca ttaccactac ccttaaccag agctggttaa atggcccggt tataagtact   1500
gcaggtaaaa ccggccgggg taaaataaca acgtttaaag cacagggaca gttctggttg   1560
ttgcacgatg cgattggtta ttactttcct gaaggggcca accttagtct gagtacccag   1620
tcgcaaaaag gcaattggtt ccacatcaac aattcacatt caaaagatga agtttctggt   1680
gatgtattta agctttggat caaccatggt gccaggccag aaaatgcgca gtatgcttat   1740
atcgttttgc cgggaataaa caagccggaa gaaattaaaa aatataatgg aacggcaccg   1800
aaagtccttg ccaataccaa ccagctgcag gcagtttatc atcagcagtt agatatggta   1860
caggctatct tctatacagc tggaaaatta agcgtagcgg gcatagaaat tgaaacagat   1920
aagccatgtg cagtgctgat caagcacatc aatggcaagc aggtaatttg ggctgccgat   1980
ccattgcaaa agaaaagac tgcagtgttg agcatcaggg atttaaaaac aggaaaaaca   2040
aatcgggtaa aaattgattt ccgcaacag gaatttgcag gtgcaacggt tgaactgaaa    2100
tag                                                                  2103
```

<210> SEQ ID NO 19
<211> LENGTH: 1067
<212> TYPE: DNA
<213> ORGANISM: Artificial
<220> FEATURE:
<223> OTHER INFORMATION: Snythetic polynucleotide of chondroitinase AC
      nucelic acid deletion N(delta)50 C(delta)275
      (a[SUB]220 - T[sub]1278)

<400> SEQUENCE: 19

```
atgccatgac caattggttg ccaaacaacc acctgctaca attggaaact attatacagg     60
cttatattga aaagatagt cactattatg gcgacgataa agtgtttgac cagatttcca    120
aagcttttaa gtattggtat gacagcgacc cgaaaagccg caactggtgg cacaatgaaa    180
ttgccactcc gcaggcccctt ggtgaaatgc tgatcctgat gcgttacggt aaaaagccgc    240
ttgatgaagc attggtgcat aaattgaccg aaagaatgaa gcgggcgaa ccggagaaga    300
aaacggggc caacaaaaca gatatcgccc tgcattactt ttatcgtgct tgttaacgt     360
ctgatgagc tttgctttcc ttcgccgtaa agaattgtt ttatccccgta cagtttgtac     420
actatgagga aggcctgcaa tacgattatt cctacctgca gcacggtccg caattacaga    480
tatcgagcta cggtgccgta tttattaccg gggtactgaa acttgccaat tacgttaggg    540
ataccccctta tgctttaagt accgagaaac tggctatatt ttcaaagtat taccgcgaca    600
```

```
gttatctgaa agctatccgt ggaagttata tggattttaa cgtagaaggc cgcggagtaa      660
gccggccaga cattctaaat aaaaaggcag aaaaaaagag gttgctggtg gcgaagatga      720
tcgatcttaa gcatactgaa gaatgggctg atgcgatagc caggacagat agcacagttg      780
cggccggcta taagattgag ccctatcacc atcagttctg gaatggtgat tatgtgcaac      840
atttaagacc tgcctattct tttaatgttc gtatggtgag taagcggacc cgacgcagtg      900
aatccggcaa taaagaaaac ctgctgggca ggtatttatc tgatgggcgt actaacatac      960
aattgcgcgg accagaatac tataacatta tgccggtatg ggaatgggac aagattcctg     1020
gcataaccag ccgtgattat ttaaccgaca gacctttgac gaagctt                   1067
```

<210> SEQ ID NO 20
<211> LENGTH: 1521
<212> TYPE: DNA
<213> ORGANISM: Pedobacter Heparinus Chondroitinase B

<400> SEQUENCE: 20

```
atgaagatgc tgaataaact agccggatac ttattgccga tcatggtgct gctgaatgtg       60
gcaccatgct taggtcaggt tgttgcttca aatgaaactt ataccaggtt tgtaaaggag      120
gtaaaacccg gtggtctggt acagattgcc gatgggactt ataaagatgt tcagctgatt      180
gtcagcaatt caggaaaatc tggttttgccc atcactatta aagccctgaa cccgggtaag      240 gttttttttta ccggagatgc taaagtagag ctgaggggcg agcacctgat actggaaggc      300
atctggttta aagacgggaa cagagctatt caggcatgga aatcacatgg acccggattg      360
gtggctatat atggtagcta taaccgcatt accgcatgtg tatttgattg ttttgatgaa      420
gccaattctg cttacattac tacttcgctt accgaagacg gaaaggtacc tcaacattgc      480
cgcatagacc attgcagttt taccgataag atcacttttg accaggtaat taacctgaac      540
aatacagcca gagctattaa agacggttcg gtgggaggac cggggatgta ccatcgtgtt      600
gatcactgtt ttttttccaa tccgcaaaaa ccgggtaatg ccggaggggg aatcaggatt      660
ggctattacc gtaatgatat aggccgttgt ctggtagact ctaacctgtt tatgcgtcag      720
gattcggaag cagagatcat caccagcaaa tcgcaggaaa atgttttatta tggtaatact      780 tacctgaatt gccagggcac catgaacttt cgtcacggtg atcatcaggt ggccattaac      840 aattttttata taggcaatga ccagcgattt ggatacgggg gaatgtttgt ttggggaagc      900
aggcatgtca tagcctgtaa ttatttttgag ctgtccgaaa ccataaagtc gagggggaac      960
gccgcattgt atttaaaccc cggtgctatg gcttcggagc atgctcttgc ttttcgatatg     1020 ttgatagcca acaacgcttt catcaatgta aatgggtatg ccatccattt taatccattg     1080
gatgagcgca gaaaagaata ttgtcagcc aataggctta agttcgaaac cccgcaccag     1140
ctaatgttaa aaggcaatct ttttcttttaag gataaacctt atgttttaccc atttttttaaa     1200 gatgattatt ttatagcagg gaaaaatagc tggactggta atgtagcctt aggtgtggaa     1260
aagggaatcc ctgttaacat ttcggccaat aggtctgcct ataagccggt aaaaattaaa     1320
gatatccagc ccatagaagg aatcgctctt gatctcaatg cgctgatcag caaaggcatt     1380
acaggaaagc cccttagctg ggatgaagta aggccctact ggttaaaaga aatgcccggg     1440
acgtatgctt taacgccagg cttttctgca gatagggctg caaagtttaa agccgtaatt     1500
aaaagaaata aagagcactg a                                                1521
```

<210> SEQ ID NO 21
<211> LENGTH: 735
<212> TYPE: DNA

```
<213> ORGANISM: Artificial
<220> FEATURE:
<223> OTHER INFORMATION: Synthetic polynucleotide of chondroitinase B
      nucleic acid deletion N(delta)120 C(delta)120
      (a[sub]436 - g[sub]1170)

<400> SEQUENCE: 21
attactactt cgcttaccga agacggaaag gtacctcaac attgccgcat agaccattgc      60
agttttaccg ataagatcac ttttgaccag gtaattaacc tgaacaatac agccagagct    120
attaaagacg gttcggtggg aggaccgggg atgtaccatc gtgttgatca ctgttttttt    180
tccaatccgc aaaaaccggg taatgccgga gggggaatca ggattggcta ttaccgtaat    240
gatataggcc gttgtctggt agactctaac ctgtttatgc gtcaggattc ggaagcagag    300
atcatcacca gcaaatcgca ggaaaatgtt tattatggta atacttacct gaattgccag    360
ggcaccatga actttcgtca cggtgatcat caggtggcca ttaacaattt ttatataggc    420
aatgaccagc gatttggata cggggaatg tttgtttggg aagcaggca tgtcatagcc     480
tgtaattatt ttgagctgtc cgaaaccata aagtcgaggg ggaacgccgc attgtattta    540
aaccccggtg ctatggcttc ggagcatgct cttgctttcg atatgttgat agccaacaac    600
gctttcatca atgtaaatgg gtatgccatc cattttaatc cattggatga gcgcagaaaa    660
gaatattgtg cagccaatag gcttaagttc gaaaccccgc accagctaat gttaaaggc    720
aatctttttct ttaag                                                     735

<210> SEQ ID NO 22
<211> LENGTH: 3980
<212> TYPE: DNA
<213> ORGANISM: Artificial
<220> FEATURE:
<223> OTHER INFORMATION: Synthetic polynucleotide LOCUS (I29953)

<400> SEQUENCE: 22
ggaattccat cactcaatca ttaaatttag gcacaacgat gggctatcag cgttatgaca      60
aatttaatga aggacgcatt ggtttcactg ttagccagcg tttctaagga gaaaaataat    120
gccgatattt cgttttactg cacttgcaat gacattgggg ctattatcag cgccttataa    180
cgcgatggca gccaccagca atcctgcatt tgatcctaaa aatctgatgc agtcagaaat    240
ttaccatttt gcacaaaata acccattagc agacttctca tcagataaaa actcaatact    300
aacgttatct gataaacgta gcattatggg aaaccaatct cttttatgga atggaaagg    360
tggtagtagc tttactttac ataaaaaact gattgtcccc accgataaag aagcatctaa    420
agcatgggga cgctcatcta cccccgtttt ctcatttgg ctttacaatg aaaaaccgat    480
tgatggttat cttactatcg atttcggaga aaaactcatt tcaaccagtg aggctcaggc    540
aggctttaaa gtaaaattag atttcactgg ctggcgtgct gtgggagtct ctttaaataa    600
cgatcttgaa aatcgagaga tgaccttaaa tgcaaccaat acctcctctg atggtactca    660
agacagcatt gggcgttctt taggtgctaa agtcgatagt attcgttta aagcgccttc    720
taatgtgagt cagggtgaaa tctatatcga ccgtattatg tttctgtcg atgatgctcg    780
ctaccaatgg tctgattatc aagtaaaaac tcgcttatca gaacctgaaa ttcaatttca    840
caacgtaaag ccacaactac ctgtaacacc tgaaaattta gcggccattg atcttattcg    900
ccaacgtcta attaatgaat ttgtcggagg tgaaaaagag acaaacctcg cattagaaga    960
gaatatcagc aaattaaaaa gtgatttcga tgctcttaat attcacactt agcaaatgg    1020
tggaacgcaa ggcagacatc tgatcactga taaacaaatc attatttatc aaccagagaa   1080
```

```
tcttaactcc caagataaac aactatttga taattatgtt attttaggta attacacgac    1140
attaatgttt aatattagcc gtgcttatgt gctggaaaaa gatcccacac aaaaggcgca    1200
actaaagcag atgtacttat taatgacaaa gcatttatta gatcaaggct ttgttaaagg    1260
gagtgcttta gtgacaaccc atcactgggg atacagttct cgttggtggt atatttccac    1320
gttattaatg tctgatgcac taaaagaagc gaacctacaa actcaagttt atgattcatt    1380
actgtggtat tcacgtgagt ttaaaagtag ttttgatatg aaagtaagtg ctgatagctc    1440
tgatctagat tatttcaata ccttatctcg ccaacattta gccttattat tactagagcc    1500
tgatgatcaa aagcgtatca acttagttaa tactttcagc cattatatca ctggcgcatt    1560
aacgcaagtg ccaccgggtg gtaaagatgg tttacgccct gatggtacag catggcgaca    1620
tgaaggcaac tatccgggct actctttccc agcctttaaa aatgcctctc agcttattta    1680
tttattacgc gatacaccat tttcagtggg tgaaagtggt tggaataacc tgaaaaaagc    1740
gatggtttca gcgtggatct acagtaatcc agaagttgga ttaccgcttg caggaagaca    1800 ccctttta ac tcaccttcgt taaaatcagt cgctcaaggc tattactggc ttgccatgtc    1860
tgcaaaatca tcgcctgata aaacacttgc atctatttat cttgcgatta gtgataaaac    1920
acaaaatgaa tcaactgcta tttttggaga aactattaca ccagcgtctt tacctcaagg    1980
tttctatgcc tttaatggcg gtgcttttgg tattcatcgt tggcaagata aaatggtgac    2040
actgaaagct tataacacca atgtttggtc atctgaaatt tataacaaag ataaccgtta    2100
tggccgttac caaagtcatg gtgtcgctca aatagtgagt aatggctcgc agctttcaca    2160
gggctatcag caagaaggtt gggattggaa tagaatgcaa ggggcaacca ctattcacct    2220
tcctcttaaa gacttagaca gtcctaaacc tcatacctta atgcaacgtg gagagcgtgg    2280
atttagcgga acatcatccc ttgaaggtca atatggcatg atggcattcg atcttattta    2340
tcccgccaat cttgagcgtt ttgatcctaa tttcactgcg aaaagagtg tattagccgc    2400 tgataatcac ttaattttta ttggtagcaa tataaatagt agtgataaaa ataaaaatgt    2460
tgaaacgacc ttattccaac atgccattac tccaacatta aataccctt ggattaatgg    2520 acaaaagata gaaaacatgc cttatcaaac aacacttcaa caaggtgatt ggttaattga    2580
tagcaatggc aatggttact taattactca agcagaaaaa gtaaatgtaa gtcgccaaca    2640
tcaggtttca gcgaaaaata aaaatcgcca accgacagaa ggaaacttta gctcggcatg    2700
gatcgatcac agcactcgcc ccaaagatgc cagttatgag tatatggtct ttttagatgc    2760
gacacctgaa aaatgggag agatggcaca aaaattccgt gaaaataatg gttatatca    2820 ggttcttcgt aaggataaag acgttcatat tattctcgat aaactcagca atgtaacggg    2880
atatgccttt tatcagccag catcaattga agacaaatgg atcaaaaagg ttaataaacc    2940
tgcaattgtg atgactcatc gacaaaaaga cactcttatt gtcagtgcag ttacacctga    3000
tttaaatatg actcgccaaa aagcagcaac tcctgtcacc atcaatgtca cgattaatgg    3060
caaatggcaa tctgctgata aaaatagtga agtgaaatat caggtttctg gtgataacac    3120
tgaactgacg tttacgagtt actttggtat tccacaagaa atcaaactct cgccactccc    3180
ttgatttaat caaaagaacg ctcttgcgtt ccttttttat ttgcaggaaa tctgattatg    3240
ctaataaaaa accctttagc ccacgcggtt acattaagcc tctgtttatc attacccgca    3300
caagcattac ccactctgtc tcatgaagct ttcggcgata tttatctttt tgaaggtgaa    3360
ttacccaata cccttaccac ttcaaataat aatcaattat cgctaagcaa acagcatgct    3420
aaagatggtg aacaatcact caaatggcaa tatcaaccac aagcaacatt aacactaaat    3480
```

```
aatattgtta attaccaaga tgataaaaat acagccacac cactcacttt tatgatgtgg   3540
atttataatg aaaaacctca atcttcccca ttaacgttag catttaaaca aaataataaa   3600
attgcactaa gttttaatgc tgaacttaat tttacggggt ggcgaggtat tgctgttcct   3660
tttcgtgata tgcaaggctc tgcgacaggt caacttgatc aattagtgat caccgctcca   3720
aaccaagccg gaacactctt ttttgatcaa atcatcatga gtgtaccgtt agacaatcgt   3780
tgggcagtac ctgactatca aacaccttac gtaaataacg cagtaaacac gatggttagt   3840
aaaaactgga gtgcattatt gatgtacgat cagatgtttc aagcccatta ccctacttta   3900
aacttcgata ctgaatttcg cgatgaccaa acagaaatgg cttcgattta tcagcgcttt   3960
gaatattatc aaggaattcc                                               3980
```

<210> SEQ ID NO 23
<211> LENGTH: 3835
<212> TYPE: DNA
<213> ORGANISM: Artificial
<220> FEATURE:
<223> OTHER INFORMATION: Synthetic polynucleotide, TAT fusion
      chondroitinase ABC I nucelic acid

<400> SEQUENCE: 23

```
ggtcgtaaaa agcgtcgtca acgtcgtcgt ggtggtggtg gtggtgccac cagcaatcct     60
gcatttgatc ctaaaaatct gatgcagtca gaaatttacc attttgcaca aaataaccca    120
ttagcagact tctcatcaga taaaaactca atactaacgt tatctgataa acgtagcatt    180
atgggaaacc aatctctttt atggaaatgg aaaggtggta gtagctttac tttacataaa    240
aaactgattg tccccaccga taagaagca tctaaagcat ggggacgctc atctaccccc    300
gttttctcat tttggcttta caatgaaaaa ccgattgatg ttatcttac tatcgatttc    360 ggagaaaaac tcatttcaac cagtgaggct caggcaggct ttaaagtaaa attagatttc    420
actggctggc gtgctgtggg agtctcttta aataacgatc ttgaaaatcg agagatgacc    480
ttaaatgcaa ccaataccctc ctctgatggt actcaagaca gcattgggcg ttctttaggt    540
gctaaagtcg atagtattcg ttttaaagcg ccttctaatg tgagtcaggg tgaaatctat    600
atcgaccgta ttatgttttc tgtcgatgat gctcgctacc aatggtctga ttatcaagta    660
aaaactcgct tatcagaacc tgaaattcaa tttcacaacg taaagccaca actacctgta    720
acacctgaaa atttagcggc cattgatctt attcgccaac gtctaattaa tgaatttgtc    780
ggaggtgaaa aagagacaaa cctcgcatta gaagagaata tcagcaaatt aaaaagtgat    840
ttcgatgctc ttaatattca cactttagca aatggtggaa cgcaaggcag acatctgatc    900
actgataaac aaatcattat ttatcaacca gagaatctta actcccaaga taaacaacta    960
tttgataatt atgttatttt aggtaattac acgacattaa tgtttaatat tagccgtgct   1020
tatgtgctgg aaaagatcc cacacaaaag gcgcaactaa agcagatgta cttattaatg   1080
acaaagcatt tattagatca aggctttgtt aaagggagtg ctttagtgac aacccatcac   1140
tggggataca gttctcgttg gtggtatatt tccacgttat taatgtctga tgcactaaaa   1200
gaagcgaacc tacaaactca agtttatgat tcattactgt ggtattcacg tgagtttaaa   1260
agtagttttg atatgaaagt aagtgctgat agctctgatc tagattattt caataccta    1320 tctcgccaac atttagcctt attattacta gagcctgatg atcaaaagcg tatcaactta   1380
gttaatactt tcagccatta tatcactggc gcattaacgc aagtgccacc gggtggtaaa   1440
gatggtttac gccctgatgg tacagcatgg cgacatgaag gcaactatcc gggctactct   1500
ttcccagcct ttaaaaatgc ctctcagctt atttattat tacgcgatac accattttca   1560
```

```
gtgggtgaaa gtggttggaa taacctgaaa aaagcgatgg tttcagcgtg gatctacagt    1620
aatccagaag ttggattacc gcttgcagga agacacccct ttaactcacc ttcgttaaaa    1680
tcagtcgctc aaggctatta ctggcttgcc atgtctgcaa aatcatcgcc tgataaaaca    1740
cttgcatcta tttatcttgc gattagtgat aaaacacaaa atgaatcaac tgctattttt    1800
ggagaaacta ttacaccagc gtctttacct caaggtttct atgcctttaa tggcggtgct    1860
tttggtattc atcgttggca agataaaatg gtgacactga aagcttataa caccaatgtt    1920
tggtcatctg aaatttataa caaagataac cgttatggcc gttaccaaag tcatggtgtc    1980
gctcaaatag tgagtaatgg ctcgcagctt tcacagggct atcagcaaga aggttgggat    2040
tggaatagaa tgcaaggggc aaccactatt caccttcctc ttaaagactt agacagtcct    2100
aaacctcata ccttaatgca acgtggagag cgtggattta gcggaacatc atcccttgaa    2160
ggtcaatatg gcatgatggc attcgatctt atttatcccg ccaatcttga gcgttttgat    2220
cctaatttca ctgcgaaaaa gagtgtatta gccgctgata atcacttaat ttttattggt    2280
agcaatataa atagtagtga taaaaataaa aatgttgaaa cgaccttatt ccaacatgcc    2340
attactccaa cattaaatac cctttggatt aatggacaaa agatagaaaa catgccttat    2400
caaacaacac ttcaacaagg tgattggtta attgatagca atggcaatgg ttacttaatt    2460
actcaagcag aaaagtaaa tgtaagtcgc aacatcagg tttcagcgga aaataaaaat    2520
cgccaaccga cagaaggaaa ctttagctcg gcatggatcg atcacagcac tcgccccaaa    2580
gatgccagtt atgagtatat ggtcttttta gatgcgacac ctgaaaaaat gggagagatg    2640
gcacaaaaat tccgtgaaaa taatgggtta tatcaggttc ttcgtaagga taaagacgtt    2700
catattattc tcgataaact cagcaatgta acgggatatg cctttatca gccagcatca    2760 attgaagaca aatggatcaa aaaggttaat aaacctgcaa ttgtgatgac tcatcgacaa    2820
aaagacactc ttattgtcag tgcagttaca cctgatttaa atatgactcg ccaaaaagca    2880
gcaactcctg tcaccatcaa tgtcacgatt aatggcaaat ggcaatctgc tgataaaaat    2940
agtgaagtga aatatcaggt ttctggtgat aacactgaac tgacgtttac gagttacttt    3000
ggtattccac aagaaatcaa actctcgcca ctcccttgat ttaatcaaaa gaacgctctt    3060
gcgttccttt tttatttgca ggaaatctga ttatgctaat aaaaaaccct ttagcccacg    3120
cggttacatt aagcctctgt ttatcattac ccgcacaagc attcccact ctgtctcatg    3180 aagctttcgg cgatatttat cttttgaag gtgaattacc caatacccct accacttcaa    3240
ataataatca attatcgcta agcaaacagc atgctaaaga tggtgaacaa tcactcaaat    3300
ggcaatatca accacaagca acattaacac taaataatat tgttaattac caagatgata    3360
aaaatacagc cacaccactc acttttatga tgtggattta taatgaaaaa cctcaatctt    3420
ccccattaac gttagcattt aaacaaaata ataaaattgc actaagtttt aatgctgaac    3480
ttaattttac ggggtggcga ggtattgctg ttccttttcg tgatatgcaa ggctctgcga    3540
caggtcaact tgatcaatta gtgatcaccg ctccaaacca agccggaaca ctcttttttg    3600
atcaaatcat catgagtgta ccgttagaca atcgttgggc agtacctgac tatcaaaacac    3660 cttacgtaaa taacgcagta aacacgatgg ttagtaaaaa ctggagtgca ttattgatgt    3720
acgatcagat gtttcaagcc cattacccta ctttaaactt cgatactgaa tttcgcgatg    3780
accaaacaga aatggcttcg atttatcagc gctttgaata ttatcaagga attcc        3835
```

<210> SEQ ID NO 24
<211> LENGTH: 15

```
<212> TYPE: PRT
<213> ORGANISM: Artificial
<220> FEATURE:
<223> OTHER INFORMATION: Synthetic polypeptide, HIV TAT sequence and Gly
      penta linker

<400> SEQUENCE: 24

Gly Arg Lys Lys Arg Arg Gln Arg Arg Gly Gly Gly Gly Gly
1               5                   10                  15

<210> SEQ ID NO 25
<211> LENGTH: 2973
<212> TYPE: DNA
<213> ORGANISM: Artificial
<220> FEATURE:
<223> OTHER INFORMATION: Synthetic polynucleotide, Chondroitinase ABC II
      Nucleic acid

<400> SEQUENCE: 25
ttacccactc tgtctcatga agctttcggc gatatttatc ttttgaagg cgaattaccc      60 aatatcctta ccacttcaaa taataatcaa ttatcgctaa gcaaacagca tgctaaagat    120
ggtgaacaat cactcaaatg gcaatatcaa ccacaagcaa cattaacact aaataatatt    180
gttaattacc aagatgataa aaatacagcc acaccactca cttttatgat gtggatttat    240
aatgaaaaac ctcaatcttc cccattaacg ttagcattta acaaaataa taaaattgca    300 ctaagtttta atgctgaact taattttacg gggtggcgag gtattgctgt tccttttcgt    360
gatatgcaag gctctgcgac aggtcaactt gatcaattag tgatcaccgc tccaaaccaa    420
gccggaacac tcttttttga tcaaatcatc atgagtgtac cgttagacaa tcgttgggca    480
gtacctgact atcaaacacc ttacgtaaat aacgcagtaa acacgatggt tagtaaaaac    540
tggagtgcat tattgatgta cgatcagatg tttcaagccc attccctac tttaaacttc    600 gatactgaat ttcgcgatga ccaaacagaa atggcttcga tttatcagcg ctttgaatat    660
tatcaaggaa ttcgtagtga taaaaaaatt actccagata tgctagataa acatttagcg    720
ttatgggaaa aattggggtt aacacaacac gctgatggct caatcacagg aaaagcccctt    780 gatcaccctaa accggcaaca ttttatgaaa gtcgaaggtg tatttagtga ggggactcaa    840
aaagcattac ttgatgccaa tatgctaaga gatgtgggca aaacgcttct tcaaactgct    900
atttacttgc gtagcgattc attatcagca actggtagaa aaaattaga gagcgctat    960 ttattaggta ctcgttatgt ccttgaacaa ggttttacac gaggaagtgg ttatcaaatt   1020
attactcatg ttggttacca aaccagaaaa ctttttgatg catggtttat tggccgtcat   1080
gttcttgcaa aaaataacct tttagcccccc actcaacaag ctatgatgtg gtacaacgcc   1140
acaggacgta ttttgaaaaa agataatgaa attgttgatg caaatgtcga tattctcaat   1200
actcaattgc aatggatgat aaaaagctta ttgatgctac cggattatca acaacgtcaa   1260
caagccttag cgcaactgca agttggcta aataaaacca ttctaagctc aaaaggtgtt   1320
gctggcggtt tcaaatctga tggttctatt tttcaccatt cacaacatta cccgcttat    1380 gctaaagatg catttggtgg tttagcaccc agtgtttatg cattaagtga ttcacctttt   1440
cgcttatcta cttcagcaca tgagcattta aaagatgttt tgttaaaaat gcggatctac   1500
accaaagaga cacaaattcc tgtggtatta agtggtcgtc atccaactgg gttgcataaa   1560
atagggatcg cgccatttaa atggatggca ttagcaggaa ccccagatgg caaacaaaag   1620
ttagatacca cattatccgc cgcttatgca aacttagaca caaaacgca ttttgaaggc   1680 attaacgctg aaagtgagcc agtcggcgca tgggcaatga attatgcatc aatggcaata   1740
```

```
caacgaagag catcgaccca atcaccacaa caaagctggc tcgccatagc gcgcggtttt    1800
agccgttatc ttgttggtaa tgaaagctat gaaaataaca accgttatgg tcgttattta    1860
caatatggac aattggaaat tattccagct gatttaactc aatcagggtt tagccatgct    1920
ggatgggatt ggaatagata tccaggtaca acaactattc atcttcccta taacgaactt    1980
gaagcaaaac ttaatcaatt acctgctgca ggtattgaag aaatgttgct ttcaacagaa    2040
agttactctg gtgcaaatac ccttaataat aacagtatgt tgccatgaa attacacggt     2100 cacagtaaat atcaacaaca aagcttaagg gcaaataaat cctatttctt atttgataat    2160
agagttattg ctttaggctc aggtattgaa atgatgata acaacatac gaccgaaaca       2220 acactattcc agtttgccgt ccctaaatta cagtcagtga tcattaatgg caaaaaggta    2280
aatcaattag atactcaatt aactttaaat aatgcagata cattaattga tcctgccggc    2340
aatttatata agctcactaa aggacaaact gtaaaattta gttatcaaaa acaacattca    2400
cttgatgata gaaattcaaa accaacagaa caattatttg caacagctgt tatttctcat    2460
ggtaaggcac cgagtaatga aaattatgaa tatgcaatag ctatcgaagc acaaaataat    2520
aaagctccca atacacagt attacaacat aatgatcagc tccatgcggt aaaagataaa     2580
ataacccaag aagagggata tggtttttttt gaagccacta agttaaaatc agcggatgca    2640
acattattat ccagtgatgc gccggttatg gtcatggcta aaatacaaaa tcagcaatta    2700
acattaagta ttgttaatcc tgatttaaat ttatatcaag gtagagaaaa agatcaattt    2760
gatgataaag gtaatcaaat cgaagttagt gtttattctc gtcattggct acagcagaa     2820 tcgcaatcaa caaatagtac tattaccgta aaaggaatat ggaaattaac gacacctcaa    2880
cccggtgtta ttattaagca ccacaataac aacactctta ttacgacaac aaccatacag    2940
gcaacaccta ctgttattaa tttagttaag taa                                 2973
```

<210> SEQ ID NO 26
<211> LENGTH: 990
<212> TYPE: PRT
<213> ORGANISM: Artificial
<220> FEATURE:
<223> OTHER INFORMATION: Synthetic polypeptide, Chondroitinase ABC II
    protein

<400> SEQUENCE: 26

```
Leu Pro Thr Leu Ser His Glu Ala Phe Gly Asp Ile Tyr Leu Phe Glu
1               5                   10                  15

Gly Glu Leu Pro Asn Ile Leu Thr Thr Ser Asn Asn Asn Gln Leu Ser
            20                  25                  30

Leu Ser Lys Gln His Ala Lys Asp Gly Glu Gln Ser Leu Lys Trp Gln
        35                  40                  45

Tyr Gln Pro Gln Ala Thr Leu Thr Leu Asn Asn Ile Val Asn Tyr Gln
    50                  55                  60

Asp Asp Lys Asn Thr Ala Thr Pro Leu Thr Phe Met Met Trp Ile Tyr
65                  70                  75                  80

Asn Glu Lys Pro Gln Ser Ser Pro Leu Thr Leu Ala Phe Lys Gln Asn
                85                  90                  95

Asn Lys Ile Ala Leu Ser Phe Asn Ala Glu Leu Asn Phe Thr Gly Trp
            100                 105                 110

Arg Gly Ile Ala Val Pro Phe Arg Asp Met Gln Gly Ser Ala Thr Gly
        115                 120                 125

Gln Leu Asp Gln Leu Val Ile Thr Ala Pro Asn Gln Ala Gly Thr Leu
    130                 135                 140
```

-continued

```
Phe Phe Asp Gln Ile Ile Met Ser Val Pro Leu Asp Asn Arg Trp Ala
145                 150                 155                 160

Val Pro Asp Tyr Gln Thr Pro Tyr Val Asn Asn Ala Val Asn Thr Met
            165                 170                 175

Val Ser Lys Asn Trp Ser Ala Leu Leu Met Tyr Asp Gln Met Phe Gln
        180                 185                 190

Ala His Tyr Pro Thr Leu Asn Phe Asp Thr Glu Phe Arg Asp Asp Gln
    195                 200                 205

Thr Glu Met Ala Ser Ile Tyr Gln Arg Phe Glu Tyr Tyr Gln Gly Ile
210                 215                 220

Arg Ser Asp Lys Lys Ile Thr Pro Asp Met Leu Asp Lys His Leu Ala
225                 230                 235                 240

Leu Trp Glu Lys Leu Gly Leu Thr Gln His Ala Asp Gly Ser Ile Thr
            245                 250                 255

Gly Lys Ala Leu Asp His Pro Asn Arg Gln His Phe Met Lys Val Glu
        260                 265                 270

Gly Val Phe Ser Glu Gly Thr Gln Lys Ala Leu Leu Asp Ala Asn Met
    275                 280                 285

Leu Arg Asp Val Gly Lys Thr Leu Leu Gln Thr Ala Ile Tyr Leu Arg
290                 295                 300

Ser Asp Ser Leu Ser Ala Thr Gly Arg Lys Lys Leu Glu Glu Arg Tyr
305                 310                 315                 320

Leu Leu Gly Thr Arg Tyr Val Leu Glu Gln Gly Phe Thr Arg Gly Ser
            325                 330                 335

Gly Tyr Gln Ile Ile Thr His Val Gly Tyr Gln Thr Arg Glu Leu Phe
        340                 345                 350

Asp Ala Trp Phe Ile Gly Arg His Val Leu Ala Lys Asn Asn Leu Leu
    355                 360                 365

Ala Pro Thr Gln Gln Ala Met Met Trp Tyr Asn Ala Thr Gly Arg Ile
370                 375                 380

Phe Glu Lys Asp Asn Glu Ile Val Asp Ala Asn Val Asp Ile Leu Asn
385                 390                 395                 400

Thr Gln Leu Gln Trp Met Ile Lys Ser Leu Leu Met Leu Pro Asp Tyr
            405                 410                 415

Gln Gln Arg Gln Gln Ala Leu Ala Gln Leu Gln Ser Trp Leu Asn Lys
        420                 425                 430

Thr Ile Leu Ser Ser Lys Gly Val Ala Gly Gly Phe Lys Ser Asp Gly
    435                 440                 445

Ser Ile Phe His His Ser Gln His Tyr Pro Ala Tyr Ala Lys Asp Ala
450                 455                 460

Phe Gly Gly Leu Ala Pro Ser Val Tyr Ala Leu Ser Asp Ser Pro Phe
465                 470                 475                 480

Arg Leu Ser Thr Ser Ala His Glu His Leu Lys Asp Val Leu Leu Lys
            485                 490                 495

Met Arg Ile Tyr Thr Lys Glu Thr Gln Ile Pro Val Val Leu Ser Gly
        500                 505                 510

Arg His Pro Thr Gly Leu His Lys Ile Gly Ile Ala Pro Phe Lys Trp
    515                 520                 525

Met Ala Leu Ala Gly Thr Pro Asp Gly Lys Gln Lys Leu Asp Thr Thr
530                 535                 540

Leu Ser Ala Ala Tyr Ala Asn Leu Asp Asn Lys Thr His Phe Glu Gly
545                 550                 555                 560

Ile Asn Ala Glu Ser Glu Pro Val Gly Ala Trp Ala Met Asn Tyr Ala
            565                 570                 575
```

-continued

```
Ser Met Ala Ile Gln Arg Arg Ala Ser Thr Gln Ser Pro Gln Gln Ser
            580                 585                 590

Trp Leu Ala Ile Ala Arg Gly Phe Ser Arg Tyr Leu Val Gly Asn Glu
            595                 600                 605

Ser Tyr Glu Asn Asn Arg Tyr Gly Arg Tyr Leu Gln Tyr Gly Gln
610                 615                 620

Leu Glu Ile Ile Pro Ala Asp Leu Thr Gln Ser Gly Phe Ser His Ala
625                 630                 635                 640

Gly Trp Asp Trp Asn Arg Tyr Pro Gly Thr Thr Ile His Leu Pro
                645                 650                 655

Tyr Asn Glu Leu Glu Ala Lys Leu Asn Gln Leu Pro Ala Ala Gly Ile
            660                 665                 670

Glu Glu Met Leu Leu Ser Thr Glu Ser Tyr Ser Gly Ala Asn Thr Leu
            675                 680                 685

Asn Asn Asn Ser Met Phe Ala Met Lys Leu His Gly His Ser Lys Tyr
690                 695                 700

Gln Gln Gln Ser Leu Arg Ala Asn Lys Ser Tyr Phe Leu Phe Asp Asn
705                 710                 715                 720

Arg Val Ile Ala Leu Gly Ser Gly Ile Glu Asn Asp Asp Lys Gln His
                725                 730                 735

Thr Thr Glu Thr Thr Leu Phe Gln Phe Ala Val Pro Lys Leu Gln Ser
            740                 745                 750

Val Ile Ile Asn Gly Lys Lys Val Asn Gln Leu Asp Thr Gln Leu Thr
            755                 760                 765

Leu Asn Asn Ala Asp Thr Leu Ile Asp Pro Ala Gly Asn Leu Tyr Lys
770                 775                 780

Leu Thr Lys Gly Gln Thr Val Lys Phe Ser Tyr Gln Lys Gln His Ser
785                 790                 795                 800

Leu Asp Asp Arg Asn Ser Lys Pro Thr Glu Gln Leu Phe Ala Thr Ala
                805                 810                 815

Val Ile Ser His Gly Lys Ala Pro Ser Asn Glu Asn Tyr Glu Tyr Ala
            820                 825                 830

Ile Ala Ile Glu Ala Gln Asn Asn Lys Ala Pro Lys Tyr Thr Val Leu
            835                 840                 845

Gln His Asn Asp Gln Leu His Ala Val Lys Asp Lys Ile Thr Gln Glu
850                 855                 860

Glu Gly Tyr Gly Phe Phe Glu Ala Thr Lys Leu Lys Ser Ala Asp Ala
865                 870                 875                 880

Thr Leu Leu Ser Ser Asp Ala Pro Val Met Val Met Ala Lys Ile Gln
                885                 890                 895

Asn Gln Gln Leu Thr Leu Ser Ile Val Asn Pro Asp Leu Asn Leu Tyr
            900                 905                 910

Gln Gly Arg Glu Lys Asp Gln Phe Asp Asp Lys Gly Asn Gln Ile Glu
            915                 920                 925

Val Ser Val Tyr Ser Arg His Trp Leu Thr Ala Glu Ser Gln Ser Thr
930                 935                 940

Asn Ser Thr Ile Thr Val Lys Gly Ile Trp Lys Leu Thr Thr Pro Gln
945                 950                 955                 960

Pro Gly Val Ile Ile Lys His His Asn Asn Thr Leu Ile Thr Thr
                965                 970                 975

Thr Thr Ile Gln Ala Thr Pro Thr Val Ile Asn Leu Val Lys
            980                 985                 990
```

<210> SEQ ID NO 27
<211> LENGTH: 2994
<212> TYPE: DNA
<213> ORGANISM: Artificial
<220> FEATURE:
<223> OTHER INFORMATION: Synthetic polynucleotide for Chondroitinase
    ABC I
<220> FEATURE:
<221> NAME/KEY: misc_feature
<222> LOCATION: (1086)..(1086)
<223> OTHER INFORMATION: n is a, c, g, or t

<400> SEQUENCE: 27

| | | | | | |
|---|---|---|---|---|---|
| gccaccagca | atcctgcatt | tgatcctaaa | aatctgatgc | agtcagaaat | ttaccatttt       60 |
| gcacaaaata | acccattagc | agacttctca | tcagataaaa | actcaatact | aacgttatct      120 |
| gataaacgta | gcattatggg | aaaccaatct | cttttatgga | aatggaaagg | tggtagtagc      180 |
| tttactttac | ataaaaaact | gattgtcccc | accgataaag | aagcatctaa | agcatgggga      240 |
| cgctcatcca | ccccgtttt  | ctcatttttgg | ctttacaatg | aaaaaccgat | tgatggttat      300 |
| cttactatcg | atttcggaga | aaaactcatt | tcaaccagtg | aggctcaggc | aggctttaaa      360 |
| gtaaaattag | atttcactgg | ctggcgtact | gtgggagtct | ctttaaataa | cgatcttgaa      420 |
| aatcgagaga | tgaccttaaa | tgcaaccaat | acctcctctg | atggtactca | agacagcatt      480 |
| gggcgttctt | taggtgctaa | agtcgatagt | attcgtttta | aagcgccttc | taatgtgagt      540 |
| cagggtgaaa | tctatatcga | ccgtattatg | ttttctgtcg | atgatgctcg | ctaccaatgg      600 |
| tctgattatc | aagtaaaaac | tcgcttatca | gaacctgaaa | ttcaatttca | aacgtaaag       660 |
| ccacaactac | ctgtaacacc | tgaaaattta | gcggccattg | atcttattcg | ccaacgtcta      720 |
| attaatgaat | ttgtcggagg | tgaaaaagag | acaaacctcg | cattagaaga | gaatatcagc      780 |
| aaattaaaaa | gtgatttcga | tgctcttaat | actcacactt | tagcaaatgg | tggaacgcaa      840 |
| ggcagacatc | tgatcactga | taaacaaatc | attatttatc | aaccagagaa | tcttaactct      900 |
| caagataaac | aactatttga | taattatgtt | attttaggta | attacacgac | attaatgttt      960 |
| aatattagcc | gtgcttatgt | gctggaaaaa | gatcccacac | aaaaggcgca | actaaagcag     1020 |
| atgtacttat | taatgacaaa | gcattattta | gatcaaggct | tgttaaagg  | gagtgcttta     1080 |
| gtgacnaccc | atcactgggg | atacagttct | cgttggtggt | atatttccac | gttattaatg     1140 |
| tctgatgcac | taaagaagc  | gaacctacaa | actcaagttt | atgattcatt | actgtggtat     1200 |
| tcacgtgagt | ttaaaagtag | ttttgatatg | aaagtaagtg | ctgatagctc | tgatctagat     1260 |
| tatttcaata | cctatctccg | ccaacattta | gccttattac | tactagagcc | tgatgatcaa     1320 |
| aagcgtatca | acttagttaa | tactttcagc | cattatatca | ctggcgcatt | aacgcaagtg     1380 |
| ccaccgggtg | gtaaagatgg | tttacgccct | gatggtacag | catggcgaca | tgaaggcaac     1440 |
| tatccgggct | actctttccc | agcctttaaa | aatgcctctc | agcttattta | tttattacgc     1500 |
| gatacaccat | tttcagtggg | tgaaagtggt | tggaatagcc | tgaaaaaagc | gatggtttca     1560 |
| gcgtggatct | acagtaatcc | agaagttgga | ttaccgcttg | caggaagaca | ccctcttaac     1620 |
| tcaccttcgt | taaatcagt  | cgctcaaggc | tattactggc | ttgccatgtc | tgcaaaatca     1680 |
| tcgcctgata | aaacacttgc | atctatttat | cttgcgatta | gtgataaaac | acaaaatgaa     1740 |
| tcaactgcta | ttttttggaga | aactattaca | ccagcgtctt | tacctcaagg | tttctatgcc     1800 |
| tttaatggcg | gtgcttttgg | tattcatcgt | tggcaagata | aaatggtgac | actgaaagct     1860 |
| tataacacca | atgtttggtc | atctgaaatt | tataacaaag | ataaccgtta | tggccgttac     1920 |
| caaagtcatg | gtgtcgctca | aatagtgagt | aatggctcgc | agctttcaca | gggctatcag     1980 |

-continued

```
caagaaggtt gggattggaa tagaatgcca ggggcaacca ctatccacct tcctcttaaa    2040
gacttagaca gtcctaaacc tcataccttta atgcaacgtg gagagcgtgg atttagcgga   2100
acatcatccc ttgaaggtca atatggcatg atggcattcg atcttattta tcccgccaat   2160
cttgagcgtt ttgatcctaa tttcactgcg aaaaagagtg tattagccgc tgataatcac   2220 ttaatttta ttggtagcaa tataaatagt agtgataaaa ataaaaatgt tgaaacgacc    2280
ttattccaac atgccattac tccaacatta aatacccttt ggattaatgg acaaaagata   2340
gaaaacatgc cttatcaaac aacacttcaa caaggtgatt ggttaattga tagcaatggc   2400
aatggttact taattactca agcagaaaaa gtaaatgtaa gtcgccaaca tcaggtttca   2460
gcggaaaata aaaatcgcca accgacagaa ggaaacttta gctcggcatg gatcgatcac   2520
agcactcgcc ccaaagatgc cagttatgag tatatggtct ttttagatgc gacacctgaa   2580
aaaatgggag agatggcaca aaaattccgt gaaaataatg ggttatatca ggttcttcgt   2640
aaggataaag acgttcatat tattctcgat aaactcagca atgtaacggg atatgccttt   2700
tatcagccag catcaattga agacaaatgg atcaaaaagg ttaataaacc tgcaattgtg   2760
atgactcatc gacaaaaaga cactcttatt gtcagtgcag ttacacctga tttaaatatg   2820
actcgccaaa aagcagcaac tcctgtcacc atcaatgtca cgattaatgg caaatggcaa   2880
tctgctgata aaaatagtga agtgaaatat caggtttctg gtgataacac tgaactgacg   2940
tttacgagtt actttggtat tccacaagaa atcaaactct cgccactccc ttga         2994
```

<210> SEQ ID NO 28
<211> LENGTH: 999
<212> TYPE: PRT
<213> ORGANISM: Artificial
<220> FEATURE:
<223> OTHER INFORMATION: Synthetic polypeptide, Chondroitinase ABC I
      protein, Xaa is any amino acid
<220> FEATURE:
<221> NAME/KEY: misc_feature
<222> LOCATION: (998)..(999)
<223> OTHER INFORMATION: Xaa can be any naturally occurring amino acid

<400> SEQUENCE: 28

```
Ala Thr Ser Asn Pro Ala Phe Asp Pro Lys Asn Leu Met Gln Ser Glu
1               5                   10                  15

Ile Tyr His Phe Ala Gln Asn Asn Pro Leu Ala Asp Phe Ser Ser Asp
            20                  25                  30

Lys Asn Ser Ile Leu Thr Leu Ser Asp Lys Arg Ser Ile Met Gly Asn
        35                  40                  45

Gln Ser Leu Leu Trp Lys Trp Lys Gly Gly Ser Ser Phe Thr Leu His
    50                  55                  60

Lys Lys Leu Ile Val Pro Thr Asp Lys Glu Ala Ser Lys Ala Trp Gly
65                  70                  75                  80

Arg Ser Ser Thr Pro Val Phe Ser Phe Trp Leu Tyr Asn Glu Lys Pro
                85                  90                  95

Ile Asp Gly Tyr Leu Thr Ile Asp Phe Gly Glu Lys Leu Ile Ser Thr
            100                 105                 110

Ser Glu Ala Gln Ala Gly Phe Lys Val Lys Leu Asp Phe Thr Gly Trp
        115                 120                 125

Arg Thr Val Gly Val Ser Leu Asn Asn Asp Leu Glu Asn Arg Glu Met
    130                 135                 140

Thr Leu Asn Ala Thr Asn Thr Ser Ser Asp Gly Thr Gln Asp Ser Ile
145                 150                 155                 160

Gly Arg Ser Leu Gly Ala Lys Val Asp Ser Ile Arg Phe Lys Ala Pro
```

```
                        165                 170                 175
Ser Asn Val Ser Gln Gly Glu Ile Tyr Ile Asp Arg Ile Met Phe Ser
                180                 185                 190
Val Asp Ala Arg Tyr Gln Trp Ser Asp Tyr Gln Val Lys Thr Arg
            195                 200                 205
Leu Ser Glu Pro Glu Ile Gln Phe His Asn Val Lys Pro Gln Leu Pro
            210                 215                 220
Val Thr Pro Glu Asn Leu Ala Ala Ile Asp Leu Ile Arg Gln Arg Leu
225                 230                 235                 240
Ile Asn Glu Phe Val Gly Gly Glu Lys Glu Thr Asn Leu Ala Leu Glu
                245                 250                 255
Glu Asn Ile Ser Lys Leu Lys Ser Asp Phe Asp Ala Leu Asn Thr His
                260                 265                 270
Thr Leu Ala Asn Gly Gly Thr Gln Gly Arg His Leu Ile Thr Asp Lys
            275                 280                 285
Gln Ile Ile Ile Tyr Gln Pro Glu Asn Leu Asn Ser Gln Asp Lys Gln
            290                 295                 300
Leu Phe Asp Asn Tyr Val Ile Leu Gly Asn Tyr Thr Thr Leu Met Phe
305                 310                 315                 320
Asn Ile Ser Arg Ala Tyr Val Leu Glu Lys Asp Pro Thr Gln Lys Ala
                325                 330                 335
Gln Leu Lys Gln Met Tyr Leu Leu Met Thr Lys His Leu Leu Asp Gln
            340                 345                 350
Gly Phe Val Lys Gly Ser Ala Leu Val Thr Thr His His Trp Gly Tyr
            355                 360                 365
Ser Ser Arg Trp Trp Tyr Ile Ser Thr Leu Leu Met Ser Asp Ala Leu
370                 375                 380
Lys Glu Ala Asn Leu Gln Thr Gln Val Tyr Asp Ser Leu Leu Trp Tyr
385                 390                 395                 400
Ser Arg Glu Phe Lys Ser Ser Phe Asp Met Lys Val Ser Ala Asp Ser
                405                 410                 415
Ser Asp Leu Asp Tyr Phe Asn Thr Leu Ser Arg Gln His Leu Ala Leu
            420                 425                 430
Leu Leu Leu Glu Pro Asp Asp Gln Lys Arg Ile Asn Leu Val Asn Thr
            435                 440                 445
Phe Ser His Tyr Ile Thr Gly Ala Leu Thr Gln Val Pro Pro Gly Gly
            450                 455                 460
Lys Asp Gly Leu Arg Pro Asp Gly Thr Ala Trp Arg His Glu Gly Asn
465                 470                 475                 480
Tyr Pro Gly Tyr Ser Phe Pro Ala Phe Lys Asn Ala Ser Gln Leu Ile
                485                 490                 495
Tyr Leu Leu Arg Asp Thr Pro Phe Ser Val Gly Glu Ser Gly Trp Asn
            500                 505                 510
Asn Leu Lys Lys Ala Met Val Ser Ala Trp Ile Tyr Ser Asn Pro Glu
            515                 520                 525
Val Gly Leu Pro Leu Ala Gly Arg His Pro Phe Asn Ser Pro Ser Leu
            530                 535                 540
Lys Ser Val Ala Gln Gly Tyr Tyr Trp Leu Ala Met Ser Ala Lys Ser
545                 550                 555                 560
Ser Pro Asp Lys Thr Leu Ala Ser Ile Tyr Leu Ala Ile Ser Asp Lys
                565                 570                 575
Thr Gln Asn Glu Ser Thr Ala Ile Phe Gly Glu Thr Ile Thr Pro Ala
                580                 585                 590
```

```
Ser Leu Pro Gln Gly Phe Tyr Ala Phe Asn Gly Gly Ala Phe Gly Ile
        595                 600                 605

His Arg Trp Gln Asp Lys Met Val Thr Leu Lys Ala Tyr Asn Thr Asn
610                 615                 620

Val Trp Ser Ser Glu Ile Tyr Asn Lys Asp Asn Arg Tyr Gly Arg Tyr
625                 630                 635                 640

Gln Ser His Gly Val Ala Gln Ile Val Ser Asn Gly Ser Gln Leu Ser
            645                 650                 655

Gln Gly Tyr Gln Gln Glu Gly Trp Asp Trp Asn Arg Met Glu Gly Ala
        660                 665                 670

Thr Thr Ile His Leu Pro Leu Lys Asp Leu Asp Ser Pro Lys Pro His
    675                 680                 685

Thr Leu Met Gln Arg Gly Glu Arg Gly Phe Ser Gly Thr Ser Ser Leu
690                 695                 700

Glu Gly Gln Tyr Gly Met Met Ala Phe Asn Leu Ile Tyr Pro Ala Asn
705                 710                 715                 720

Leu Glu Arg Phe Asp Pro Asn Phe Thr Ala Lys Lys Ser Val Leu Ala
            725                 730                 735

Ala Asp Asn His Leu Ile Phe Ile Gly Ser Asn Ile Asn Ser Ser Asp
        740                 745                 750

Lys Asn Lys Asn Val Glu Thr Thr Leu Phe Gln His Ala Ile Thr Pro
    755                 760                 765

Thr Leu Asn Thr Leu Trp Ile Asn Gly Gln Lys Ile Glu Asn Met Pro
770                 775                 780

Tyr Gln Thr Thr Leu Gln Gln Gly Asp Trp Leu Ile Asp Ser Asn Gly
785                 790                 795                 800

Asn Gly Tyr Leu Ile Thr Gln Ala Glu Lys Val Asn Val Ser Arg Gln
            805                 810                 815

His Gln Val Ser Ala Glu Asn Lys Asn Arg Gln Pro Thr Glu Gly Asn
        820                 825                 830

Phe Ser Ser Ala Trp Ile Asp His Ser Thr Arg Pro Lys Asp Ala Ser
    835                 840                 845

Tyr Glu Tyr Met Val Phe Leu Asp Ala Thr Pro Glu Lys Met Gly Glu
850                 855                 860

Met Ala Gln Lys Phe Arg Glu Asn Asn Gly Leu Tyr Gln Val Leu Arg
865                 870                 875                 880

Lys Asp Lys Asp Val His Ile Ile Leu Asp Lys Leu Ser Asn Val Thr
            885                 890                 895

Gly Tyr Ala Phe Tyr Gln Pro Ala Ser Ile Glu Asp Lys Trp Ile Lys
        900                 905                 910

Lys Val Asn Lys Pro Ala Ile Val Met Thr His Arg Gln Lys Asp Thr
    915                 920                 925

Leu Ile Val Ser Ala Val Thr Pro Asp Leu Asn Met Thr Arg Gln Lys
930                 935                 940

Ala Ala Thr Pro Val Thr Ile Asn Val Thr Ile Asn Gly Lys Trp Gln
945                 950                 955                 960

Ser Ala Asp Lys Asn Ser Glu Val Lys Tyr Gln Val Ser Gly Asp Asn
            965                 970                 975

Thr Glu Leu Thr Phe Thr Ser Tyr Phe Gly Ile Pro Gln Glu Ile Lys
        980                 985                 990

Leu Ser Pro Leu Pro Xaa Xaa
        995

<210> SEQ ID NO 29
```

-continued

```
<211> LENGTH: 405
<212> TYPE: PRT
<213> ORGANISM: Homo Sapiens

<400> SEQUENCE: 29

Met Ala Ala His Leu Leu Pro Ile Cys Ala Leu Phe Leu Thr Leu Leu
1               5                   10                  15

Asp Met Ala Gln Gly Phe Arg Gly Pro Leu Leu Pro Asn Arg Pro Phe
            20                  25                  30

Thr Thr Val Trp Asn Ala Asn Thr Gln Trp Cys Leu Glu Arg His Gly
        35                  40                  45

Val Asp Val Asp Val Ser Val Phe Asp Val Val Ala Asn Pro Gly Gln
50                  55                  60

Thr Phe Arg Gly Pro Asp Met Thr Ile Phe Tyr Ser Ser Gln Leu Gly
65                  70                  75                  80

Thr Tyr Pro Tyr Tyr Thr Pro Thr Gly Glu Pro Val Phe Gly Gly Leu
                85                  90                  95

Pro Gln Asn Ala Ser Leu Ile Ala His Leu Ala Arg Thr Phe Gln Asp
            100                 105                 110

Ile Leu Ala Ala Ile Pro Ala Pro Asp Phe Ser Gly Leu Ala Val Ile
        115                 120                 125

Asp Trp Glu Ala Trp Arg Pro Arg Trp Ala Phe Asn Trp Asp Thr Lys
    130                 135                 140

Asp Ile Tyr Arg Gln Arg Ser Arg Ala Leu Val Gln Ala Gln His Pro
145                 150                 155                 160

Asp Trp Pro Ala Pro Gln Val Glu Ala Val Ala Gln Asp Gln Phe Gln
                165                 170                 175

Gly Ala Ala Arg Ala Trp Met Ala Gly Thr Leu Gln Leu Gly Arg Ala
            180                 185                 190

Leu Arg Pro Arg Gly Leu Trp Gly Phe Tyr Gly Phe Pro Asp Cys Tyr
        195                 200                 205

Asn Tyr Asp Phe Leu Ser Pro Asn Tyr Thr Gly Gln Cys Pro Ser Gly
    210                 215                 220

Ile Arg Ala Gln Asn Asp Gln Leu Gly Trp Leu Trp Gly Gln Ser Arg
225                 230                 235                 240

Ala Leu Tyr Pro Ser Ile Tyr Met Pro Ala Val Leu Glu Gly Thr Gly
                245                 250                 255

Lys Ser Gln Met Tyr Val Gln His Arg Val Ala Glu Ala Phe Arg Val
            260                 265                 270

Ala Val Ala Ala Gly Asp Pro Asn Leu Pro Val Leu Pro Tyr Val Gln
        275                 280                 285

Ile Phe Tyr Asp Thr Thr Asn His Phe Leu Pro Leu Glu Ser Cys Gln
    290                 295                 300

Ala Ile Lys Glu Tyr Met Asp Thr Thr Leu Gly Pro Phe Ile Leu Asn
305                 310                 315                 320

Val Thr Ser Gly Ala Leu Leu Cys Ser Gln Ala Leu Cys Ser His His
                325                 330                 335

Gly Arg Cys Val Arg Arg Thr Ser His Pro Lys Ala Leu Leu Leu Leu
            340                 345                 350

Asn Pro Ala Ser Phe Ser Ile Gln Leu Thr Pro Gly Gly Gly Pro Leu
        355                 360                 365

Ser Leu Arg Gly Ala Leu Ser Leu Glu Asp Gln Ala Gln Met Ala Val
    370                 375                 380

Glu Phe Lys Cys Arg Cys Tyr Pro Gly Trp Gln Ala Pro Trp Cys Glu
385                 390                 395                 400
```

```
Arg Lys Ser Met Trp
            405

<210> SEQ ID NO 30
<211> LENGTH: 473
<212> TYPE: PRT
<213> ORGANISM: Homo Sapiens

<400> SEQUENCE: 30

Met Arg Ala Gly Pro Gly Pro Thr Val Thr Leu Ala Leu Val Leu Ala
1               5                   10                  15

Val Ser Trp Ala Met Glu Leu Lys Pro Thr Ala Pro Pro Ile Phe Thr
            20                  25                  30

Gly Arg Pro Phe Val Val Ala Trp Asp Val Pro Thr Gln Asp Cys Gly
        35                  40                  45

Pro Arg Leu Lys Val Pro Leu Asp Leu Asn Ala Phe Asp Val Gln Ala
    50                  55                  60

Ser Pro Asn Glu Gly Phe Val Asn Gln Asn Ile Thr Ile Phe Tyr Arg
65                  70                  75                  80

Asp Arg Leu Gly Leu Tyr Pro Arg Phe Asp Ser Ala Gly Arg Ser Val
                85                  90                  95

His Gly Gly Val Pro Gln Asn Val Ser Leu Trp Ala His Arg Lys Met
            100                 105                 110

Leu Gln Lys Arg Val Glu His Tyr Ile Arg Thr Gln Glu Ser Ala Gly
        115                 120                 125

Leu Ala Val Ile Asp Trp Glu Asp Trp Arg Pro Val Trp Val Arg Asn
    130                 135                 140

Trp Gln Asp Lys Asp Val Tyr Arg Arg Leu Ser Arg Gln Leu Val Ala
145                 150                 155                 160

Ser Arg His Pro Asp Trp Pro Pro Asp Arg Ile Val Lys Gln Ala Gln
                165                 170                 175

Tyr Glu Phe Glu Phe Ala Ala Gln Gln Phe Met Leu Glu Thr Leu Arg
            180                 185                 190

Tyr Val Lys Ala Val Arg Pro Arg His Leu Trp Gly Phe Tyr Leu Phe
        195                 200                 205

Pro Asp Cys Tyr Asn His Asp Tyr Val Gln Asn Trp Glu Ser Tyr Thr
    210                 215                 220

Gly Arg Cys Pro Asp Val Glu Val Ala Arg Asn Asp Gln Leu Ala Trp
225                 230                 235                 240

Leu Trp Ala Glu Ser Thr Ala Leu Phe Pro Ser Val Tyr Leu Asp Glu
                245                 250                 255

Thr Leu Ala Ser Ser Arg His Gly Arg Asn Phe Val Ser Phe Arg Val
            260                 265                 270

Gln Glu Ala Leu Arg Val Ala Arg Thr His His Ala Asn His Ala Leu
        275                 280                 285

Pro Val Tyr Val Phe Thr Arg Pro Thr Tyr Ser Arg Arg Leu Thr Gly
    290                 295                 300

Leu Ser Glu Met Asp Leu Ile Ser Thr Ile Gly Glu Ser Ala Ala Leu
305                 310                 315                 320

Gly Ala Ala Gly Val Ile Leu Trp Gly Asp Ala Gly Tyr Thr Thr Ser
                325                 330                 335

Thr Glu Thr Cys Gln Tyr Leu Lys Asp Tyr Leu Thr Arg Leu Leu Val
            340                 345                 350

Pro Tyr Val Val Asn Val Ser Trp Ala Thr Gln Tyr Cys Ser Arg Ala
        355                 360                 365
```

```
Gln Cys His Gly His Gly Arg Cys Val Arg Arg Asn Pro Ser Ala Ser
    370                 375                 380

Thr Phe Leu His Leu Ser Thr Asn Ser Phe Arg Leu Val Pro Gly His
385                 390                 395                 400

Ala Pro Gly Glu Pro Gln Leu Arg Pro Val Gly Glu Leu Ser Trp Ala
                405                 410                 415

Asp Ile Asp His Leu Gln Thr His Phe Arg Cys Gln Cys Tyr Leu Gly
            420                 425                 430

Trp Ser Gly Glu Gln Cys Gln Trp Asp His Arg Gln Ala Ala Gly Gly
        435                 440                 445

Ala Ser Glu Ala Trp Ala Gly Ser His Leu Thr Ser Leu Leu Ala Leu
    450                 455                 460

Ala Ala Leu Ala Phe Thr Trp Thr Leu
465                 470

<210> SEQ ID NO 31
<211> LENGTH: 417
<212> TYPE: PRT
<213> ORGANISM: Homo Sapiens

<400> SEQUENCE: 31

Met Thr Thr Gln Leu Gly Pro Ala Leu Val Leu Gly Val Ala Leu Cys
1               5                   10                  15

Leu Gly Cys Gly Gln Pro Leu Pro Gln Val Pro Glu Arg Pro Phe Ser
                20                  25                  30

Val Leu Trp Asn Val Pro Ser Ala His Cys Glu Ala Arg Phe Gly Val
            35                  40                  45

His Leu Pro Leu Asn Ala Leu Gly Ile Ile Ala Asn Arg Gly Gln His
        50                  55                  60

Phe His Gly Gln Asn Met Thr Ile Phe Tyr Lys Asn Gln Leu Gly Leu
65                  70                  75                  80

Tyr Pro Tyr Phe Gly Pro Arg Gly Thr Ala His Asn Gly Gly Ile Pro
                85                  90                  95

Gln Ala Leu Pro Leu Asp Arg His Leu Ala Leu Ala Ala Tyr Gln Ile
                100                 105                 110

His His Ser Leu Arg Pro Gly Phe Ala Gly Pro Ala Val Leu Asp Trp
            115                 120                 125

Glu Glu Trp Cys Pro Leu Trp Ala Gly Asn Trp Gly Arg Arg Arg Ala
130                 135                 140

Tyr Gln Ala Ala Ser Trp Ala Trp Ala Gln Val Phe Pro Asp Leu
145                 150                 155                 160

Asp Pro Gln Glu Gln Leu Tyr Lys Ala Tyr Thr Gly Phe Glu Gln Ala
                165                 170                 175

Ala Arg Ala Leu Met Glu Asp Thr Leu Arg Val Ala Gln Ala Leu Arg
            180                 185                 190

Pro His Gly Leu Trp Gly Phe Tyr His Tyr Pro Ala Cys Gly Asn Gly
        195                 200                 205

Trp His Ser Met Ala Ser Asn Tyr Thr Gly Arg Cys His Ala Ala Thr
    210                 215                 220

Leu Ala Arg Asn Thr Gln Leu His Trp Leu Trp Ala Ala Ser Ser Ala
225                 230                 235                 240

Leu Phe Pro Ser Ile Tyr Leu Pro Pro Arg Leu Pro Pro Ala His His
                245                 250                 255

Gln Ala Phe Val Arg His Arg Leu Glu Glu Ala Phe Arg Val Ala Leu
            260                 265                 270
```

```
Val Gly His Arg His Pro Leu Pro Val Leu Ala Tyr Val Arg Leu Thr
            275                 280                 285

His Arg Arg Ser Gly Arg Phe Leu Ser Gln Asp Asp Leu Val Gln Ser
290                 295                 300

Ile Gly Val Ser Ala Ala Leu Gly Ala Ala Gly Val Val Leu Trp Gly
305                 310                 315                 320

Asp Leu Ser Leu Ser Ser Glu Glu Glu Cys Trp His Leu His Asp
            325                 330                 335

Tyr Leu Val Asp Thr Leu Gly Pro Tyr Val Ile Asn Val Thr Arg Ala
            340                 345                 350

Ala Met Ala Cys Ser His Gln Arg Cys His Gly His Gly Arg Cys Ala
            355                 360                 365

Arg Arg Asp Pro Gly Gln Met Glu Ala Phe Leu His Leu Trp Pro Asp
            370                 375                 380

Gly Ser Leu Gly Asp Trp Lys Ser Phe Ser Cys His Cys Tyr Trp Gly
385                 390                 395                 400

Trp Ala Gly Pro Thr Cys Gln Glu Pro Arg Pro Gly Pro Lys Glu Ala
                405                 410                 415

Val

<210> SEQ ID NO 32
<211> LENGTH: 481
<212> TYPE: PRT
<213> ORGANISM: Homo Sapiens

<400> SEQUENCE: 32

Met Lys Val Leu Ser Glu Gly Gln Leu Lys Leu Cys Val Val Gln Pro
1               5                   10                  15

Val His Leu Thr Ser Trp Leu Leu Ile Phe Phe Ile Leu Lys Ser Ile
            20                  25                  30

Ser Cys Leu Lys Pro Ala Arg Leu Pro Ile Tyr Gln Arg Lys Pro Phe
            35                  40                  45

Ile Ala Ala Trp Asn Ala Pro Thr Asp Gln Cys Leu Ile Lys Tyr Asn
50                  55                  60

Leu Arg Leu Asn Leu Lys Met Phe Pro Val Ile Gly Ser Pro Leu Ala
65                  70                  75                  80

Lys Ala Arg Gly Gln Asn Val Thr Ile Phe Tyr Val Asn Arg Leu Gly
                85                  90                  95

Tyr Tyr Pro Trp Tyr Thr Ser Gln Gly Val Pro Ile Asn Gly Gly Leu
                100                 105                 110

Pro Gln Asn Ile Ser Leu Gln Val His Leu Glu Lys Ala Asp Gln Asp
            115                 120                 125

Ile Asn Tyr Tyr Ile Pro Ala Glu Asp Phe Ser Gly Leu Ala Val Ile
            130                 135                 140

Asp Trp Glu Tyr Trp Arg Pro Gln Trp Ala Arg Asn Trp Asn Ser Lys
145                 150                 155                 160

Asp Val Tyr Arg Gln Lys Ser Arg Lys Leu Ile Ser Asp Met Gly Lys
                165                 170                 175

Asn Val Ser Ala Thr Asp Ile Glu Tyr Leu Ala Lys Val Thr Phe Glu
                180                 185                 190

Glu Ser Ala Lys Ala Phe Met Lys Glu Thr Ile Lys Leu Gly Ile Lys
            195                 200                 205

Ser Arg Pro Lys Gly Leu Trp Gly Tyr Tyr Leu Tyr Pro Asp Cys His
210                 215                 220
```

-continued

Asn Tyr Asn Val Tyr Ala Pro Asn Tyr Ser Gly Ser Cys Pro Glu Asp
225                 230                 235                 240

Glu Val Leu Arg Asn Asn Glu Leu Ser Trp Leu Trp Asn Ser Ser Ala
            245                 250                 255

Ala Leu Tyr Pro Ser Ile Cys Val Trp Lys Ser Leu Gly Asp Ser Glu
        260                 265                 270

Asn Ile Leu Arg Phe Ser Lys Phe Arg Val His Glu Ser Met Arg Ile
    275                 280                 285

Ser Thr Met Thr Ser His Asp Tyr Ala Leu Pro Val Phe Val Tyr Thr
290                 295                 300

Arg Leu Gly Tyr Arg Asp Glu Pro Leu Phe Phe Leu Ser Lys Gln Asp
305                 310                 315                 320

Leu Val Ser Thr Ile Gly Glu Ser Ala Ala Leu Gly Ala Ala Gly Ile
            325                 330                 335

Val Ile Trp Gly Asp Met Asn Leu Thr Ala Ser Lys Ala Asn Cys Thr
        340                 345                 350

Lys Val Lys Gln Phe Val Ser Ser Asp Leu Gly Ser Tyr Ile Ala Asn
    355                 360                 365

Val Thr Arg Ala Ala Glu Val Cys Ser Leu His Leu Cys Arg Asn Asn
370                 375                 380

Gly Arg Cys Ile Arg Lys Met Trp Asn Ala Pro Ser Tyr Leu His Leu
385                 390                 395                 400

Asn Pro Ala Ser Tyr His Ile Glu Ala Ser Glu Asp Gly Glu Phe Thr
            405                 410                 415

Val Lys Gly Lys Ala Ser Asp Thr Asp Leu Ala Val Met Ala Asp Thr
        420                 425                 430

Phe Ser Cys His Cys Tyr Gln Gly Tyr Glu Gly Ala Asp Cys Arg Glu
    435                 440                 445

Ile Lys Thr Ala Asp Gly Cys Ser Gly Val Ser Pro Ser Pro Gly Ser
450                 455                 460

Leu Met Thr Leu Cys Leu Leu Leu Ala Ser Tyr Arg Ser Ile Gln
465                 470                 475                 480

Leu

<210> SEQ ID NO 33
<211> LENGTH: 509
<212> TYPE: PRT
<213> ORGANISM: Homo Sapiens

<400> SEQUENCE: 33

Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Pro
        35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
            85                  90                  95

Gly Tyr Tyr Pro Tyr Ile Asp Ser Ile Thr Gly Val Thr Val Asn Gly
        100                 105                 110

Gly Ile Pro Gln Lys Ile Ser Leu Gln Asp His Leu Asp Lys Ala Lys

```
              115                 120                 125
Lys Asp Ile Thr Phe Tyr Met Pro Val Asp Asn Leu Gly Met Ala Val
    130                 135                 140
Ile Asp Trp Glu Glu Trp Arg Pro Thr Trp Ala Arg Asn Trp Lys Pro
145                 150                 155                 160
Lys Asp Val Tyr Lys Asn Arg Ser Ile Glu Leu Val Gln Gln Gln Asn
                165                 170                 175
Val Gln Leu Ser Leu Thr Glu Ala Thr Glu Lys Ala Lys Gln Glu Phe
            180                 185                 190
Glu Lys Ala Gly Lys Asp Phe Leu Val Glu Thr Ile Lys Leu Gly Lys
        195                 200                 205
Leu Leu Arg Pro Asn His Leu Trp Gly Tyr Tyr Leu Phe Pro Asp Cys
    210                 215                 220
Tyr Asn His His Tyr Lys Lys Pro Gly Tyr Asn Gly Ser Cys Phe Asn
225                 230                 235                 240
Val Glu Ile Lys Arg Asn Asp Asp Leu Ser Trp Leu Trp Asn Glu Ser
                245                 250                 255
Thr Ala Leu Tyr Pro Ser Ile Tyr Leu Asn Thr Gln Gln Ser Pro Val
            260                 265                 270
Ala Ala Thr Leu Tyr Val Arg Asn Arg Val Arg Glu Ala Ile Arg Val
        275                 280                 285
Ser Lys Ile Pro Asp Ala Lys Ser Pro Leu Pro Val Phe Ala Tyr Thr
    290                 295                 300
Arg Ile Val Phe Thr Asp Gln Val Leu Lys Phe Leu Ser Gln Asp Glu
305                 310                 315                 320
Leu Val Tyr Thr Phe Gly Glu Thr Val Ala Leu Gly Ala Ser Gly Ile
                325                 330                 335
Val Ile Trp Gly Thr Leu Ser Ile Met Arg Ser Met Lys Ser Cys Leu
            340                 345                 350
Leu Leu Asp Asn Tyr Met Glu Thr Ile Leu Asn Pro Tyr Ile Ile Asn
        355                 360                 365
Val Thr Leu Ala Ala Lys Met Cys Ser Gln Val Leu Cys Gln Glu Gln
    370                 375                 380
Gly Val Cys Ile Arg Lys Asn Trp Asn Ser Ser Asp Tyr Leu His Leu
385                 390                 395                 400
Asn Pro Asp Asn Phe Ala Ile Gln Leu Glu Lys Gly Gly Lys Phe Thr
                405                 410                 415
Val Arg Gly Lys Pro Thr Leu Glu Asp Leu Glu Gln Phe Ser Glu Lys
            420                 425                 430
Phe Tyr Cys Ser Cys Tyr Ser Thr Leu Ser Cys Lys Glu Lys Ala Asp
        435                 440                 445
Val Lys Asp Thr Asp Ala Val Asp Val Cys Ile Ala Asp Gly Val Cys
    450                 455                 460
Ile Asp Ala Phe Leu Lys Pro Pro Met Glu Thr Glu Glu Pro Gln Ile
465                 470                 475                 480
Phe Tyr Asn Ala Ser Pro Ser Thr Leu Ser Ala Thr Met Phe Ile Val
                485                 490                 495
Ser Ile Leu Phe Leu Ile Ile Ser Ser Val Ala Ser Leu
            500                 505

<210> SEQ ID NO 34
<211> LENGTH: 11
<212> TYPE: PRT
<213> ORGANISM: Artificial
<220> FEATURE:
```

-continued

<223> OTHER INFORMATION: Synthetic polypeptide, amino acid sequence for
      a TAT peptide

<400> SEQUENCE: 34

Tyr Gly Arg Lys Lys Arg Arg Gln Arg Arg Arg
1               5                   10

<210> SEQ ID NO 35
<211> LENGTH: 1021
<212> TYPE: PRT
<213> ORGANISM: Artificial
<220> FEATURE:
<223> OTHER INFORMATION: Synthetic polypeptide, amino acid sequence for
      a TAT peptide

<400> SEQUENCE: 35

Met Pro Ile Phe Arg Phe Thr Ala Leu Ala Met Thr Leu Gly Leu Leu
1               5                   10                  15

Ser Ala Pro Tyr Asn Ala Met Ala Ala Thr Ser Asn Pro Ala Phe Asp
            20                  25                  30

Pro Lys Asn Leu Met Gln Ser Glu Ile Tyr His Phe Ala Gln Asn Asn
        35                  40                  45

Pro Leu Ala Asp Phe Ser Ser Asp Lys Asn Ser Ile Leu Thr Leu Ser
    50                  55                  60

Asp Lys Arg Ser Ile Met Gly Asn Gln Ser Leu Leu Trp Lys Trp Lys
65                  70                  75                  80

Gly Gly Ser Ser Phe Thr Leu His Lys Lys Leu Ile Val Pro Thr Asp
                85                  90                  95

Lys Glu Ala Ser Lys Ala Trp Gly Arg Ser Ser Thr Pro Val Phe Ser
            100                 105                 110

Phe Trp Leu Tyr Asn Glu Lys Pro Ile Asp Gly Tyr Leu Thr Ile Asp
        115                 120                 125

Phe Gly Glu Lys Leu Ile Ser Thr Ser Glu Ala Gln Ala Gly Phe Lys
    130                 135                 140

Val Lys Leu Asp Phe Thr Gly Trp Arg Ala Val Gly Val Ser Leu Asn
145                 150                 155                 160

Asn Asp Leu Glu Asn Arg Glu Met Thr Leu Asn Ala Thr Asn Thr Ser
                165                 170                 175

Ser Asp Gly Thr Gln Asp Ser Ile Gly Arg Ser Leu Gly Ala Lys Val
            180                 185                 190

Asp Ser Ile Arg Phe Lys Ala Pro Ser Asn Val Ser Gln Gly Glu Ile
        195                 200                 205

Tyr Ile Asp Arg Ile Met Phe Ser Val Asp Asp Ala Arg Tyr Gln Trp
    210                 215                 220

Ser Asp Tyr Gln Val Lys Thr Arg Leu Ser Pro Glu Ile Gln Phe
225                 230                 235                 240

His Asn Val Lys Pro Gln Leu Pro Val Thr Pro Glu Asn Leu Ala Ala
                245                 250                 255

Ile Asp Leu Ile Arg Gln Arg Leu Ile Asn Glu Phe Val Gly Gly Glu
            260                 265                 270

Lys Glu Thr Asn Leu Ala Leu Glu Glu Asn Ile Ser Lys Leu Lys Ser
        275                 280                 285

Asp Phe Asp Ala Leu Asn Ile His Thr Leu Ala Asn Gly Gly Thr Gln
    290                 295                 300

Gly Arg His Leu Ile Thr Asp Lys Gln Ile Ile Tyr Gln Pro Glu
305                 310                 315                 320

Asn Leu Asn Ser Gln Asp Lys Gln Leu Phe Asp Asn Tyr Val Ile Leu

-continued

```
                325                 330                 335
Gly Asn Tyr Thr Thr Leu Met Phe Asn Ile Ser Arg Ala Tyr Val Leu
            340                 345                 350
Glu Lys Asp Pro Thr Gln Lys Ala Gln Leu Lys Gln Met Tyr Leu Leu
                355                 360                 365
Met Thr Lys His Leu Leu Asp Gln Gly Phe Val Lys Gly Ser Ala Leu
        370                 375                 380
Val Thr Thr His His Trp Gly Tyr Ser Ser Arg Trp Trp Tyr Ile Ser
385                 390                 395                 400
Thr Leu Leu Met Ser Asp Ala Leu Lys Glu Ala Asn Leu Gln Thr Gln
                405                 410                 415
Val Tyr Asp Ser Leu Leu Trp Tyr Ser Arg Glu Phe Lys Ser Ser Phe
            420                 425                 430
Asp Met Lys Val Ser Ala Asp Ser Asp Leu Asp Tyr Phe Asn Thr
                435                 440                 445
Leu Ser Arg Gln His Leu Ala Leu Leu Leu Glu Pro Asp Asp Gln
    450                 455                 460
Lys Arg Ile Asn Leu Val Asn Thr Phe Ser His Tyr Ile Thr Gly Ala
465                 470                 475                 480
Leu Thr Gln Val Pro Pro Gly Lys Asp Gly Leu Arg Pro Asp Gly
                485                 490                 495
Thr Ala Trp Arg Ala Glu Gly Asn Tyr Pro Gly Ala Ser Phe Pro Ala
                500                 505                 510
Phe Lys Asn Ala Ser Gln Leu Ile Tyr Leu Leu Arg Asp Thr Pro Phe
                515                 520                 525
Ser Val Gly Glu Ser Gly Trp Asn Asn Leu Lys Lys Ala Met Val Ser
            530                 535                 540
Ala Trp Ile Tyr Ser Asn Pro Glu Val Gly Leu Pro Leu Ala Gly Arg
545                 550                 555                 560
His Pro Phe Asn Ser Pro Ser Leu Lys Ser Val Ala Gln Gly Tyr Tyr
                565                 570                 575
Trp Leu Ala Met Ser Ala Lys Ser Ser Pro Asp Lys Thr Leu Ala Ser
                580                 585                 590
Ile Tyr Leu Ala Ile Ser Asp Lys Thr Gln Asn Glu Ser Thr Ala Ile
            595                 600                 605
Phe Gly Glu Thr Ile Thr Pro Ala Ser Leu Pro Gln Gly Phe Tyr Ala
        610                 615                 620
Phe Asn Gly Gly Ala Phe Gly Ile His Arg Trp Gln Asp Lys Met Val
625                 630                 635                 640
Thr Leu Lys Ala Tyr Asn Thr Asn Val Trp Ser Ser Glu Ile Tyr Asn
                645                 650                 655
Lys Asp Asn Arg Tyr Gly Arg Tyr Gln Ser His Gly Val Ala Gln Ile
                660                 665                 670
Val Ser Asn Gly Ser Gln Leu Ser Gln Gly Tyr Gln Gln Glu Gly Trp
            675                 680                 685
Asp Trp Asn Arg Met Glu Gly Ala Thr Thr Ile His Leu Pro Leu Lys
        690                 695                 700
Asp Leu Asp Ser Pro Lys Pro His Thr Leu Met Gln Arg Gly Glu Arg
705                 710                 715                 720
Gly Phe Ser Gly Thr Ser Ser Leu Glu Gly Gln Tyr Gly Met Met Ala
                725                 730                 735
Phe Asn Leu Ile Tyr Pro Ala Asn Leu Glu Arg Phe Asp Pro Asn Phe
            740                 745                 750
```

```
Thr Ala Lys Lys Ser Val Leu Ala Ala Asp Asn His Leu Ile Phe Ile
            755                 760                 765

Gly Ser Asn Ile Asn Ser Ser Asp Lys Asn Lys Asn Val Glu Thr Thr
        770                 775                 780

Leu Phe Gln His Ala Ile Thr Pro Thr Leu Asn Thr Leu Trp Ile Asn
785                 790                 795                 800

Gly Gln Lys Ile Glu Asn Met Pro Tyr Gln Thr Thr Leu Gln Gln Gly
                805                 810                 815

Asp Trp Leu Ile Asp Ser Asn Gly Asn Gly Tyr Leu Ile Thr Gln Ala
                820                 825                 830

Glu Lys Val Asn Val Ser Arg Gln His Gln Val Ser Ala Glu Asn Lys
                835                 840                 845

Asn Arg Gln Pro Thr Glu Gly Asn Phe Ser Ser Ala Trp Ile Asp His
            850                 855                 860

Ser Thr Arg Pro Lys Asp Ala Ser Tyr Glu Tyr Met Val Phe Leu Asp
865                 870                 875                 880

Ala Thr Pro Glu Lys Met Gly Glu Met Ala Gln Lys Phe Arg Glu Asn
                885                 890                 895

Asn Gly Leu Tyr Gln Val Leu Arg Lys Asp Lys Asp Val His Ile Ile
                900                 905                 910

Leu Asp Lys Leu Ser Asn Val Thr Gly Tyr Ala Phe Tyr Gln Pro Ala
                915                 920                 925

Ser Ile Glu Asp Lys Trp Ile Lys Lys Val Asn Lys Pro Ala Ile Val
            930                 935                 940

Met Thr His Arg Gln Lys Asp Thr Leu Ile Val Ser Ala Val Thr Pro
945                 950                 955                 960

Asp Leu Asn Met Thr Arg Gln Lys Ala Ala Thr Pro Val Thr Ile Asn
                965                 970                 975

Val Thr Ile Asn Gly Lys Trp Gln Ser Ala Asp Lys Asn Ser Glu Val
                980                 985                 990

Lys Tyr Gln Val Ser Gly Asp Asn  Thr Glu Leu Thr Phe  Thr Ser Tyr
            995                 1000                1005

Phe Gly Ile Pro Gln Glu Ile  Lys Leu Ser Pro Leu  Pro
    1010                1015                1020

<210> SEQ ID NO 36
<211> LENGTH: 1021
<212> TYPE: PRT
<213> ORGANISM: Proteus Vulgaris

<400> SEQUENCE: 36

Met Pro Ile Phe Arg Phe Thr Ala Leu Ala Met Thr Leu Gly Leu Leu
1               5                   10                  15

Ser Ala Pro Tyr Asn Ala Met Ala Ala Thr Ser Asn Pro Ala Phe Asp
                20                  25                  30

Pro Lys Asn Leu Met Gln Ser Glu Ile Tyr His Phe Ala Gln Asn Asn
        35                  40                  45

Pro Leu Ala Asp Phe Ser Ser Asp Lys Asn Ser Ile Leu Thr Leu Ser
    50                  55                  60

Asp Lys Arg Ser Ile Met Gly Asn Gln Ser Leu Leu Trp Lys Trp Lys
65                  70                  75                  80

Gly Gly Ser Ser Phe Thr Leu His Lys Lys Leu Ile Val Pro Thr Asp
                85                  90                  95

Lys Glu Ala Ser Lys Ala Trp Gly Arg Ser Ser Thr Pro Val Phe Ser
                100                 105                 110
```

```
Phe Trp Leu Tyr Asn Glu Lys Pro Ile Asp Gly Tyr Leu Thr Ile Asp
            115                 120                 125
Phe Gly Glu Lys Leu Ile Ser Thr Ser Glu Ala Gln Ala Gly Phe Lys
        130                 135                 140
Val Lys Leu Asp Phe Thr Gly Trp Arg Ala Val Gly Val Ser Leu Asn
145                 150                 155                 160
Asn Asp Leu Glu Asn Arg Glu Met Thr Leu Asn Ala Thr Asn Thr Ser
                165                 170                 175
Ser Asp Gly Thr Gln Asp Ser Ile Gly Arg Ser Leu Gly Ala Lys Val
            180                 185                 190
Asp Ser Ile Arg Phe Lys Ala Pro Ser Asn Val Ser Gln Gly Glu Ile
        195                 200                 205
Tyr Ile Asp Arg Ile Met Phe Ser Val Asp Asp Ala Arg Tyr Gln Trp
210                 215                 220
Ser Asp Tyr Gln Val Lys Thr Arg Leu Ser Glu Pro Glu Ile Gln Phe
225                 230                 235                 240
His Asn Val Lys Pro Gln Leu Pro Val Thr Pro Glu Asn Leu Ala Ala
                245                 250                 255
Ile Asp Leu Ile Arg Gln Arg Leu Ile Asn Glu Phe Val Gly Gly Glu
            260                 265                 270
Lys Glu Thr Asn Leu Ala Leu Glu Glu Asn Ile Ser Lys Leu Lys Ser
        275                 280                 285
Asp Phe Asp Ala Leu Asn Ile His Thr Leu Ala Asn Gly Gly Thr Gln
290                 295                 300
Gly Arg His Leu Ile Thr Asp Lys Gln Ile Ile Tyr Gln Pro Glu
305                 310                 315                 320
Asn Leu Asn Ser Gln Asp Lys Gln Leu Phe Asp Asn Tyr Val Ile Leu
                325                 330                 335
Gly Asn Tyr Thr Thr Leu Met Phe Asn Ile Ser Arg Ala Tyr Val Leu
            340                 345                 350
Glu Lys Asp Pro Thr Gln Lys Ala Gln Leu Lys Gln Met Tyr Leu Leu
        355                 360                 365
Met Thr Lys His Leu Leu Asp Gln Gly Phe Val Lys Gly Ser Ala Leu
370                 375                 380
Val Thr Thr His His Trp Gly Tyr Ser Ser Arg Trp Trp Tyr Ile Ser
385                 390                 395                 400
Thr Leu Leu Met Ser Asp Ala Leu Lys Glu Ala Asn Leu Gln Thr Gln
                405                 410                 415
Val Tyr Asp Ser Leu Leu Trp Tyr Ser Arg Glu Phe Lys Ser Ser Phe
            420                 425                 430
Asp Met Lys Val Ser Ala Asp Ser Asp Leu Asp Tyr Phe Asn Thr
        435                 440                 445
Leu Ser Arg Gln His Leu Ala Leu Leu Leu Glu Pro Asp Asp Gln
450                 455                 460
Lys Arg Ile Asn Leu Val Asn Thr Phe Ser His Tyr Ile Thr Gly Ala
465                 470                 475                 480
Leu Thr Gln Val Pro Pro Gly Gly Lys Asp Gly Leu Arg Pro Asp Gly
                485                 490                 495
Thr Ala Trp Arg His Glu Gly Asn Tyr Pro Gly Tyr Ser Phe Pro Ala
            500                 505                 510
Phe Lys Asn Ala Ser Gln Leu Ile Tyr Leu Leu Arg Asp Thr Pro Phe
        515                 520                 525
Ser Val Gly Glu Ser Gly Trp Asn Asn Leu Lys Lys Ala Met Val Ser
530                 535                 540
```

```
Ala Trp Ile Tyr Ser Asn Pro Glu Val Gly Leu Pro Leu Ala Gly Arg
545                 550                 555                 560

His Pro Phe Asn Ser Pro Ser Leu Lys Ser Val Ala Gln Gly Tyr Tyr
                565                 570                 575

Trp Leu Ala Met Ser Ala Lys Ser Ser Pro Asp Lys Thr Leu Ala Ser
                    580                 585                 590

Ile Tyr Leu Ala Ile Ser Asp Lys Thr Gln Asn Glu Ser Thr Ala Ile
                595                 600                 605

Phe Gly Glu Thr Ile Thr Pro Ala Ser Leu Pro Gln Gly Phe Tyr Ala
            610                 615                 620

Phe Asn Gly Gly Ala Phe Gly Ile His Arg Trp Gln Asp Lys Met Val
625                 630                 635                 640

Thr Leu Lys Ala Tyr Asn Thr Asn Val Trp Ser Ser Glu Ile Tyr Asn
                645                 650                 655

Lys Asp Asn Arg Tyr Gly Arg Tyr Gln Ser His Gly Val Ala Gln Ile
                660                 665                 670

Val Ser Asn Gly Ser Gln Leu Ser Gln Gly Tyr Gln Gln Glu Gly Trp
                675                 680                 685

Asp Trp Asn Arg Met Glu Gly Ala Thr Thr Ile His Leu Pro Leu Lys
            690                 695                 700

Asp Leu Asp Ser Pro Lys Pro His Thr Leu Met Gln Arg Gly Glu Arg
705                 710                 715                 720

Gly Phe Ser Gly Thr Ser Ser Leu Glu Gly Gln Tyr Gly Met Met Ala
                    725                 730                 735

Phe Asn Leu Ile Tyr Pro Ala Asn Leu Glu Arg Phe Asp Pro Asn Phe
                740                 745                 750

Thr Ala Lys Lys Ser Val Leu Ala Ala Asp Asn His Leu Ile Phe Ile
                755                 760                 765

Gly Ser Asn Ile Asn Ser Ser Asp Lys Asn Lys Asn Val Glu Thr Thr
            770                 775                 780

Leu Phe Gln His Ala Ile Thr Pro Thr Leu Asn Thr Leu Trp Ile Asn
785                 790                 795                 800

Gly Gln Lys Ile Glu Asn Met Pro Tyr Gln Thr Thr Leu Gln Gln Gly
                    805                 810                 815

Asp Trp Leu Ile Asp Ser Asn Gly Asn Gly Tyr Leu Ile Thr Gln Ala
                820                 825                 830

Glu Lys Val Asn Val Ser Arg Gln His Gln Val Ser Ala Glu Asn Lys
            835                 840                 845

Asn Arg Gln Pro Thr Glu Gly Asn Phe Ser Ser Ala Trp Ile Asp His
850                 855                 860

Ser Thr Arg Pro Lys Asp Ala Ser Tyr Glu Tyr Met Val Phe Leu Asp
865                 870                 875                 880

Ala Thr Pro Glu Lys Met Gly Glu Met Ala Gln Lys Phe Arg Glu Asn
                    885                 890                 895

Asn Gly Leu Tyr Gln Val Leu Arg Lys Asp Lys Asp Val His Ile Ile
                900                 905                 910

Leu Asp Lys Leu Ser Asn Val Thr Gly Tyr Ala Phe Tyr Gln Pro Ala
            915                 920                 925

Ser Ile Glu Asp Lys Trp Ile Lys Lys Val Asn Lys Pro Ala Ile Val
                930                 935                 940

Met Thr His Arg Gln Lys Asp Thr Leu Ile Val Ser Ala Val Thr Pro
945                 950                 955                 960

Asp Leu Asn Met Thr Arg Gln Lys Ala Ala Thr Pro Val Thr Ile Asn
```

```
                           965                 970                 975
Val Thr Ile Asn Gly Lys Trp Gln Ser Ala Asp Lys Asn Ser Glu Val
            980                 985                 990

Lys Tyr Gln Val Ser Gly Asp Asn Thr Glu Leu Thr Phe Thr Ser Tyr
            995                1000                1005

Phe Gly Ile Pro Gln Glu Ile Lys Leu Ser Pro Leu Pro
           1010                1015                1020

<210> SEQ ID NO 37
<211> LENGTH: 977
<212> TYPE: PRT
<213> ORGANISM: Artificial
<220> FEATURE:
<223> OTHER INFORMATION: Synthetic polypeptide, N(delta)20 ABC I of
      Proteus Vulgaris

<400> SEQUENCE: 37

Ala Gln Asn Asn Pro Leu Ala Asp Phe Ser Ser Asp Lys Asn Ser Ile
1               5                  10                  15

Leu Thr Leu Ser Asp Lys Arg Ser Ile Met Gly Asn Gln Ser Leu Leu
            20                  25                  30

Trp Lys Trp Lys Gly Gly Ser Ser Phe Thr Leu His Lys Lys Leu Ile
        35                  40                  45

Val Pro Thr Asp Lys Glu Ala Ser Lys Ala Trp Gly Arg Ser Ser Thr
    50                  55                  60

Pro Val Phe Ser Phe Trp Leu Tyr Asn Glu Lys Pro Ile Asp Gly Tyr
65                  70                  75                  80

Leu Thr Ile Asp Phe Gly Glu Lys Leu Ile Ser Thr Ser Glu Ala Gln
                85                  90                  95

Ala Gly Phe Lys Val Lys Leu Asp Phe Thr Gly Trp Arg Ala Val Gly
            100                 105                 110

Val Ser Leu Asn Asn Asp Leu Glu Asn Arg Glu Met Thr Leu Asn Ala
        115                 120                 125

Thr Asn Thr Ser Ser Asp Gly Thr Gln Asp Ser Ile Gly Arg Ser Leu
    130                 135                 140

Gly Ala Lys Val Asp Ser Ile Arg Phe Lys Ala Pro Ser Asn Val Ser
145                 150                 155                 160

Gln Gly Glu Ile Tyr Ile Asp Arg Ile Met Phe Ser Val Asp Asp Ala
                165                 170                 175

Arg Tyr Gln Trp Ser Asp Tyr Gln Val Lys Thr Arg Leu Ser Glu Pro
            180                 185                 190

Glu Ile Gln Phe His Asn Val Lys Pro Gln Leu Pro Val Thr Pro Glu
        195                 200                 205

Asn Leu Ala Ala Ile Asp Leu Ile Arg Gln Arg Leu Ile Asn Glu Phe
    210                 215                 220

Val Gly Gly Glu Lys Glu Thr Asn Leu Ala Leu Glu Glu Asn Ile Ser
225                 230                 235                 240

Lys Leu Lys Ser Asp Phe Asp Ala Leu Asn Ile His Thr Leu Ala Asn
                245                 250                 255

Gly Gly Thr Gln Gly Arg His Leu Ile Thr Asp Lys Gln Ile Ile
            260                 265                 270

Tyr Gln Pro Glu Asn Leu Asn Ser Gln Asp Lys Gln Leu Phe Asp Asn
        275                 280                 285

Tyr Val Ile Leu Gly Asn Tyr Thr Thr Leu Met Phe Asn Ile Ser Arg
    290                 295                 300

Ala Tyr Val Leu Glu Lys Asp Pro Thr Gln Lys Ala Gln Leu Lys Gln
```

```
                    305                 310                 315                 320
              Met Tyr Leu Leu Met Thr Lys His Leu Asp Gln Gly Phe Val Lys
                              325                 330                 335

Gly Ser Ala Leu Val Thr Thr His His Trp Gly Tyr Ser Ser Arg Trp
                              340                 345                 350

Trp Tyr Ile Ser Thr Leu Leu Met Ser Asp Ala Leu Lys Glu Ala Asn
                              355                 360                 365

Leu Gln Thr Gln Val Tyr Asp Ser Leu Leu Trp Tyr Ser Arg Glu Phe
                  370                 375                 380

Lys Ser Ser Phe Asp Met Lys Val Ser Ala Asp Ser Ser Asp Leu Asp
              385                 390                 395                 400

Tyr Phe Asn Thr Leu Ser Arg Gln His Leu Ala Leu Leu Leu Glu
                              405                 410                 415

Pro Asp Asp Gln Lys Arg Ile Asn Leu Val Asn Thr Phe Ser His Tyr
                              420                 425                 430

Ile Thr Gly Ala Leu Thr Gln Val Pro Pro Gly Gly Lys Asp Gly Leu
                              435                 440                 445

Arg Pro Asp Gly Thr Ala Trp Arg His Glu Gly Asn Tyr Pro Gly Tyr
              450                 455                 460

Ser Phe Pro Ala Phe Lys Asn Ala Ser Gln Leu Ile Tyr Leu Leu Arg
              465                 470                 475                 480

Asp Thr Pro Phe Ser Val Gly Glu Ser Gly Trp Asn Asn Leu Lys Lys
                              485                 490                 495

Ala Met Val Ser Ala Trp Ile Tyr Ser Asn Pro Glu Val Gly Leu Pro
                              500                 505                 510

Leu Ala Gly Arg His Pro Phe Asn Ser Pro Ser Leu Lys Ser Val Ala
                              515                 520                 525

Gln Gly Tyr Tyr Trp Leu Ala Met Ser Ala Lys Ser Ser Pro Asp Lys
                              530                 535                 540

Thr Leu Ala Ser Ile Tyr Leu Ala Ile Ser Asp Lys Thr Gln Asn Glu
              545                 550                 555                 560

Ser Thr Ala Ile Phe Gly Glu Thr Ile Thr Pro Ala Ser Leu Pro Gln
                              565                 570                 575

Gly Phe Tyr Ala Phe Asn Gly Gly Ala Phe Gly Ile His Arg Trp Gln
                              580                 585                 590

Asp Lys Met Val Thr Leu Lys Ala Tyr Asn Thr Asn Val Trp Ser Ser
                              595                 600                 605

Glu Ile Tyr Asn Lys Asp Asn Arg Tyr Gly Arg Tyr Gln Ser His Gly
                  610                 615                 620

Val Ala Gln Ile Val Ser Asn Gly Ser Gln Leu Ser Gln Gly Tyr Gln
              625                 630                 635                 640

Gln Glu Gly Trp Asp Trp Asn Arg Met Glu Gly Ala Thr Thr Ile His
                              645                 650                 655

Leu Pro Leu Lys Asp Leu Asp Ser Pro Lys Pro His Thr Leu Met Gln
                              660                 665                 670

Arg Gly Glu Arg Gly Phe Ser Gly Thr Ser Ser Leu Glu Gly Gln Tyr
                              675                 680                 685

Gly Met Met Ala Phe Asn Leu Ile Tyr Pro Ala Asn Leu Glu Arg Phe
                              690                 695                 700

Asp Pro Asn Phe Thr Ala Lys Lys Ser Val Leu Ala Ala Asp Asn His
              705                 710                 715                 720

Leu Ile Phe Ile Gly Ser Asn Ile Asn Ser Ser Asp Lys Asn Lys Asn
                              725                 730                 735
```

```
Val Glu Thr Thr Leu Phe Gln His Ala Ile Thr Pro Thr Leu Asn Thr
            740                 745                 750

Leu Trp Ile Asn Gly Gln Lys Ile Glu Asn Met Pro Tyr Gln Thr Thr
            755                 760                 765

Leu Gln Gln Gly Asp Trp Leu Ile Asp Ser Asn Gly Asn Gly Tyr Leu
            770                 775                 780

Ile Thr Gln Ala Glu Lys Val Asn Val Ser Arg Gln His Gln Val Ser
785                 790                 795                 800

Ala Glu Asn Lys Asn Arg Gln Pro Thr Glu Gly Asn Phe Ser Ser Ala
                805                 810                 815

Trp Ile Asp His Ser Thr Arg Pro Lys Asp Ala Ser Tyr Glu Tyr Met
            820                 825                 830

Val Phe Leu Asp Ala Thr Pro Glu Lys Met Gly Glu Met Ala Gln Lys
            835                 840                 845

Phe Arg Glu Asn Asn Gly Leu Tyr Gln Val Leu Arg Lys Asp Lys Asp
            850                 855                 860

Val His Ile Ile Leu Asp Lys Leu Ser Asn Val Thr Gly Tyr Ala Phe
865                 870                 875                 880

Tyr Gln Pro Ala Ser Ile Glu Asp Lys Trp Ile Lys Lys Val Asn Lys
                885                 890                 895

Pro Ala Ile Val Met Thr His Arg Gln Lys Asp Thr Leu Ile Val Ser
            900                 905                 910

Ala Val Thr Pro Asp Leu Asn Met Thr Arg Gln Lys Ala Ala Thr Pro
            915                 920                 925

Val Thr Ile Asn Val Thr Ile Asn Gly Lys Trp Gln Ser Ala Asp Lys
            930                 935                 940

Asn Ser Glu Val Lys Tyr Gln Val Ser Gly Asp Asn Thr Glu Leu Thr
945                 950                 955                 960

Phe Thr Ser Tyr Phe Gly Ile Pro Gln Glu Ile Lys Leu Ser Pro Leu
                965                 970                 975

Pro

<210> SEQ ID NO 38
<211> LENGTH: 937
<212> TYPE: PRT
<213> ORGANISM: Artificial
<220> FEATURE:
<223> OTHER INFORMATION: Synthetic polypeptide, N(delta)60 ABC I Protein

<400> SEQUENCE: 38

Phe Thr Leu His Lys Lys Leu Ile Val Pro Thr Asp Lys Glu Ala Ser
1               5                   10                  15

Lys Ala Trp Gly Arg Ser Ser Thr Pro Val Phe Ser Phe Trp Leu Tyr
            20                  25                  30

Asn Glu Lys Pro Ile Asp Gly Tyr Leu Thr Ile Asp Phe Gly Glu Lys
            35                  40                  45

Leu Ile Ser Thr Ser Glu Ala Gln Ala Gly Phe Lys Val Lys Leu Asp
            50                  55                  60

Phe Thr Gly Trp Arg Ala Val Gly Val Ser Leu Asn Asn Asp Leu Glu
65                  70                  75                  80

Asn Arg Glu Met Thr Leu Asn Ala Thr Asn Thr Ser Ser Asp Gly Thr
                85                  90                  95

Gln Asp Ser Ile Gly Arg Ser Leu Gly Ala Lys Val Asp Ser Ile Arg
            100                 105                 110

Phe Lys Ala Pro Ser Asn Val Ser Gln Gly Glu Ile Tyr Ile Asp Arg
            115                 120                 125
```

```
Ile Met Phe Ser Val Asp Asp Ala Arg Tyr Gln Trp Ser Asp Tyr Gln
    130                 135                 140
Val Lys Thr Arg Leu Ser Glu Pro Glu Ile Gln Phe His Asn Val Lys
145                 150                 155                 160
Pro Gln Leu Pro Val Thr Pro Glu Asn Leu Ala Ala Ile Asp Leu Ile
                165                 170                 175
Arg Gln Arg Leu Ile Asn Glu Phe Val Gly Gly Glu Lys Glu Thr Asn
            180                 185                 190
Leu Ala Leu Glu Glu Asn Ile Ser Lys Leu Lys Ser Asp Phe Asp Ala
        195                 200                 205
Leu Asn Ile His Thr Leu Ala Asn Gly Gly Thr Gln Gly Arg His Leu
    210                 215                 220
Ile Thr Asp Lys Gln Ile Ile Tyr Gln Pro Glu Asn Leu Asn Ser
225                 230                 235                 240
Gln Asp Lys Gln Leu Phe Asp Asn Tyr Val Ile Leu Gly Asn Tyr Thr
                245                 250                 255
Thr Leu Met Phe Asn Ile Ser Arg Ala Tyr Val Leu Glu Lys Asp Pro
            260                 265                 270
Thr Gln Lys Ala Gln Leu Lys Gln Met Tyr Leu Leu Met Thr Lys His
        275                 280                 285
Leu Leu Asp Gln Gly Phe Val Lys Gly Ser Ala Leu Val Thr Thr His
    290                 295                 300
His Trp Gly Tyr Ser Ser Arg Trp Trp Tyr Ile Ser Thr Leu Leu Met
305                 310                 315                 320
Ser Asp Ala Leu Lys Glu Ala Asn Leu Gln Thr Gln Val Tyr Asp Ser
                325                 330                 335
Leu Leu Trp Tyr Ser Arg Glu Phe Lys Ser Ser Phe Asp Met Lys Val
            340                 345                 350
Ser Ala Asp Ser Ser Asp Leu Asp Tyr Phe Asn Thr Leu Ser Arg Gln
        355                 360                 365
His Leu Ala Leu Leu Leu Glu Pro Asp Asp Gln Lys Arg Ile Asn
    370                 375                 380
Leu Val Asn Thr Phe Ser His Tyr Ile Thr Gly Ala Leu Thr Gln Val
385                 390                 395                 400
Pro Pro Gly Gly Lys Asp Gly Leu Arg Pro Asp Gly Thr Ala Trp Arg
                405                 410                 415
His Glu Gly Asn Tyr Pro Gly Tyr Ser Phe Pro Ala Phe Lys Asn Ala
            420                 425                 430
Ser Gln Leu Ile Tyr Leu Leu Arg Asp Thr Pro Phe Ser Val Gly Glu
        435                 440                 445
Ser Gly Trp Asn Asn Leu Lys Lys Ala Met Val Ser Ala Trp Ile Tyr
    450                 455                 460
Ser Asn Pro Glu Val Gly Leu Pro Leu Ala Gly Arg His Pro Phe Asn
465                 470                 475                 480
Ser Pro Ser Leu Lys Ser Val Ala Gln Gly Tyr Tyr Trp Leu Ala Met
                485                 490                 495
Ser Ala Lys Ser Ser Pro Asp Lys Thr Leu Ala Ser Ile Tyr Leu Ala
            500                 505                 510
Ile Ser Asp Lys Thr Gln Asn Glu Ser Thr Ala Ile Phe Gly Glu Thr
        515                 520                 525
Ile Thr Pro Ala Ser Leu Pro Gln Gly Phe Tyr Ala Phe Asn Gly Gly
    530                 535                 540
Ala Phe Gly Ile His Arg Trp Gln Asp Lys Met Val Thr Leu Lys Ala
```

```
                545                 550                 555                 560
Tyr Asn Thr Asn Val Trp Ser Ser Glu Ile Tyr Asn Lys Asp Asn Arg
                565                 570                 575

Tyr Gly Arg Tyr Gln Ser His Gly Val Ala Gln Ile Val Ser Asn Gly
            580                 585                 590

Ser Gln Leu Ser Gln Gly Tyr Gln Gln Glu Gly Trp Asp Trp Asn Arg
        595                 600                 605

Met Glu Gly Ala Thr Thr Ile His Leu Pro Leu Lys Asp Leu Asp Ser
    610                 615                 620

Pro Lys Pro His Thr Leu Met Gln Arg Gly Glu Arg Gly Phe Ser Gly
625                 630                 635                 640

Thr Ser Ser Leu Glu Gly Gln Tyr Gly Met Met Ala Phe Asn Leu Ile
                645                 650                 655

Tyr Pro Ala Asn Leu Glu Arg Phe Asp Pro Asn Phe Thr Ala Lys Lys
            660                 665                 670

Ser Val Leu Ala Ala Asp Asn His Leu Ile Phe Ile Gly Ser Asn Ile
        675                 680                 685

Asn Ser Ser Asp Lys Asn Lys Asn Val Glu Thr Thr Leu Phe Gln His
    690                 695                 700

Ala Ile Thr Pro Thr Leu Asn Thr Leu Trp Ile Asn Gly Gln Lys Ile
705                 710                 715                 720

Glu Asn Met Pro Tyr Gln Thr Thr Leu Gln Gln Gly Asp Trp Leu Ile
                725                 730                 735

Asp Ser Asn Gly Asn Gly Tyr Leu Ile Thr Gln Ala Glu Lys Val Asn
            740                 745                 750

Val Ser Arg Gln His Gln Val Ser Ala Glu Asn Lys Asn Arg Gln Pro
        755                 760                 765

Thr Glu Gly Asn Phe Ser Ser Ala Trp Ile Asp His Ser Thr Arg Pro
    770                 775                 780

Lys Asp Ala Ser Tyr Glu Tyr Met Val Phe Leu Asp Ala Thr Pro Glu
785                 790                 795                 800

Lys Met Gly Glu Met Ala Gln Lys Phe Arg Glu Asn Asn Gly Leu Tyr
                805                 810                 815

Gln Val Leu Arg Lys Asp Lys Asp Val His Ile Ile Leu Asp Lys Leu
            820                 825                 830

Ser Asn Val Thr Gly Tyr Ala Phe Tyr Gln Pro Ala Ser Ile Glu Asp
        835                 840                 845

Lys Trp Ile Lys Lys Val Asn Lys Pro Ala Ile Val Met Thr His Arg
850                 855                 860

Gln Lys Asp Thr Leu Ile Val Ser Ala Val Thr Pro Asp Leu Asn Met
865                 870                 875                 880

Thr Arg Gln Lys Ala Ala Thr Pro Val Thr Ile Asn Val Thr Ile Asn
                885                 890                 895

Gly Lys Trp Gln Ser Ala Asp Lys Asn Ser Glu Val Lys Tyr Gln Val
            900                 905                 910

Ser Gly Asp Asn Thr Glu Leu Thr Phe Thr Ser Tyr Phe Gly Ile Pro
        915                 920                 925

Gln Glu Ile Lys Leu Ser Pro Leu Pro
    930                 935

<210> SEQ ID NO 39
<211> LENGTH: 858
<212> TYPE: PRT
<213> ORGANISM: Artificial
<220> FEATURE:
```

<223> OTHER INFORMATION: Synthetic polypeptide, N(delta)60 C(delta)80
      chondroitinase ABC I having gwra and dalni sequences

<400> SEQUENCE: 39

```
Phe Thr Leu His Lys Lys Leu Ile Val Pro Thr Asp Lys Glu Ala Ser
1               5                   10                  15

Lys Ala Trp Gly Arg Ser Ser Thr Pro Val Phe Ser Phe Trp Leu Tyr
            20                  25                  30

Asn Glu Lys Pro Ile Asp Gly Tyr Leu Thr Ile Asp Phe Gly Glu Lys
        35                  40                  45

Leu Ile Ser Thr Ser Glu Ala Gln Ala Gly Phe Lys Val Lys Leu Asp
    50                  55                  60

Phe Thr Gly Trp Arg Ala Val Gly Val Ser Leu Asn Asn Asp Leu Glu
65                  70                  75                  80

Asn Arg Glu Met Thr Leu Asn Ala Thr Asn Thr Ser Ser Asp Gly Thr
                85                  90                  95

Gln Asp Ser Ile Gly Arg Ser Leu Gly Ala Lys Val Asp Ser Ile Arg
            100                 105                 110

Phe Lys Ala Pro Ser Asn Val Ser Gln Gly Glu Ile Tyr Ile Asp Arg
        115                 120                 125

Ile Met Phe Ser Val Asp Asp Ala Arg Tyr Gln Trp Ser Asp Tyr Gln
    130                 135                 140

Val Lys Thr Arg Leu Ser Glu Pro Glu Ile Gln Phe His Asn Val Lys
145                 150                 155                 160

Pro Gln Leu Pro Val Thr Pro Glu Asn Leu Ala Ala Ile Asp Leu Ile
                165                 170                 175

Arg Gln Arg Leu Ile Asn Glu Phe Val Gly Gly Glu Lys Glu Thr Asn
            180                 185                 190

Leu Ala Leu Glu Glu Asn Ile Ser Lys Leu Lys Ser Asp Phe Asp Ala
        195                 200                 205

Leu Asn Ile His Thr Leu Ala Asn Gly Gly Thr Gln Gly Arg His Leu
    210                 215                 220

Ile Thr Asp Lys Gln Ile Ile Tyr Gln Pro Glu Asn Leu Asn Ser
225                 230                 235                 240

Gln Asp Lys Gln Leu Phe Asp Asn Tyr Val Ile Leu Gly Asn Tyr Thr
                245                 250                 255

Thr Leu Met Phe Asn Ile Ser Arg Ala Tyr Val Leu Glu Lys Asp Pro
            260                 265                 270

Thr Gln Lys Ala Gln Leu Lys Gln Met Tyr Leu Leu Met Thr Lys His
        275                 280                 285

Leu Leu Asp Gln Gly Phe Val Lys Gly Ser Ala Leu Val Thr Thr His
    290                 295                 300

His Trp Gly Tyr Ser Ser Arg Trp Trp Tyr Ile Ser Thr Leu Leu Met
305                 310                 315                 320

Ser Asp Ala Leu Lys Glu Ala Asn Leu Gln Thr Gln Val Tyr Asp Ser
                325                 330                 335

Leu Leu Trp Tyr Ser Arg Glu Phe Lys Ser Ser Phe Asp Met Lys Val
            340                 345                 350

Ser Ala Asp Ser Ser Asp Leu Asp Tyr Phe Asn Thr Leu Ser Arg Gln
        355                 360                 365

His Leu Ala Leu Leu Leu Glu Pro Asp Asp Gln Lys Arg Ile Asn
    370                 375                 380

Leu Val Asn Thr Phe Ser His Tyr Ile Thr Gly Ala Leu Thr Gln Val
385                 390                 395                 400
```

```
Pro Pro Gly Gly Lys Asp Gly Leu Arg Pro Asp Gly Thr Ala Trp Arg
            405                 410                 415

His Glu Gly Asn Tyr Pro Gly Tyr Ser Phe Pro Ala Phe Lys Asn Ala
        420                 425                 430

Ser Gln Leu Ile Tyr Leu Leu Arg Asp Thr Pro Phe Ser Val Gly Glu
    435                 440                 445

Ser Gly Trp Asn Asn Leu Lys Lys Ala Met Val Ser Ala Trp Ile Tyr
450                 455                 460

Ser Asn Pro Glu Val Gly Leu Pro Leu Ala Gly Arg His Pro Phe Asn
465                 470                 475                 480

Ser Pro Ser Leu Lys Ser Val Ala Gln Gly Tyr Tyr Trp Leu Ala Met
            485                 490                 495

Ser Ala Lys Ser Ser Pro Asp Lys Thr Leu Ala Ser Ile Tyr Leu Ala
            500                 505                 510

Ile Ser Asp Lys Thr Gln Asn Glu Ser Thr Ala Ile Phe Gly Glu Thr
        515                 520                 525

Ile Thr Pro Ala Ser Leu Pro Gln Gly Phe Tyr Ala Phe Asn Gly Gly
        530                 535                 540

Ala Phe Gly Ile His Arg Trp Gln Asp Lys Met Val Thr Leu Lys Ala
545                 550                 555                 560

Tyr Asn Thr Asn Val Trp Ser Ser Glu Ile Tyr Asn Lys Asp Asn Arg
                565                 570                 575

Tyr Gly Arg Tyr Gln Ser His Gly Val Ala Gln Ile Val Ser Asn Gly
            580                 585                 590

Ser Gln Leu Ser Gln Gly Tyr Gln Gln Glu Gly Trp Asp Trp Asn Arg
            595                 600                 605

Met Glu Gly Ala Thr Thr Ile His Leu Pro Leu Lys Asp Leu Asp Ser
    610                 615                 620

Pro Lys Pro His Thr Leu Met Gln Arg Gly Glu Arg Gly Phe Ser Gly
625                 630                 635                 640

Thr Ser Ser Leu Glu Gly Gln Tyr Gly Met Met Ala Phe Asn Leu Ile
            645                 650                 655

Tyr Pro Ala Asn Leu Glu Arg Phe Asp Pro Asn Phe Thr Ala Lys Lys
            660                 665                 670

Ser Val Leu Ala Ala Asp Asn His Leu Ile Phe Ile Gly Ser Asn Ile
    675                 680                 685

Asn Ser Ser Asp Lys Asn Lys Asn Val Glu Thr Thr Leu Phe Gln His
    690                 695                 700

Ala Ile Thr Pro Thr Leu Asn Thr Leu Trp Ile Asn Gly Gln Lys Ile
705                 710                 715                 720

Glu Asn Met Pro Tyr Gln Thr Thr Leu Gln Gln Gly Asp Trp Leu Ile
                725                 730                 735

Asp Ser Asn Gly Asn Gly Tyr Leu Ile Thr Gln Ala Glu Lys Val Asn
            740                 745                 750

Val Ser Arg Gln His Gln Val Ser Ala Glu Asn Lys Asn Arg Gln Pro
            755                 760                 765

Thr Glu Gly Asn Phe Ser Ser Ala Trp Ile Asp His Ser Thr Arg Pro
    770                 775                 780

Lys Asp Ala Ser Tyr Glu Tyr Met Val Phe Leu Asp Ala Thr Pro Glu
785                 790                 795                 800

Lys Met Gly Glu Met Ala Gln Lys Phe Arg Glu Asn Asn Gly Leu Tyr
            805                 810                 815

Gln Val Leu Arg Lys Asp Lys Asp Val His Ile Ile Leu Asp Lys Leu
        820                 825                 830
```

```
Ser Asn Val Thr Gly Tyr Ala Phe Tyr Gln Pro Ala Ser Ile Glu Asp
        835                 840                 845

Lys Trp Ile Lys Lys Val Asn Lys Pro Ala
    850                 855

<210> SEQ ID NO 40
<211> LENGTH: 2976
<212> TYPE: DNA
<213> ORGANISM: Artificial
<220> FEATURE:
<223> OTHER INFORMATION: Synthetic polynucleotide, TAT-chondroitinase
      ABC I N(delta)20 nucleic acid
<220> FEATURE:
<221> NAME/KEY: misc_feature
<222> LOCATION: (1068)..(1068)
<223> OTHER INFORMATION: n is a, c, g, or t

<400> SEQUENCE: 40
ggtcgtaaaa agcgtcgtca acgtcgtcgt cctcctcaat gcgcacaaaa taacccatta      60
gcagacttct catcagataa aaactcaata ctaacgttat ctgataaacg tagcattatg     120
ggaaaccaat ctctttttatg gaaatggaaa ggtggtagta gctttacttt acataaaaaa    180
ctgattgtcc ccaccgataa agaagcatct aaagcatggg gacgctcatc caccccgtt     240 ttctcatttt ggctttacaa tgaaaaaccg attgatggtt atcttactat cgatttcgga    300
gaaaaactca tttcaaccag tgaggctcag gcaggcttta agtaaaatt agatttcact    360 ggctggcgta ctgtgggagt ctctttaaat aacgatcttg aaaatcgaga gatgacctta    420
aatgcaacca ataccctcct tgatggtact caagacagca ttgggcgttc tttaggtgct    480
aaagtcgata gtattcgttt taaagcgcct tctaatgtga gtcagggtga aatctatatc    540
gaccgtatta tgttttctgt cgatgatgct cgctaccaat ggtctgatta tcaagtaaaa    600
actcgcttat cagaacctga aattcaattt cacaacgtaa agccacaact acctgtaaca    660
cctgaaaatt tagcggccat tgatcttatt cgccaacgtc taattaatga atttgtcgga    720
ggtgaaaaag agacaaacct cgcattagaa gagaatatca gcaaattaaa aagtgatttc    780
gatgctctta atactcacac tttagcaaat ggtggaacgc aaggcagaca tctgatcact    840
gataaacaaa tcattatttta tcaaccagag aatcttaact ctcaagataa acaactattt    900
gataattatg ttatttttagg taattacacg acattaatgt ttaatattag ccgtgcttat    960
gtgctggaaa aagatcccac acaaaaggcg caactaaagc agatgtactt attaatgaca   1020
aagcatttat tagatcaagg ctttgttaaa gggagtgctt tagtgacnac ccatcactgg   1080
ggatacagtt ctcgttggtg gtatatttcc acgttattaa tgtctgatgc actaaaagaa   1140
gcgaacctac aaactcaagt ttatgattca ttactgtggt attcacgtga gtttaaagt    1200 agttttgata tgaaagtaag tgctgatagc tctgatctag attatttcaa taccttatct   1260
cgccaacatt tagccttatt actactagag cctgatgatc aaaagcgtat caacttagtt   1320
aatactttca gccattatat cactggcgca ttaacgcaag tgccaccggg tggtaaagat   1380
ggtttacgcc ctgatggtac agcatggcga catgaaggca actatccggg ctactctttc   1440
ccagccttta aaaatgcctc tcagcttatt tatttattac gcgatacacc atttcagtg    1500 ggtgaaagtg gttggaatag cctgaaaaaa gcgatggttt cagcgtggat ctacagtaat   1560
ccagaagttg gattaccgct tgcaggaaga caccctctta actcaccttc gttaaaatca   1620
gtcgctcaag gctattactg gcttgccatg tctgcaaaat catcgcctga taaaacactt   1680
gcatctattt atcttgcgat tagtgataaa acacaaaatg aatcaactgc tattttttgga   1740
```

```
gaaactatta caccagcgtc tttacctcaa ggtttctatg cctttaatgg cggtgctttt   1800
ggtattcatc gttggcaaga taaaatggtg acactgaaag cttataacac caatgtttgg   1860
tcatctgaaa tttataacaa agataaccgt tatggccgtt accaaagtca tggtgtcgct   1920
caaatagtga gtaatggctc gcagctttca cagggctatc agcaagaagg ttgggattgg   1980
aatagaatgc cagggcaac cactatccac cttcctctta aagacttaga cagtcctaaa   2040
cctcatacct taatgcaacg tggagagcgt ggatttagcg aacatcatc ccttgaaggt   2100 caatatggca tgatggcatt cgatcttatt tatcccgcca atcttgagcg ttttgatcct   2160
aatttcactg cgaaaaagag tgtattagcc gctgataatc acttaatttt tattggtagc   2220
aatataaata gtagtgataa aaataaaaat gttgaaacga ccttattcca acatgccatt   2280
actccaacat taaatacccT ttggattaat ggacaaaaga tagaaaacat gccttatcaa   2340
acaacacttc aacaaggtga ttggttaatt gatagcaatg gcaatggtta cttaattact   2400
caagcagaaa aagtaaatgt aagtcgccaa catcaggttt cagcggaaaa taaaaatcgc   2460
caaccgacag aaggaaactt tagctcggca tggatcgatc acagcactcg ccccaaagat   2520
gccagttatg agtatatggt cttttttagat gcgacacctg aaaaaatggg agagatggca   2580
caaaaattcc gtgaaaataa tgggttatat caggttcttc gtaaggataa agacgttcat   2640
attattctcg ataaactcag caatgtaacg ggatatgcct tttatcagcc agcatcaatt   2700
gaagacaaat ggatcaaaaa ggttaataaa cctgcaattg tgatgactca tcgacaaaaa   2760
gacactctta ttgtcagtgc agttacacct gatttaaata tgactcgcca aaaagcagca   2820
actcctgtca ccatcaatgt cacgattaat ggcaaatggc aatctgctga taaaaatagt   2880
gaagtgaaat atcaggtttc tggtgataac actgaactga cgtttacgag ttactttggt   2940
attccacaag aaatcaaact ctcgccactc ccttga                             2976
```

<210> SEQ ID NO 41
<211> LENGTH: 991
<212> TYPE: PRT
<213> ORGANISM: Artificial
<220> FEATURE:
<223> OTHER INFORMATION: Synthetic polypeptide, HIV-1 TAT chondroitinase
       ABC I-N(delta)20 fusion polypeptiode

<400> SEQUENCE: 41

Gly Arg Lys Lys Arg Arg Gln Arg Arg Arg Pro Pro Gln Cys Ala Gln
1               5                   10                  15

Asn Asn Pro Leu Ala Asp Phe Ser Ser Asp Lys Asn Ser Ile Leu Thr
            20                  25                  30

Leu Ser Asp Lys Arg Ser Ile Met Gly Asn Gln Ser Leu Leu Trp Lys
        35                  40                  45

Trp Lys Gly Gly Ser Ser Phe Thr Leu His Lys Lys Leu Ile Val Pro
    50                  55                  60

Thr Asp Lys Glu Ala Ser Lys Ala Trp Gly Arg Ser Ser Thr Pro Val
65                  70                  75                  80

Phe Ser Phe Trp Leu Tyr Asn Glu Lys Pro Ile Asp Gly Tyr Leu Thr
                85                  90                  95

Ile Asp Phe Gly Glu Lys Leu Ile Ser Thr Ser Glu Ala Gln Ala Gly
            100                 105                 110

Phe Lys Val Lys Leu Asp Phe Thr Gly Trp Arg Thr Val Gly Val Ser
        115                 120                 125

Leu Asn Asn Asp Leu Glu Asn Arg Glu Met Thr Leu Asn Ala Thr Asn
    130                 135                 140

```
Thr Ser Ser Asp Gly Thr Gln Asp Ser Ile Gly Arg Ser Leu Gly Ala
145                 150                 155                 160

Lys Val Asp Ser Ile Arg Phe Lys Ala Pro Ser Asn Val Ser Gln Gly
                165                 170                 175

Glu Ile Tyr Ile Asp Arg Ile Met Phe Ser Val Asp Asp Ala Arg Tyr
            180                 185                 190

Gln Trp Ser Asp Tyr Gln Val Lys Thr Arg Leu Ser Glu Pro Glu Ile
        195                 200                 205

Gln Phe His Asn Val Lys Pro Gln Leu Pro Val Thr Pro Glu Asn Leu
    210                 215                 220

Ala Ala Ile Asp Leu Ile Arg Gln Arg Leu Ile Asn Glu Phe Val Gly
225                 230                 235                 240

Gly Glu Lys Glu Thr Asn Leu Ala Leu Glu Glu Asn Ile Ser Lys Leu
                245                 250                 255

Lys Ser Asp Phe Asp Ala Leu Asn Thr His Thr Leu Ala Asn Gly Gly
                260                 265                 270

Thr Gln Gly Arg His Leu Ile Thr Asp Lys Gln Ile Ile Tyr Gln
            275                 280                 285

Pro Glu Asn Leu Asn Ser Gln Asp Lys Gln Leu Phe Asp Asn Tyr Val
290                 295                 300

Ile Leu Gly Asn Tyr Thr Thr Leu Met Phe Asn Ile Ser Arg Ala Tyr
305                 310                 315                 320

Val Leu Glu Lys Asp Pro Thr Gln Lys Ala Gln Leu Lys Gln Met Tyr
                325                 330                 335

Leu Leu Met Thr Lys His Leu Leu Asp Gln Gly Phe Val Lys Gly Ser
            340                 345                 350

Ala Leu Val Thr Thr His His Trp Gly Tyr Ser Ser Arg Trp Trp Tyr
            355                 360                 365

Ile Ser Thr Leu Leu Met Ser Asp Ala Leu Lys Glu Ala Asn Leu Gln
370                 375                 380

Thr Gln Val Tyr Asp Ser Leu Leu Trp Tyr Ser Arg Glu Phe Lys Ser
385                 390                 395                 400

Ser Phe Asp Met Lys Val Ser Ala Asp Ser Ser Asp Leu Asp Tyr Phe
                405                 410                 415

Asn Thr Leu Ser Arg Gln His Leu Ala Leu Leu Leu Glu Pro Asp
                420                 425                 430

Asp Gln Lys Arg Ile Asn Leu Val Asn Thr Phe Ser His Tyr Ile Thr
            435                 440                 445

Gly Ala Leu Thr Gln Val Pro Pro Gly Gly Lys Asp Gly Leu Arg Pro
450                 455                 460

Asp Gly Thr Ala Trp Arg His Glu Gly Asn Tyr Pro Gly Tyr Ser Phe
465                 470                 475                 480

Pro Ala Phe Lys Asn Ala Ser Gln Leu Ile Tyr Leu Leu Arg Asp Thr
                485                 490                 495

Pro Phe Ser Val Gly Glu Ser Gly Trp Asn Ser Leu Lys Lys Ala Met
                500                 505                 510

Val Ser Ala Trp Ile Tyr Ser Asn Pro Glu Val Gly Leu Pro Leu Ala
                515                 520                 525

Gly Arg His Pro Leu Asn Ser Pro Ser Leu Lys Ser Val Ala Gln Gly
            530                 535                 540

Tyr Tyr Trp Leu Ala Met Ser Ala Lys Ser Ser Pro Asp Lys Thr Leu
545                 550                 555                 560

Ala Ser Ile Tyr Leu Ala Ile Ser Asp Lys Thr Gln Asn Glu Ser Thr
                565                 570                 575
```

```
Ala Ile Phe Gly Glu Thr Ile Thr Pro Ala Ser Leu Pro Gln Gly Phe
            580                 585                 590

Tyr Ala Phe Asn Gly Gly Ala Phe Gly Ile His Arg Trp Gln Asp Lys
        595                 600                 605

Met Val Thr Leu Lys Ala Tyr Asn Thr Asn Val Trp Ser Ser Glu Ile
    610                 615                 620

Tyr Asn Lys Asp Asn Arg Tyr Gly Arg Tyr Gln Ser His Gly Val Ala
625                 630                 635                 640

Gln Ile Val Ser Asn Gly Ser Gln Leu Ser Gln Gly Tyr Gln Gln Glu
            645                 650                 655

Gly Trp Asp Trp Asn Arg Met Pro Gly Ala Thr Thr Ile His Leu Pro
        660                 665                 670

Leu Lys Asp Leu Asp Ser Pro Lys Pro His Thr Leu Met Gln Arg Gly
    675                 680                 685

Glu Arg Gly Phe Ser Gly Thr Ser Ser Leu Glu Gly Gln Tyr Gly Met
690                 695                 700

Met Ala Phe Asp Leu Ile Tyr Pro Ala Asn Leu Glu Arg Phe Asp Pro
705                 710                 715                 720

Asn Phe Thr Ala Lys Lys Ser Val Leu Ala Ala Asp Asn His Leu Ile
                725                 730                 735

Phe Ile Gly Ser Asn Ile Asn Ser Ser Asp Lys Asn Lys Asn Val Glu
            740                 745                 750

Thr Thr Leu Phe Gln His Ala Ile Thr Pro Thr Leu Asn Thr Leu Trp
        755                 760                 765

Ile Asn Gly Gln Lys Ile Glu Asn Met Pro Tyr Gln Thr Thr Leu Gln
    770                 775                 780

Gln Gly Asp Trp Leu Ile Asp Ser Asn Gly Asn Gly Tyr Leu Ile Thr
785                 790                 795                 800

Gln Ala Glu Lys Val Asn Val Ser Arg Gln His Gln Val Ser Ala Glu
                805                 810                 815

Asn Lys Asn Arg Gln Pro Thr Glu Gly Asn Phe Ser Ser Ala Trp Ile
            820                 825                 830

Asp His Ser Thr Arg Pro Lys Asp Ala Ser Tyr Glu Tyr Met Val Phe
        835                 840                 845

Leu Asp Ala Thr Pro Glu Lys Met Gly Glu Met Ala Gln Lys Phe Arg
    850                 855                 860

Glu Asn Asn Gly Leu Tyr Gln Val Leu Arg Lys Asp Lys Asp Val His
865                 870                 875                 880

Ile Ile Leu Asp Lys Leu Ser Asn Val Thr Gly Tyr Ala Phe Tyr Gln
                885                 890                 895

Pro Ala Ser Ile Glu Asp Lys Trp Ile Lys Lys Val Asn Lys Pro Ala
            900                 905                 910

Ile Val Met Thr His Arg Gln Lys Asp Thr Leu Ile Val Ser Ala Val
        915                 920                 925

Thr Pro Asp Leu Asn Met Thr Arg Gln Lys Ala Ala Thr Pro Val Thr
    930                 935                 940

Ile Asn Val Thr Ile Asn Gly Lys Trp Gln Ser Ala Asp Lys Asn Ser
945                 950                 955                 960

Glu Val Lys Tyr Gln Val Ser Gly Asp Asn Thr Glu Leu Thr Phe Thr
                965                 970                 975

Ser Tyr Phe Gly Ile Pro Gln Glu Ile Lys Leu Ser Pro Leu Pro
            980                 985                 990
```

```
<210> SEQ ID NO 42
<211> LENGTH: 2856
<212> TYPE: DNA
<213> ORGANISM: Artificial
<220> FEATURE:
<223> OTHER INFORMATION: Synthetic polynucleotide, HIV-1
      TAT-Chondroitinase ABC I N(delta)60 Nucleic Acid
<220> FEATURE:
<221> NAME/KEY: misc_feature
<222> LOCATION: (948)..(948)
<223> OTHER INFORMATION: n is a, c, g, or t

<400> SEQUENCE: 42
```

| | | | | | |
|---|---|---|---|---|---|
| ggtcgtaaaa | agcgtcgtca | acgtcgtcgt | cctcctcaat | gctttacttt | acataaaaaa | 60 |
| ctgattgtcc | ccaccgataa | agaagcatct | aaagcatggg | gacgctcatc | cacccccgtt | 120 |
| ttctcatttt | ggctttacaa | tgaaaaaccg | attgatggtt | atcttactat | cgatttcgga | 180 |
| gaaaaactca | tttcaaccag | tgaggctcag | gcaggcttta | agtaaaaatt | agatttcact | 240 |
| ggctggcgta | ctgtgggagt | ctctttaaat | aacgatcttg | aaaatcgaga | gatgacctta | 300 |
| aatgcaacca | atacctcctc | tgatggtact | caagacagca | ttgggcgttc | tttaggtgct | 360 |
| aaagtcgata | gtattcgttt | taaagcgcct | tctaatgtga | gtcagggtga | aatctatatc | 420 |
| gaccgtatta | tgttttctgt | cgatgatgct | cgctaccaat | ggtctgatta | tcaagtaaaa | 480 |
| actcgcttat | cagaacctga | aattcaattt | cacaacgtaa | agccacaact | acctgtaaca | 540 |
| cctgaaaatt | tagcggccat | tgatcttatt | cgccaacgtc | taattaatga | atttgtcgga | 600 |
| ggtgaaaaag | agacaaacct | cgcattagaa | gagaatatca | gcaaattaaa | aagtgatttc | 660 |
| gatgctctta | atactcacac | tttagcaaat | ggtggaacgc | aaggcagaca | tctgatcact | 720 |
| gataaacaaa | tcattattta | tcaaccagag | aatcttaact | ctcaagataa | acaactattt | 780 |
| gataattatg | ttattttagg | taattacacg | acattaatgt | ttaatattag | ccgtgcttat | 840 |
| gtgctggaaa | aagatcccac | acaaaaggcg | caactaaagc | agatgtactt | attaatgaca | 900 |
| aagcatttat | tagatcaagg | ctttgttaaa | gggagtgctt | tagtgacnac | ccatcactgg | 960 |
| ggatacagtt | ctcgttggtg | gtatatttcc | acgttattaa | tgtctgatgc | actaaaagaa | 1020 |
| gcgaacctac | aaactcaagt | ttatgattca | ttactgtggt | attcacgtga | gtttaaaagt | 1080 |
| agttttgata | tgaaagtaag | tgctgatagc | tctgatctag | attatttcaa | taccttatct | 1140 |
| cgccaacatt | tagccttatt | actactagag | cctgatgatc | aaaagcgtat | caacttagtt | 1200 |
| aatacttca | gccattatat | cactggcgca | ttaacgcaag | tgccaccggg | tggtaaagat | 1260 |
| ggtttacgcc | ctgatggtac | agcatggcga | catgaaggca | actatccggg | ctactctttc | 1320 |
| ccagccttta | aaaatgcctc | tcagcttatt | tatttattac | gcgatacacc | attttcagtg | 1380 |
| ggtgaaagtg | gttggaatag | cctgaaaaaa | gcgatggttt | cagcgtggat | ctacagtaat | 1440 |
| ccagaagttg | gattaccgct | tgcaggaaga | caccctctta | actcaccttc | gttaaaatca | 1500 |
| gtcgctcaag | gctattactg | gcttgccatg | tctgcaaaat | catcgcctga | taaacactt | 1560 |
| gcatctattt | atcttgcgat | tagtgataaa | acacaaaatg | aatcaactgc | tattttggga | 1620 |
| gaaactatta | caccagcgtc | tttacctcaa | ggtttctatg | cctttaatgg | cggtgctttt | 1680 |
| ggtattcatc | gttggcaaga | taaaatggtg | acactgaaag | cttataacac | caatgtttgg | 1740 |
| tcatctgaaa | tttataacaa | agataaccgt | tatggccgtt | accaaagtca | tggtgtcgct | 1800 |
| caaatagtga | gtaatggctc | gcagctttca | cagggctatc | agcaagaagg | ttgggattgg | 1860 |
| aatagaatgc | caggggcaac | cactatccac | cttcctctta | aagacttaga | cagtcctaaa | 1920 |
| cctcataccct | taatgcaacg | tggagagcgt | ggatttagcg | gaacatcatc | ccttgaaggt | 1980 |

```
caatatggca tgatggcatt cgatcttatt tatcccgcca atcttgagcg ttttgatcct      2040
aatttcactg cgaaaaagag tgtattagcc gctgataatc acttaatttt tattggtagc      2100
aatataaata gtagtgataa aaataaaaat gttgaaacga ccttattcca acatgccatt      2160
actccaacat taaataccct ttggattaat ggacaaaaga tagaaaacat gccttatcaa      2220
acaacacttc aacaaggtga ttggttaatt gatagcaatg gcaatggtta cttaattact      2280
caagcagaaa aagtaaatgt aagtcgccaa catcaggttt cagcggaaaa taaaaatcgc      2340
caaccgacag aaggaaactt tagctcggca tggatcgatc acagcactcg ccccaaagat      2400
gccagttatg agtatatggt cttttttagat gcgacacctg aaaaaatggg agagatggca      2460
caaaaattcc gtgaaaataa tgggttatat caggttcttc gtaaggataa agacgttcat      2520
attattctcg ataaactcag caatgtaacg gatatgcct tttatcagcc agcatcaatt       2580
gaagacaaat ggatcaaaaa ggttaataaa cctgcaattg tgatgactca tcgacaaaaa      2640
gacactctta ttgtcagtgc agttacacct gatttaaata tgactcgcca aaaagcagca      2700
actcctgtca ccatcaatgt cacgattaat ggcaaatggc aatctgctga taaaaatagt      2760
gaagtgaaat atcaggtttc tggtgataac actgaactga cgtttacgag ttactttggt      2820
attccacaag aaatcaaact ctcgccactc ccttga                                2856
```

<210> SEQ ID NO 43
<211> LENGTH: 951
<212> TYPE: PRT
<213> ORGANISM: Artificial
<220> FEATURE:
<223> OTHER INFORMATION: Synthetic polypeptide, HIV-1 TAT chondroitinase
      ABC I-N60 fusion polypeptide

<400> SEQUENCE: 43

```
Gly Arg Lys Lys Arg Arg Gln Arg Arg Pro Pro Gln Cys Phe Thr
1               5                   10                  15

Leu His Lys Lys Leu Ile Val Pro Thr Asp Lys Glu Ala Ser Lys Ala
            20                  25                  30

Trp Gly Arg Ser Ser Thr Pro Val Phe Ser Phe Trp Leu Tyr Asn Glu
        35                  40                  45

Lys Pro Ile Asp Gly Tyr Leu Thr Ile Asp Phe Gly Glu Lys Leu Ile
    50                  55                  60

Ser Thr Ser Glu Ala Gln Ala Gly Phe Lys Val Lys Leu Asp Phe Thr
65                  70                  75                  80

Gly Trp Arg Thr Val Gly Val Ser Leu Asn Asn Asp Leu Glu Asn Arg
                85                  90                  95

Glu Met Thr Leu Asn Ala Thr Asn Thr Ser Ser Asp Gly Thr Gln Asp
            100                 105                 110

Ser Ile Gly Arg Ser Leu Gly Ala Lys Val Asp Ser Ile Arg Phe Lys
        115                 120                 125

Ala Pro Ser Asn Val Ser Gln Gly Glu Ile Tyr Ile Asp Arg Ile Met
    130                 135                 140

Phe Ser Val Asp Asp Ala Arg Tyr Gln Trp Ser Asp Tyr Gln Val Lys
145                 150                 155                 160

Thr Arg Leu Ser Glu Pro Glu Ile Gln Phe His Asn Val Lys Pro Gln
                165                 170                 175

Leu Pro Val Thr Pro Glu Asn Leu Ala Ala Ile Asp Leu Ile Arg Gln
            180                 185                 190

Arg Leu Ile Asn Glu Phe Val Gly Gly Glu Lys Glu Thr Asn Leu Ala
        195                 200                 205
```

```
Leu Glu Glu Asn Ile Ser Lys Leu Lys Ser Asp Phe Asp Ala Leu Asn
        210                 215                 220

Thr His Thr Leu Ala Asn Gly Gly Thr Gln Gly Arg His Leu Ile Thr
225                 230                 235                 240

Asp Lys Gln Ile Ile Ile Tyr Gln Pro Glu Asn Leu Asn Ser Gln Asp
                245                 250                 255

Lys Gln Leu Phe Asp Asn Tyr Val Ile Leu Gly Asn Tyr Thr Thr Leu
            260                 265                 270

Met Phe Asn Ile Ser Arg Ala Tyr Val Leu Glu Lys Asp Pro Thr Gln
        275                 280                 285

Lys Ala Gln Leu Lys Gln Met Tyr Leu Leu Met Thr Lys His Leu Leu
    290                 295                 300

Asp Gln Gly Phe Val Lys Gly Ser Ala Leu Val Thr Thr His His Trp
305                 310                 315                 320

Gly Tyr Ser Ser Arg Trp Trp Tyr Ile Ser Thr Leu Leu Met Ser Asp
                325                 330                 335

Ala Leu Lys Glu Ala Asn Leu Gln Thr Gln Val Tyr Asp Ser Leu Leu
            340                 345                 350

Trp Tyr Ser Arg Glu Phe Lys Ser Ser Phe Asp Met Lys Val Ser Ala
        355                 360                 365

Asp Ser Ser Asp Leu Asp Tyr Phe Asn Thr Leu Ser Arg Gln His Leu
370                 375                 380

Ala Leu Leu Leu Leu Glu Pro Asp Asp Gln Lys Arg Ile Asn Leu Val
385                 390                 395                 400

Asn Thr Phe Ser His Tyr Ile Thr Gly Ala Leu Thr Gln Val Pro Pro
                405                 410                 415

Gly Gly Lys Asp Gly Leu Arg Pro Asp Gly Thr Ala Trp Arg His Glu
            420                 425                 430

Gly Asn Tyr Pro Gly Tyr Ser Phe Pro Ala Phe Lys Asn Ala Ser Gln
        435                 440                 445

Leu Ile Tyr Leu Leu Arg Asp Thr Pro Phe Ser Val Gly Glu Ser Gly
    450                 455                 460

Trp Asn Ser Leu Lys Lys Ala Met Val Ser Ala Trp Ile Tyr Ser Asn
465                 470                 475                 480

Pro Glu Val Gly Leu Pro Leu Ala Gly Arg His Pro Leu Asn Ser Pro
                485                 490                 495

Ser Leu Lys Ser Val Ala Gln Gly Tyr Tyr Trp Leu Ala Met Ser Ala
            500                 505                 510

Lys Ser Ser Pro Asp Lys Thr Leu Ala Ser Ile Tyr Leu Ala Ile Ser
        515                 520                 525

Asp Lys Thr Gln Asn Glu Ser Thr Ala Ile Phe Gly Glu Thr Ile Thr
    530                 535                 540

Pro Ala Ser Leu Pro Gln Gly Phe Tyr Ala Phe Asn Gly Gly Ala Phe
545                 550                 555                 560

Gly Ile His Arg Trp Gln Asp Lys Met Val Thr Leu Lys Ala Tyr Asn
                565                 570                 575

Thr Asn Val Trp Ser Ser Glu Ile Tyr Asn Lys Asp Asn Arg Tyr Gly
            580                 585                 590

Arg Tyr Gln Ser His Gly Val Ala Gln Ile Val Ser Asn Gly Ser Gln
        595                 600                 605

Leu Ser Gln Gly Tyr Gln Gln Glu Gly Trp Asp Trp Asn Arg Met Pro
    610                 615                 620

Gly Ala Thr Thr Ile His Leu Pro Leu Lys Asp Leu Asp Ser Pro Lys
625                 630                 635                 640
```

Pro His Thr Leu Met Gln Arg Gly Glu Arg Gly Phe Ser Gly Thr Ser
            645                 650                 655

Ser Leu Glu Gly Gln Tyr Gly Met Met Ala Phe Asp Leu Ile Tyr Pro
            660                 665                 670

Ala Asn Leu Glu Arg Phe Asp Pro Asn Phe Thr Ala Lys Lys Ser Val
            675                 680                 685

Leu Ala Ala Asp Asn His Leu Ile Phe Ile Gly Ser Asn Ile Asn Ser
            690                 695                 700

Ser Asp Lys Asn Lys Asn Val Glu Thr Thr Leu Phe Gln His Ala Ile
705                 710                 715                 720

Thr Pro Thr Leu Asn Thr Leu Trp Ile Asn Gly Gln Lys Ile Glu Asn
            725                 730                 735

Met Pro Tyr Gln Thr Thr Leu Gln Gln Gly Asp Trp Leu Ile Asp Ser
            740                 745                 750

Asn Gly Asn Gly Tyr Leu Ile Thr Gln Ala Glu Lys Val Asn Val Ser
            755                 760                 765

Arg Gln His Gln Val Ser Ala Glu Asn Lys Asn Arg Gln Pro Thr Glu
770                 775                 780

Gly Asn Phe Ser Ser Ala Trp Ile Asp His Ser Thr Arg Pro Lys Asp
785                 790                 795                 800

Ala Ser Tyr Glu Tyr Met Val Phe Leu Asp Ala Thr Pro Glu Lys Met
            805                 810                 815

Gly Glu Met Ala Gln Lys Phe Arg Glu Asn Asn Gly Leu Tyr Gln Val
            820                 825                 830

Leu Arg Lys Asp Lys Asp Val His Ile Ile Leu Asp Lys Leu Ser Asn
            835                 840                 845

Val Thr Gly Tyr Ala Phe Tyr Gln Pro Ala Ser Ile Glu Asp Lys Trp
            850                 855                 860

Ile Lys Lys Val Asn Lys Pro Ala Ile Val Met Thr His Arg Gln Lys
865                 870                 875                 880

Asp Thr Leu Ile Val Ser Ala Val Thr Pro Asp Leu Asn Met Thr Arg
            885                 890                 895

Gln Lys Ala Ala Thr Pro Val Thr Ile Asn Val Thr Ile Asn Gly Lys
            900                 905                 910

Trp Gln Ser Ala Asp Lys Asn Ser Glu Val Lys Tyr Gln Val Ser Gly
            915                 920                 925

Asp Asn Thr Glu Leu Thr Phe Thr Ser Tyr Phe Gly Ile Pro Gln Glu
930                 935                 940

Ile Lys Leu Ser Pro Leu Pro
945                 950

<210> SEQ ID NO 44
<211> LENGTH: 3036
<212> TYPE: DNA
<213> ORGANISM: Artificial
<220> FEATURE:
<223> OTHER INFORMATION: Synthetic polynucleotide, C terminal HIV-1
      TAT-Chondroitinase ABC I Nucleic Acid
<220> FEATURE:
<221> NAME/KEY: misc_feature
<222> LOCATION: (1086)..(1086)
<223> OTHER INFORMATION: n is a, c, g, or t

<400> SEQUENCE: 44
gccaccagca atcctgcatt tgatcctaaa aatctgatgc agtcagaaat ttaccatttt      60
gcacaaaata acccattagc agacttctca tcagataaaa actcaatact aacgttatct     120

```
gataaacgta gcattatggg aaaccaatct cttttatgga aatggaaagg tggtagtagc    180
tttactttac ataaaaaact gattgtcccc accgataaag aagcatctaa agcatgggga    240
cgctcatcca cccccgtttt ctcattttgg ctttacaatg aaaaaccgat tgatggttat    300
cttactatcg atttcggaga aaaactcatt tcaaccagtg aggctcaggc aggctttaaa    360
gtaaaattag atttcactgg ctggcgtact gtgggagtct ctttaaataa cgatcttgaa    420
aatcgagaga tgaccttaaa tgcaaccaat acctcctctg atggtactca agacagcatt    480
gggcgttctt taggtgctaa agtcgatagt attcgtttta aagcgccttc taatgtgagt    540
cagggtgaaa tctatatcga ccgtattatg ttttctgtcg atgatgctcg ctaccaatgg    600
tctgattatc aagtaaaaac tcgcttatca gaacctgaaa ttcaatttca caacgtaaag    660
ccacaactac ctgtaacacc tgaaaattta gcggccattg atcttattcg ccaacgtcta    720
attaatgaat tgtcggagg tgaaaagag acaaacctcg cattagaaga aatatcagc     780 aaattaaaaa gtgatttcga tgctcttaat actcacactt tagcaaatgg tggaacgcaa    840
ggcagacatc tgatcactga taaacaaatc attatttatc aaccagagaa tcttaactct    900
caagataaac aactatttga taattatgtt attttaggta attacacgac attaatgttt    960
aatattagcc gtgcttatgt gctggaaaaa gatcccacac aaaaggcgca actaaagcag   1020
atgtacttat taatgacaaa gcatttatta gatcaaggct tgttaaagg gagtgcttta   1080 gtgacnaccc atcactgggg atacagttct cgttggtggt atatttccac gttattaatg   1140
tctgatgcac taaagaagc gaacctacaa actcaagttt atgattcatt actgtggtat   1200
tcacgtgagt ttaaaagtag ttttgatatg aaagtaagtg ctgatagctc tgatctagat   1260
tatttcaata ccttatctcg ccaacattta gccttattac tactagagcc tgatgatcaa   1320
aagcgtatca acttagttaa tactttcagc cattatatca ctggcgcatt aacgcaagtg   1380
ccaccgggtg gtaaagatgg tttacgccct gatggtacag catggcgaca tgaaggcaac   1440
tatccgggct actcttcc agcctttaaa aatgcctctc agcttattta tttattacgc    1500
gatacaccat tttcagtggg tgaaagtggt tggaatagcc tgaaaaaagc gatggtttca   1560
gcgtggatct acagtaatcc agaagttgga ttaccgcttg caggaagaca ccctcttaac   1620
tcaccttcgt taaaatcagt cgctcaaggc tattactggc ttgccatgtc tgcaaaatca   1680
tcgcctgata aaacacttgc atctattat cttgcgatta gtgataaaac acaaaatgaa   1740
tcaactgcta ttttttggaga aactattaca ccagcgtctt tacctcaagg tttctatgcc   1800
tttaatggcg gtgcttttgg tattcatcgt tggcaagata aaatggtgac actgaaagct   1860
tataacacca atgtttggtc atctgaaatt tataacaaag ataaccgtta tggccgttac   1920
caaagtcatg gtgtcgctca aatagtgagt aatggctcgc agctttcaca gggctatcag   1980
caagaaggtt gggattggaa tagaatgcca ggggcaacca ctatccacct tcctcttaaa   2040
gacttagaca gtcctaaacc tcataccta atgcaacgtg gagagcgtgg attagcggaa   2100
acatcatccc ttgaaggtca atatggcatg atggcattcg atcttattta tcccgccaat   2160
cttgagcgtt ttgatcctaa tttcactgcg aaaaagagtg tattagccgc tgataatcac   2220
ttaattttta ttggtagcaa tataaatagt agtgataaaa ataaaaatgt tgaaacgacc   2280
ttattccaac atgccattac tccaacatta aatacccttt ggattaatgg acaaaagata   2340
gaaaacatgc cttatcaaac aacacttcaa caaggtgatt ggttaattga tagcaatggc   2400
aatggttact taattactca agcagaaaaa gtaaatgtaa gtcgccaaca tcaggtttca   2460
gcggaaaata aaaatcgcca accgacagaa ggaaactta gctcggcatg gatcgatcac   2520
```

-continued

```
agcactcgcc ccaaagatgc cagttatgag tatatggtct ttttagatgc gacacctgaa   2580
aaaatgggag agatggcaca aaaattccgt gaaaataatg ggttatatca ggttcttcgt   2640
aaggataaag acgttcatat tattctcgat aaactcagca atgtaacggg atatgccttt   2700
tatcagccag catcaattga agacaaatgg atcaaaaagg ttaataaacc tgcaattgtg   2760
atgactcatc gacaaaaaga cactcttatt gtcagtgcag ttacacctga tttaaatatg   2820
actcgccaaa aagcagcaac tcctgtcacc atcaatgtca cgattaatgg caaatggcaa   2880
tctgctgata aaatagtga agtgaaatat caggtttctg gtgataacac tgaactgacg    2940
tttacgagtt actttggtat tccacaagaa atcaaactct cgccactccc tggtcgtaaa   3000
aagcgtcgtc aacgtcgtcg tcctcctcaa tgctag                             3036
```

<210> SEQ ID NO 45
<211> LENGTH: 1011
<212> TYPE: PRT
<213> ORGANISM: Artificial
<220> FEATURE:
<223> OTHER INFORMATION: Synthetic polypeptide, C terminal HIV-1
      TAT-Chondroitinase ABC I with gwrt and dalnt sequences

<400> SEQUENCE: 45

```
Ala Thr Ser Asn Pro Ala Phe Asp Pro Lys Asn Leu Met Gln Ser Glu
1               5                   10                  15

Ile Tyr His Phe Ala Gln Asn Asn Pro Leu Ala Asp Phe Ser Ser Asp
            20                  25                  30

Lys Asn Ser Ile Leu Thr Leu Ser Asp Lys Arg Ser Ile Met Gly Asn
        35                  40                  45

Gln Ser Leu Leu Trp Lys Trp Lys Gly Gly Ser Ser Phe Thr Leu His
    50                  55                  60

Lys Lys Leu Ile Val Pro Thr Asp Lys Glu Ala Ser Lys Ala Trp Gly
65                  70                  75                  80

Arg Ser Ser Thr Pro Val Phe Ser Phe Trp Leu Tyr Asn Glu Lys Pro
                85                  90                  95

Ile Asp Gly Tyr Leu Thr Ile Asp Phe Gly Glu Lys Leu Ile Ser Thr
            100                 105                 110

Ser Glu Ala Gln Ala Gly Phe Lys Val Lys Leu Asp Phe Thr Gly Trp
        115                 120                 125

Arg Thr Val Gly Val Ser Leu Asn Asn Asp Leu Glu Asn Arg Glu Met
    130                 135                 140

Thr Leu Asn Ala Thr Asn Thr Ser Ser Asp Gly Thr Gln Asp Ser Ile
145                 150                 155                 160

Gly Arg Ser Leu Gly Ala Lys Val Asp Ser Ile Arg Phe Lys Ala Pro
                165                 170                 175

Ser Asn Val Ser Gln Gly Glu Ile Tyr Ile Asp Arg Ile Met Phe Ser
            180                 185                 190

Val Asp Asp Ala Arg Tyr Gln Trp Ser Asp Tyr Gln Val Lys Thr Arg
        195                 200                 205

Leu Ser Glu Pro Glu Ile Gln Phe His Asn Val Lys Pro Gln Leu Pro
    210                 215                 220

Val Thr Pro Glu Asn Leu Ala Ala Ile Asp Leu Ile Arg Gln Arg Leu
225                 230                 235                 240

Ile Asn Glu Phe Val Gly Gly Glu Lys Glu Thr Asn Leu Ala Leu Glu
                245                 250                 255

Glu Asn Ile Ser Lys Leu Lys Ser Asp Phe Asp Ala Leu Asn Thr His
            260                 265                 270
```

```
                    -continued

Thr Leu Ala Asn Gly Gly Thr Gln Gly Arg His Leu Ile Thr Asp Lys
            275                 280                 285

Gln Ile Ile Tyr Gln Pro Glu Asn Leu Asn Ser Gln Asp Lys Gln
        290                 295                 300

Leu Phe Asp Asn Tyr Val Ile Leu Gly Asn Tyr Thr Thr Leu Met Phe
305                 310                 315                 320

Asn Ile Ser Arg Ala Tyr Val Leu Glu Lys Asp Pro Thr Gln Lys Ala
                325                 330                 335

Gln Leu Lys Gln Met Tyr Leu Leu Met Thr Lys His Leu Leu Asp Gln
            340                 345                 350

Gly Phe Val Lys Gly Ser Ala Leu Val Thr Thr His His Trp Gly Tyr
                355                 360                 365

Ser Ser Arg Trp Trp Tyr Ile Ser Thr Leu Leu Met Ser Asp Ala Leu
        370                 375                 380

Lys Glu Ala Asn Leu Gln Thr Gln Val Tyr Asp Ser Leu Leu Trp Tyr
385                 390                 395                 400

Ser Arg Glu Phe Lys Ser Ser Phe Asp Met Lys Val Ser Ala Asp Ser
                405                 410                 415

Ser Asp Leu Asp Tyr Phe Asn Thr Leu Ser Arg Gln His Leu Ala Leu
            420                 425                 430

Leu Leu Leu Glu Pro Asp Asp Gln Lys Arg Ile Asn Leu Val Asn Thr
        435                 440                 445

Phe Ser His Tyr Ile Thr Gly Ala Leu Thr Gln Val Pro Pro Gly Gly
    450                 455                 460

Lys Asp Gly Leu Arg Pro Asp Gly Thr Ala Trp Arg His Glu Gly Asn
465                 470                 475                 480

Tyr Pro Gly Tyr Ser Phe Pro Ala Phe Lys Asn Ala Ser Gln Leu Ile
                485                 490                 495

Tyr Leu Leu Arg Asp Thr Pro Phe Ser Val Gly Glu Ser Gly Trp Asn
            500                 505                 510

Ser Leu Lys Lys Ala Met Val Ser Ala Trp Ile Tyr Ser Asn Pro Glu
        515                 520                 525

Val Gly Leu Pro Leu Ala Gly Arg His Pro Leu Asn Ser Pro Ser Leu
    530                 535                 540

Lys Ser Val Ala Gln Gly Tyr Tyr Trp Leu Ala Met Ser Ala Lys Ser
545                 550                 555                 560

Ser Pro Asp Lys Thr Leu Ala Ser Ile Tyr Leu Ala Ile Ser Asp Lys
                565                 570                 575

Thr Gln Asn Glu Ser Thr Ala Ile Phe Gly Glu Thr Ile Thr Pro Ala
            580                 585                 590

Ser Leu Pro Gln Gly Phe Tyr Ala Phe Asn Gly Gly Ala Phe Gly Ile
        595                 600                 605

His Arg Trp Gln Asp Lys Met Val Thr Leu Lys Ala Tyr Asn Thr Asn
    610                 615                 620

Val Trp Ser Ser Glu Ile Tyr Asn Lys Asp Asn Arg Tyr Gly Arg Tyr
625                 630                 635                 640

Gln Ser His Gly Val Ala Gln Ile Val Ser Asn Gly Ser Gln Leu Ser
                645                 650                 655

Gln Gly Tyr Gln Gln Glu Gly Trp Asp Trp Asn Arg Met Pro Gly Ala
            660                 665                 670

Thr Thr Ile His Leu Pro Leu Lys Asp Leu Asp Ser Pro Lys Pro His
        675                 680                 685

Thr Leu Met Gln Arg Gly Glu Arg Gly Phe Ser Gly Thr Ser Ser Leu
    690                 695                 700
```

```
Glu Gly Gln Tyr Gly Met Met Ala Phe Asp Leu Ile Tyr Pro Ala Asn
705                 710                 715                 720

Leu Glu Arg Phe Asp Pro Asn Phe Thr Ala Lys Lys Ser Val Leu Ala
            725                 730                 735

Ala Asp Asn His Leu Ile Phe Ile Gly Ser Asn Ile Asn Ser Ser Asp
        740                 745                 750

Lys Asn Lys Asn Val Glu Thr Thr Leu Phe Gln His Ala Ile Thr Pro
    755                 760                 765

Thr Leu Asn Thr Leu Trp Ile Asn Gly Gln Lys Ile Glu Asn Met Pro
770                 775                 780

Tyr Gln Thr Thr Leu Gln Gln Gly Asp Trp Leu Ile Asp Ser Asn Gly
785                 790                 795                 800

Asn Gly Tyr Leu Ile Thr Gln Ala Glu Lys Val Asn Val Ser Arg Gln
                805                 810                 815

His Gln Val Ser Ala Glu Asn Lys Asn Arg Gln Pro Thr Glu Gly Asn
            820                 825                 830

Phe Ser Ser Ala Trp Ile Asp His Ser Thr Arg Pro Lys Asp Ala Ser
        835                 840                 845

Tyr Glu Tyr Met Val Phe Leu Asp Ala Thr Pro Glu Lys Met Gly Glu
    850                 855                 860

Met Ala Gln Lys Phe Arg Glu Asn Asn Gly Leu Tyr Gln Val Leu Arg
865                 870                 875                 880

Lys Asp Lys Asp Val His Ile Ile Leu Asp Lys Leu Ser Asn Val Thr
                885                 890                 895

Gly Tyr Ala Phe Tyr Gln Pro Ala Ser Ile Glu Asp Lys Trp Ile Lys
            900                 905                 910

Lys Val Asn Lys Pro Ala Ile Val Met Thr His Arg Gln Lys Asp Thr
        915                 920                 925

Leu Ile Val Ser Ala Val Thr Pro Asp Leu Asn Met Thr Arg Gln Lys
    930                 935                 940

Ala Ala Thr Pro Val Thr Ile Asn Val Thr Ile Asn Gly Lys Trp Gln
945                 950                 955                 960

Ser Ala Asp Lys Asn Ser Glu Val Lys Tyr Gln Val Ser Gly Asp Asn
                965                 970                 975

Thr Glu Leu Thr Phe Thr Ser Tyr Phe Gly Ile Pro Gln Glu Ile Lys
            980                 985                 990

Leu Ser Pro Leu Pro Gly Arg Lys  Lys Arg Arg Gln Arg  Arg Arg Pro
        995                 1000                1005

Pro Gln  Cys
    1010
```

<210> SEQ ID NO 46
<211> LENGTH: 2934
<212> TYPE: DNA
<213> ORGANISM: Artificial
<220> FEATURE:
<223> OTHER INFORMATION: Synthetic polynucleotide, chondroitinase ABC
      I-N(delta)20
<220> FEATURE:
<221> NAME/KEY: misc_feature
<222> LOCATION: (1026)..(1026)
<223> OTHER INFORMATION: n is a, c, g, or t

<400> SEQUENCE: 46
gcacaaaata acccattagc agacttctca tcagataaaa actcaatact aacgttatct    60
gataaacgta gcattatggg aaaccaatct cttttatgga aatggaaagg tggtagtagc   120

```
tttactttac ataaaaaact gattgtcccc accgataaag aagcatctaa agcatgggga    180
cgctcatcca cccccgtttt ctcattttgg ctttacaatg aaaaaccgat tgatggttat    240
cttactatcg atttcggaga aaaactcatt tcaaccagtg aggctcaggc aggctttaaa    300
gtaaaattag atttcactgg ctggcgtact gtgggagtct ctttaaataa cgatcttgaa    360
aatcgagaga tgaccttaaa tgcaaccaat acctcctctg atggtactca agacagcatt    420
gggcgttctt taggtgctaa agtcgatagt attcgtttta aagcgccttc taatgtgagt    480
cagggtgaaa tctatatcga ccgtattatg ttttctgtcg atgatgctcg ctaccaatgg    540
tctgattatc aagtaaaaac tcgcttatca gaacctgaaa ttcaatttca aacgtaaag     600 ccacaactac ctgtaacacc tgaaaattta gcggccattg atcttattcg ccaacgtcta    660
attaatgaat tgtcggagg tgaaaaagag acaaacctcg cattagaaga gaatatcagc     720
aaattaaaaa gtgatttcga tgctcttaat actcacactt tagcaaatgg tggaacgcaa    780
ggcagacatc tgatcactga taacaaatc attatttatc aaccagagaa tcttaactct      840
caagataaac aactatttga taattatgtt attttaggta attacacgac attaatgttt    900
aatattagcc gtgcttatgt gctgaaaaaa gatcccacac aaaaggcgca actaaagcag    960
atgtacttat taatgacaaa gcatttatta gatcaaggct ttgttaaagg gagtgcttta   1020
gtgacnaccc atcactgggg atacagttct cgttggtggt atatttccac gttattaatg   1080
tctgatgcac taaagaagc gaacctacaa actcaagttt atgattcatt actgtggtat    1140
tcacgtgagt ttaaaagtag ttttgatatg aaagtaagtg ctgatagctc tgatctagat   1200
tatttcaata ccttatctcg ccaacattta gccttattac tactagagcc tgatgatcaa   1260
aagcgtatca acttagttaa tactttcagc cattatatca ctggcgcatt aacgcaagtg   1320
ccaccgggtg gtaaagatgg tttacgccct gatggtacag catggcgaca tgaaggcaac   1380
tatccgggct actctttccc agcctttaaa aatgcctctc agcttattta tttattacgc   1440
gatacaccat tttcagtggg tgaaagtggt tggaatagcc tgaaaaaagc gatggtttca   1500
gcgtggatct acagtaatcc agaagttgga ttaccgcttg caggaagaca ccctcttaac   1560
tcaccttcgt taaaatcagt cgctcaaggc tattactggc ttgccatgtc tgcaaaatca   1620
tcgcctgata aaacttgc atctatttat cttgcgatta gtgataaaac acaaaatgaa     1680
tcaactgcta ttttggaga aactattaca ccagcgtctt tacctcaagg tttctatgcc    1740
tttaatggcg gtgcttttgg tattcatcgt tggcaagata aaatggtgac actgaaagct   1800
tataacacca atgtttggtc atctgaaatt tataacaaag ataaccgtta tggccgttac   1860
caaagtcatg gtgtcgctca aatagtgagt aatggctcgc agctttcaca gggctatcag   1920
caagaaggtt gggattggaa tagaatgcca ggggcaacca ctatccacct tcctcttaaa   1980
gacttagaca gtcctaaacc tcatacctta atgcaacgtg gagagcgtgg atttagcgga   2040
acatcatccc ttgaaggtca atatggcatg atggcattcg atcttattta tcccgccaat   2100
cttgagcgtt ttgatcctaa tttcactgcg aaaaagagtg tattagccgc tgataatcac   2160
ttaattttta ttggtagcaa tataaatagt agtgataaaa ataaaaatgt tgaaacgacc   2220
ttattccaac atgccattac tccaacatta aatacccttt ggattaatgg acaaaagata   2280 gaaacatgc cttatcaaac aacacttcaa caaggtgatt ggttaattga tagcaatggc    2340
aatggttact aattactca agcagaaaaa gtaaatgtaa gtcgccaaca tcaggtttca    2400
gcggaaaata aaaatcgcca accgacagaa ggaaacttta gctcggcatg gatcgatcac   2460
agcactcgcc ccaaagatgc cagttatgag tatatggtct ttttagatgc gacacctgaa   2520
```

-continued

```
aaaatgggag agatggcaca aaaattccgt gaaataatg ggttatatca ggttcttcgt    2580
aaggataaag acgttcatat tattctcgat aaactcagca atgtaacggg atatgccttt    2640
tatcagccag catcaattga agacaaatgg atcaaaaagg ttaataaacc tgcaattgtg    2700
atgactcatc gacaaaaaga cactcttatt gtcagtgcag ttacacctga tttaaatatg    2760
actcgccaaa aagcagcaac tcctgtcacc atcaatgtca cgattaatgg caaatggcaa    2820
tctgctgata aaaatagtga agtgaaatat caggtttctg gtgataacac tgaactgacg    2880
tttacgagtt actttggtat tccacaagaa atcaaactct cgccactccc ttga          2934
```

<210> SEQ ID NO 47
<211> LENGTH: 2814
<212> TYPE: DNA
<213> ORGANISM: Artificial
<220> FEATURE:
<223> OTHER INFORMATION: Synthetic polynucleotide, chondroitinase ABC
      I-N(delta)60
<220> FEATURE:
<221> NAME/KEY: misc_feature
<222> LOCATION: (906)..(906)
<223> OTHER INFORMATION: n is a, c, g, or t

<400> SEQUENCE: 47

```
tttactttac ataaaaaact gattgtcccc accgataaag aagcatctaa agcatgggga      60
cgctcatcca cccccgtttt tcatttttgg ctttacaatg aaaaaccgat tgatggttat     120
cttactatcg atttcggaga aaaactcatt tcaaccagtg aggctcaggc aggctttaaa     180
gtaaaattag atttcactgg ctggcgtact gtgggagtct cttaaataa cgatcttgaa      240 aatcgagaga tgaccttaaa tgcaaccaat acctcctctg atggtactca agacagcatt     300
gggcgttctt taggtgctaa agtcgatagt attcgtttta aagcgccttc taatgtgagt     360
cagggtgaaa tctatatcga ccgtattatg ttttctgtcg atgatgctcg ctaccaatgg     420
tctgattatc aagtaaaaac tcgcttatca gaacctgaaa ttcaatttca aacgtaaag     480 ccacaactac ctgtaacacc tgaaaattta gcggccattg atcttattcg ccaacgtcta     540
attaatgaat tgtcggagg tgaaaaagag acaaacctcg cattagaaga gaatatcagc     600
aaattaaaaa gtgatttcga tgctcttaat actcacactt tagcaaatgg tggaacgcaa     660
ggcagacatc tgatcactga taaacaaatc attatttatc aaccagagaa tcttaactct     720
caagataaac aactatttga taattatgtt attttaggta attacacgac attaatgttt     780
aatattagcc gtgcttatgt gctggaaaaa gatcccacac aaaaggcgca actaaagcag     840
atgtacttat taatgacaaa gcatttatta gatcaaggct ttgttaaagg gagtgcttta     900
gtgacnaccc atcactgggg atacagttct cgttggtggt atatttccac gttattaatg     960
tctgatgcac taaaagaagc gaacctacaa actcaagttt atgattcatt actgtggtat    1020
tcacgtgagt ttaaaagtag ttttgatatg aaagtaagtg ctgatagctc tgatctagat    1080
tatttcaata ccttatctcg ccaacattta gccttattac tactagagcc tgatgatcaa    1140
aagcgtatca acttagttaa tactttcagc cattatatca ctggcgcatt aacgcaagtg    1200
ccaccgggtg gtaaagatgg tttacgccct gatggtacag catggcgaca tgaaggcaac    1260
tatccgggct actctttccc agcctttaaa aatgcctctc agcttatta tttattacgc    1320 gatacaccat tttcagtggg tgaaagtggt tggaatagcc tgaaaaagc gatggtttca    1380 gcgtggatct acagtaatcc agaagttgga ttaccgcttg caggaagaca ccctcttaac    1440
tcaccttcgt taaaatcagt cgctcaaggc tattactggc ttgccatgtc tgcaaaatca    1500
tcgcctgata aaacacttgc atctatttat cttgcgatta gtgataaaac acaaaatgaa    1560
```

```
tcaactgcta ttttggaga aactattaca ccagcgtctt tacctcaagg tttctatgcc    1620
tttaatggcg gtgcttttgg tattcatcgt tggcaagata aaatggtgac actgaaagct    1680
tataacacca atgtttggtc atctgaaatt tataacaaag ataaccgtta tggccgttac    1740
caaagtcatg gtgtcgctca aatagtgagt aatggctcgc agctttcaca gggctatcag    1800
caagaaggtt gggattggaa tagaatgcca ggggcaacca ctatccacct tcctcttaaa    1860
gacttagaca gtcctaaacc tcataccttta atgcaacgtg gagagcgtgg atttagcgga    1920
acatcatccc ttgaaggtca atatggcatg atggcattcg atcttattta tcccgccaat    1980
cttgagcgtt ttgatcctaa tttcactgcg aaaaagagtg tattagccgc tgataatcac    2040
ttaattttta ttggtagcaa tataaatagt agtgataaaa ataaaaatgt tgaaacgacc    2100
ttattccaac atgccattac tccaacatta aatacccttt ggattaatgg acaaaagata    2160
gaaaacatgc cttatcaaac aacacttcaa caaggtgatt ggttaattga tagcaatggc    2220
aatggttact taattactca agcagaaaaa gtaaatgtaa gtcgccaaca tcaggtttca    2280
gcggaaaata aaaatcgcca accgacagaa ggaaacttta gctcggcatg gatcgatcac    2340
agcactcgcc ccaaagatgc cagttatgag tatatggtct ttttagatgc gacacctgaa    2400
aaaatgggag agatggcaca aaaattccgt gaaaataatg ggttatatca ggttcttcgt    2460
aaggataaag acgttcatat tattctcgat aaactcagca atgtaacggg atatgccttt    2520
tatcagccag catcaattga agacaaatgg atcaaaaagg ttaataaacc tgcaattgtg    2580
atgactcatc gacaaaaaga cactcttatt gtcagtgcag ttacacctga tttaaatatg    2640
actcgccaaa aagcagcaac tcctgtcacc atcaatgtca cgattaatgg caaatggcaa    2700
tctgctgata aaaatagtga agtgaaatat caggtttctg gtgataacac tgaactgacg    2760
tttacgagtt actttggtat tccacaagaa atcaaactct cgccactccc ttga          2814
```

<210> SEQ ID NO 48
<211> LENGTH: 42
<212> TYPE: DNA
<213> ORGANISM: Artificial
<220> FEATURE:
<223> OTHER INFORMATION: Synthetic polynucleotide, HIV-1 TAT construct
      portion

<400> SEQUENCE: 48
ggtcgtaaaa agcgtcgtca acgtcgtcgt cctcctcaat gc                          42

<210> SEQ ID NO 49
<211> LENGTH: 14
<212> TYPE: PRT
<213> ORGANISM: Artificial
<220> FEATURE:
<223> OTHER INFORMATION: Synthetic polypeptide, amino acid sequence for
      a TAT peptide

<400> SEQUENCE: 49

Gly Arg Lys Lys Arg Arg Gln Arg Arg Arg Pro Pro Gln Cys
1               5                   10

<210> SEQ ID NO 50
<211> LENGTH: 45
<212> TYPE: DNA
<213> ORGANISM: Artificial
<220> FEATURE:
<223> OTHER INFORMATION: Synthetic Polynucleotide, Chodroitinase ABC II
      Nucleic Acid

```
<400> SEQUENCE: 50
ggtcgtaaaa agcgtcgtca acgtcgtcgt ggtggtggtg gtggt                    45
```

US 7,968,089 B2

PROTEOGLYCAN DEGRADING MUTANTS FOR THE TREATMENT OF CNS

CROSS-REFERENCE TO RELATED APPLICATIONS

This application is a continuation of U.S. patent application Ser. No. 10/848,561, filed May 17, 2004, now U.S. Pat. No. 7,429,375 which claims the benefit and priority of U.S. Provisional Application Ser. No. 60/471,240, filed May 16, 2003; U.S. Provisional Application Ser. No. 60/471,239, filed May 16, 2003; U.S. Provisional Application Ser. No. 60/471,300, filed May 16, 2003; U.S. Provisional Application Ser. No. 60/474,372 filed May 16, 2003; and is related to U.S. patent application Ser. No. 10/848,564 filed May 17, 2004. The contents of each of these references is incorporated herein by reference in their entirety.

SEQUENCE LISTING REFERENCE

The sequence listing 127304.01301.5T25.txt file submitted herewith is incorporated by reference in its entirety.

BACKGROUND AND SUMMARY

Chondroitinases are enzymes of bacterial origin that act on chondroitin sulfate, a component of the proteoglycans that are components of the extracellular matrix of a wide variety of tissues such as the central nervous system and for example they can mediate the attachment between the retina and the vitreous body of the human eye. Examples of chondroitinase enzymes are chondroitinase ABC I, SEQ ID NO: 37, which is produced by the bacterium *Proteus vulgaris* (*P. vulgaris*), and chondroitinase AC, SEQ ID NO: 5, which is produced by *Flavobacterium* heparinum. Chondroitinases ABC I SEQ ID NO: 37, and chondroitinase AC SEQ ID NO: 5, function by degrading polysaccharide side chains in protein-polysaccharide complexes, without degrading the protein core.

Yarnagata et al. (J. Biol. Chem. 243:1523-1535, 1968) describe the purification of the chondroitinases like ABC I SEQ ID NO: 37 from extracts of *P. vulgaris*. This enzyme selectively degrades the glycosaminoglycans chondroitin-4-sulfate, dermatan sulfate, and chondroitin-6-sulfate (also referred to respectively as chondroitin sulfates A, B, and C which are side chains of proteoglycans) at pH 8 at higher rates than it degrades chondroitin or hyaluronic acid. The products of the degradation are high molecular weight unsaturated oligosaccharides and an unsaturated disaccharide. However, chondroitinase ABC I, SEQ ID NO: 37, does not act on keratosulfate, heparin or heparitin sulfate.

Uses of chondroitinases include rapid, specific and non-surgical disruption of the attachment of the vitreous body to the neural retina of the eye, thereby facilitating removal of the vitreous body.

*P. vulgaris* chondroitinase ABC I SEQ ID NO: 1 migrates with an apparent molecular mass of about 110 kDa when resolved by SDS-PAGE. The appearance of a doublet in SDS-PAGE resolution of chondroitinase ABC has been reported (Sato et al., Agric. Biol. Chem. 50:4, 1057-1059, 1986). However, this doublet represents intact chondroitinase ABC and a 90 kDa degradation product. Commercial chondroitinase ABC protein preparations contain variable amounts of this 90 kDa degradation product and an additional 18 kDa degradation product also derived from chondroitinase ABC I, SEQ ID NO: 1.

Chondroitinase ABC II, SEQ ID NO: 26, has also been isolated and purified from *P. vulgaris*, Chondroitinase ABC II, SEQ ID NO: 26, is a polypeptide of 990 amino acids with an apparent molecular mass by SDS-PAGE of about 112 kDa. Its molecular mass as determined by electrospray and laser desorption mass spectrometry is about 111,772 daltons. Chondroitinase ABC II, SEQ ID NO: 26, has an isoelectric point of 8.4-8.45. Its enzymatic activity is distinct from, but complementary to, that of chondroitinase ABC I SEQ ID NO: 1. Chondroitinase ABC I, SEQ ID NO: 1, endolytically cleaves proteoglycans to produce end-product disaccharides, as well as at least two other products which are thought to be tetrasaccharides, Chondroitinase ABC II, SEQ ID NO: 26, digests at least one of these tetrasaccharide products from the chondroitinase ABC I (SEQ ID NO: 1) digestion of proteoglycan.

After a injury in the adult mammalian central nervous system (CNS), the inability of axons to regenerate may lead to permanent paralysis. An injury-caused lesion will develop glial scarring, which contains extracellular matrix molecules including chondroitin sulfate proteoglycans (CSPGs). CSPGs inhibit nerve tissue growth in vitro, and nerve tissue regeneration fails at CSPGs rich regions in vivo.

A number of molecules, and specified regions of them, have been implicated in the ability to support the sprouting of neurites from a neuronal cell, a process also referred to as neurite outgrowth. The term neurite refers to both axon and dendrite structures. This process of spouting neurites is essential in neural development and regeneration, especially after physical injury or disease has damaged neuronal cells. Neurites elongate profusely during development both in the central and peripheral nervous systems of all animal species. This phenomenon pertains to both axons and dendrites. However, neurite regrowth in the CNS decreases as the animal's age increases.

Chondroitinase enzymes have shown efficacy in improving functional outcomes in several in vivo models of spinal cord injury. Recombinantly produced chondroitinases AC (SEQ ID NO: 5) and chondroitinase B (SEQ ID NO: 12) polypeptides have shown efficacy in vitro by overcoming the barrier of an inhibitory substrate border, such as aggrecan, resulting in neurite extension for rat cortical neurons.

The inventors have discovered through a deletion analysis based on the available crystal structures, the minimally sized polypeptides capable of degrading chondroitin sulfate proteoglycans (CSPGs). The cleavage activity of all these mutants have been screened in vitro by zymographic assay using aggrecan as a substrate. A truncated polypeptide of chondroitinase AC (nΔ50-cΔ275), (SEQ ID NO: 11), lacking 50 and 275 amino acids from the amino and carboxy termini respectively and having a molecular weight of 38 kDa compared to 75 kDa of the full length protein, was found to be the minimal size that retained activity as tested by a zymographic assay. The deletion mutant of chondroitinase B (nΔ120-cΔ120), (SEQ ID NO: 17), lacking 120 amino acids from each of the amino and carboxy termini and having a molecular weight of 26 kDa compared to 52 kDa of the full length protein, was shown to retain activity as well in a zymographic assay. Reduction in the size and complexity of the molecule may facilitate diffusion to the site of action and potentially reduce immunogenicity for prolonged therapeutic use. These smaller chondroitinases could be potential therapeutics for spinal cord injury.

The present disclosure relates to mutants of chondroitinase genes, polypeptides and proteins derived therefrom, and their use in methods for promoting neurological functional recovery after central nervous system ("CNS") injury or disease. The mutant genes, polypeptides and proteins derived from them preferably include deletion, substitution, or a combination of these from the structural units the mature gene or polypeptide; more preferably the mutant genes or polypeptides are deletion mutants of the mature gene or polypeptide. These mutant genes or polypeptides, preferably biologically active, may be used in various pharmaceutical compositions.

Polypeptide mutants of chondroitinase ABC Type I, SEQ ID NO: 1, Chondroitinase ABC Type II, SEQ ID NO: 26, Chondroitinase AC, SEQ ID NO: 5, and Chondroitinase B, SEQ ID NO: 12, are provided. Other mammalian enzymes mutants with chondroitinase-like activity may independently include such enzymes as hyaluronidase 1, SEQ ID NO: 30, hyaluronidase 2, SEQ ID NO: 31, hyaluronidase 3, SEQ ID NO: 32, hyaluronidase 4, SEQ ID NO: 33, and optionally PH-20, SEQ ID NO: 34. These deletion or substitution mutant may be used alone or in combination with chondroitinases or their deletion or substitution mutants as therapeutic compositions and mixtures. Further provided is the use of these mutants, and preferably the chondroitinase deletion or substitution mutants to promote neurological functional recovery in mammals following injury to the CNS, including but not limited to contusion injury.

One embodiment of the present invention are isolated nucleic acid molecules consisting of, and preferably comprising, a nucleotide sequence encoding the amino acid sequence of polypeptides that are deletion and or substitution mutants of proteoglycan degrading molecules. Independently, nucleic acid molecules of the present invention may encode for mutant proteoglycan degrading polypeptides of chondroitinase ABC Type I, SEQ ID NO: 1, Chondroitinase ABC Type II, SEQ ID NO: 26, Chondroitinase AC, SEQ ID NO: 5, and Chondroitinase B, SEQ ID NO: 12, hyaluronidase 1, SEQ ID NO: 30, hyaluronidase 2, SEQ ID NO: 31, hyaluronidase 3, SEQ ID NO: 32, hyaluronidase 4, SEQ ID NO: 33, or optionally PH-20, SEQ ID NO: 34 and combinations of these. Preferably the nucleic acids encode for chondroitinase deletion and or substitution mutants. The invention is also directed to nucleic acid molecules consisting of, and preferably comprising, a nucleotide sequence complementary to the above-described nucleic acid sequences. Also provided for are nucleic acid molecules at least 80%, preferably 85% or 90%, still more preferably 95%, 96%, 97%, 98%, or 99% identical to any of the above-described nucleic acid molecules. Also provided for are nucleic acid molecules which hybridize under stringent conditions to any of the above-described nucleic acid molecules. The present invention also provides for recombinant vectors comprising these nucleic acid molecules, and host cells transformed with such vectors.

Also provided are isolated polypeptides consisting of, and preferably comprising, the amino acid sequence of deletion and or substitution mutants of proteoglycan degrading polypeptides. Independently, proteoglycan degrading polypeptides can include chondroitinase ABC Type I, SEQ ID NO: 1, Chondroitinase ABC Type II, SEQ ID NO: 26, Chondroitinase AC, SEQ ID NO: 5, and Chondroitinase B, SEQ ID NO: 12, hyaluronidase 1, SEQ ID NO: 30, hyaluronidase 2, SEQ ID NO: 31, hyaluronidase 3, SEQ ID NO: 32, hyaluronidase 4, SEQ ID NO: 33, optionally PH-20, SEQ ID NO: 34. Preferably the polypeptides are deletion mutants of chondroitinases. Pharmaceutical compositions may be prepared from the mutant proteoglycan degrading molecules such as chondroitinases and or hyaluronidases; the composition may include one or more of the deletion and substitution mutants from different proteoglycan degrading polypeptides.

In one aspect of the invention, biologically active proteoglycan degrading polypeptide are provided having a deletion or substitution of at least one amino acid. The mutant proteoglycan degrading polypeptides include those having the minimal size yet retain a degree of activity as determined by the enzyme assays described in the specification. Preferred deletion or substitution mutants of the proteoglycan degrading molecule are those which degrade chondroitin and have one or more amino acid deletions from the N-terminus, about 1-120 amino acids and/or the C-terminus, about 1-275 amino acids, more preferably the deletions are from a chondroitinase.

One aspect of this invention are deletion and or substitution mutants of proteoglycan degrading polypeptides, preferably deletion mutants of chondroitinase polypeptides, that promote neurite regeneration and or plasticity in the CNS and or promote or inhibit the diffusion of therapeutic molecules into tissues by degradation of proteoglycans.

The mutant proteoglycan degrading polypeptides, preferably deletion and or substitution mutants of chondroitinases, may promote neurite regeneration in the CNS and or promote or inhibit the diffusion of therapeutic molecules into tissues by degradation of proteoglycans and can be obtained through expression of suitably modified DNA sequences. Thus, the present invention also provides suitable expression vectors and host cells compatible therewith.

In yet other aspects, the invention comprises pharmaceutical compositions that include biologically active polypeptide of deletion and or substitution mutants of proteoglycan degrading molecules, and preferably deletion or substitution mutants of chondroitn degrading polypeptides as described above, in combination with a pharmaceutically acceptable carrier.

The deletion mutants and or substitution mutants of the proteoglycan degrading polypeptides of the present invention may be used to promote the regeneration of neurites in nerve tissue. These mutants might also be useful in the treatment of other CNS disorders in which plasticity, regeneration, or both might be beneficial. For example CNS injuries and disorders may include but not limited to contusion injury, traumatic brain injury, stroke, multiple sclerosis, brachial plexus injury, amblioplia. Because of their proteoglycan degrading properties, they may be used to promote the delivery of therapeutic compositions and diagnostics to tissues and cells that are normally impermeable to them. Alternatively, they may be used to inhibit penetration of therapeutic compositions, diagnositics or cells to tissues that use part of the extracellular matrix to enter tissues. Because of their smaller size compared to the full length enzyme, the deletion and or substitution mutants are easier to make and easier to deliver to target cells and tissues. These and other even smaller deletion or substitution mutants of proteoglycan degrading molecules could be used as potential therapeutics with lesser immunogenicity and similar or higher tissue penetration ability for the treatment of CNS injury.

The deletion mutants may offer significant advantages over the full length proteins in the therapeutic development process. The tissue penetration of the enzymes may be significantly effected by the protein size. The effect of protein size on tissue penetration is difficult to predict, but dependent on size and charge. The rate of penetration depends on tissue composition, charge interactions and hydration effects. Having active enzymes of widely ranging size may allow selection of an enzyme based on optimal tissue penetration properties, perhaps maximizing effective concentrations or limiting peripheral exposure to the enzyme.

The immune response of a mammal to a bacterial protein may or may not limit the ability to use the protein or polypeptide as a therapeutic. The generation of antibodies to the protein can restrict repeated exposures, as well as potentially inactivate the protein therapeutic making it ineffective. The smaller mutant proteoglycan degrading enzymes, preferably mutant chondroitinase enzymes, may limit the antigenic sites, limit an immune response or at least simplify the process of engineering an enzyme with reduced immunogenicity.

The release rate of proteins from matrices often used in sustained release formulations can be dependent upon size and cross-linking. The effective release rate of deletion mutants of proteoglycan degrading polypeptide from the matrix can be engineered through the manipulation of the size of the enzyme. Having a repertoire of chondroitinase enzymes of various size and charge will give an significant advantage for the development of a sustained release formulations.

DETAILED DESCRIPTION

Figure 1:
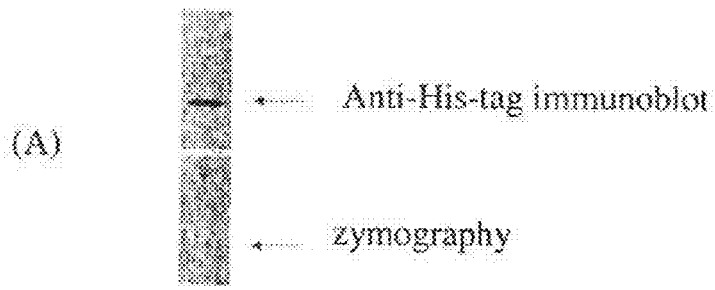
FIG. 1(A) shows Anti-His-tag Western Blot (top) and zymogram (bottom) demonstrating chondroitinase B deletion NΔ120 CΔ120 mutant (SEQ ID NO: 17) expression activity.
FIG. 1(B) shows Anti-His-tag Western Blot (top) and zymogram (bottom) demonstrating chondroitinase AC deletion NΔ50 CΔ275 mutant (SEQ ID NO: 11) expression activity.
Figure 1:
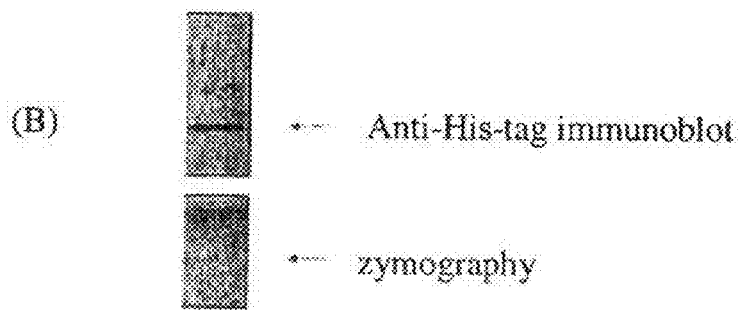

Before the present compositions and methods are described, it is to be understood that this invention is not limited to the particular molecules, compositions, methodologies or protocols described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural references unless the context clearly dictates otherwise. Thus, for example, reference to a "cell" is a reference to one or more cells and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

"Optional" or "optionally" means that the subsequently described event or circumstance may or may not occur, and that the description includes instances where the event occurs or material is present and instances where the event does not occur or where the material is not present.

One aspect of the present disclosure relates to a series of deletion and or substitution mutants of chonchoitinase genes that can be used to generate deletion mutant enzymes with substantially lower molecular weight, but modified, and preferably equivalent or superior proteoglycan degrading catalytic activity compared to the wild type enzymes. The deletion and or substitution mutants can be generated by polymerase chain reaction. The resulting mutants are expressed and then enzymatic activity of the mutant polypeptide can be confirmed by using zymography.

The mutants of the proteoglycan degrading molecules s can be used to treat mammalian CNS injuries, typically caused by trauma or disease. In particular, a deletion mutant of a proteoglycan degrading molecule like chondroitinase ABC Type I, (SEQ ID NO: 1), Chondroitinase ABC Type II, (SEQ ID NO: 11), Chondroitinase AC, (SEQ ID NO: 5), and Chondroitinase B, (SEQ ID NO: 12), or mammalian enzymes with chondroitinase-like activity such as hyaluronidase 1, (SEQ ID NO: 30), hyaluronidase 2, (SEQ ID NO: 31), hyaluronidase 3, (SEQ ID NO: 32), hyaluronidase 4, (SEQ ID NO: 33), and optionally PH-20, (SEQ ID NO: 34), or mixtures of any of these may be used to provide a therapeutic treatment for CNS injuries and disorders which may include but not limited to contusion injury, traumatic brain injury, stroke, multiple sclerosis, brachial plexus injury, amblioplia, spinal cord injuries. Spinal cord injuries includes disease and traumatic injuries, such as the crushing of neurons brought about by an auto accident, fall, contusion, or bullet wound, as well as other injuries. Practice of the present methods can confer clinical benefits to the treated mammal, providing clinically relevant improvements in at least one of the subject's motor coordination functions and sensory perception. Clinically relevant improvements can range from a detectable improvement to a complete restoration of an impaired or lost function of the CNS.

Mutants of proteoglycan degrading molecules, for example the deletion mutants of Chondroitinase AC (SEQ ID NO: 5), may have their enzyme activity stabilized by the addition of excipients or by lyophilization. Stabilizers may include carbohydrates, amino acids, fatty acids, and surfactants and are known to those skilled in the art. Examples include carbohydrates such as sucrose, lactose, mannitol, and dextran, proteins such as albumin and protamine, amino acids such as arginine, glycine, and threonine, surfactants such as TWEEN® and PLURONIC® salts such as calcium chloride and sodium phosphate, and lipids such as fatty acids, phospholipids, and bile salts. The stabilizers may be added to the proteoglycan degrading polypeptide deletion mutants in a ratio of 1:10 to 4:1, carbohydrate to polypeptide, amino acids polypeptide, protein stabilizer to polypeptide, and salts to polypeptide 1:1000 to 1:20; surfactant to polypeptide; and 1:20 to 4:1, lipids to polypeptide. Other stabilizers include high concentrations of ammonium sulfate, sodium acetate or sodium sulfate, based on comparative studies with heparinase activity. The stabilizing agents, preferably the ammonium sulfate or other similar salt, are added to the enzyme in a ratio of 0.1 to 4.0 mg ammonium sulfate/IU enzyme.

The proteoglycan degrading mutant polypeptides may be formulated as compositions and can be administered topically, locally or systemically to a subject or patient. Preferably the subject is a mammal and even more preferably a human in need of a proteoglycan degrading composition such as one of the chondroitinases. Topical or local administration is can be used for greater control of application. One or more proteoglycan degrading mutant polypeptides, singularly or in combination, can be mixed with an appropriate pharmaceutical carrier prior to administration. Examples of generally used pharmaceutical carriers and additives are conventional diluents, binders, lubricants, coloring agents, disintegrating agents, buffer agents, isotonizing agents, preservants, anesthetics and the like. Specifically pharmaceutical carriers that may be used are dextran, serum albumin, gelatin, creatinine, polyethylene glycol, non-ionic surfactants (e.g. polyoxyethylene sorbitan fatty acid esters, polyoxyethylene hardened castor oil, sucrose fatty acid esters, polyoxyethylene polyoxypropylene glycot) and similar compounds.

Compositions of the present invention having a proteoglycan degrading polypeptide or a nucleic acid for expressing it may also include therapeutic molecules, diagnostics, and agents for promoting neurite growth and regeneration. Examples of diagnostic molecules may include but are not limited to fluorescent probes, radioisotopes, dyes, or magnetic contrast agents. Compounds that facilitate plasticity, neurite growth, and regeneration can include but are not limited to molecules that over come neurite out growth inhibition, or promote nerve growth such as soluble NOGO antagonists like $NgR_{27-311}$, neural cell adhesion molecules like L1, neurotrophic factors, growth factors, phosphodiesterase inhibitors, and inhibitors of MAG or MOG. Additionally, deletion mutants may be combined with other compounds that promote remyelination such as neuregulins (GGF2) and antibodies that promote remyelination.

Plasticity of the nervous system refers to any type of functional reorganization. This reorganization occurs with development, learning and memory and brain repair. The structural changes that occur with plasticity may include synapse formation, synapse removal, neurite sprouting and may even include strengthening or weakening existing synapses. Regeneration is generally differentiated from plasticity by the long range growth of axons in disrupted tracts that is characteristic of regeneration.

Figure 2:
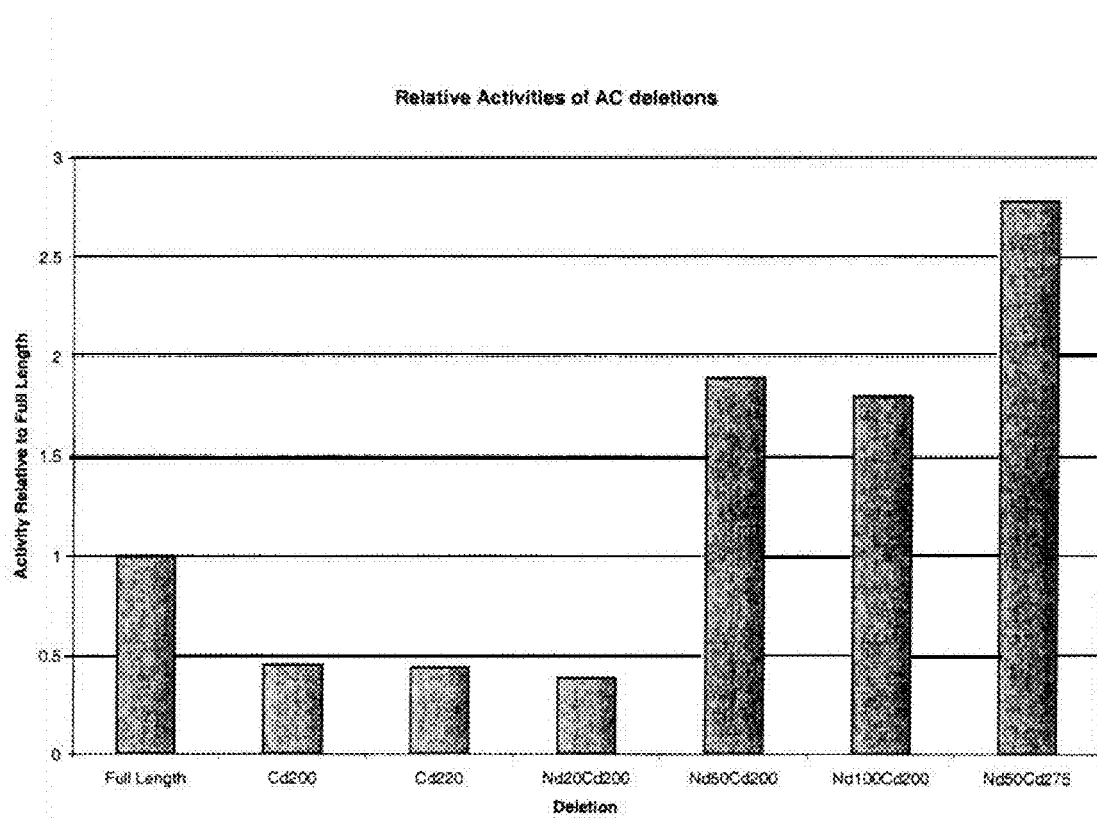
FIG. 2 shows illustrates the relative substrate degrading activity of various detetion mutant polypeptides of Chondroitinase AC (SEQ ID NO: 6-11) relative to the full length Chondroitinase AC SEQ ID NO: 5.

The biological activity of the proteoglycan degrading molecules of the present invention may be used to control the degradation rate of proteoglycans in a tissue, and for example be chosen to have a slower degradation activity for sensitive tissues and a higher degradation rate for degrading portions of tissue which are thicker. The activity may be controlled by one of more amino acid substitutions or deletions in the polypeptide or vectors used to express them; the activity may be controlled by the concentration or combination of proteoglycan degrading polypeptides in a composition. The proteoglycan degrading activity may be made to be greater or less than that of the full length polypeptide. For example, it can be made to be less than that of the full length Chondroitinase AC (SEQ ID NO: 5), and can be made to be less than half as active as the full length polypeptide as shown in FIG. 2. Also, as further illustrated in FIG. 2, the proteoglycan degrading activity can be made to be greater than the full length Chondroitinase AC (SEQ ID NO: 5), it can be made more active than the full length polypeptide by a factor of 1.5 or more; it can be more active than the full length polypeptide by a factor of 2.5 or more.

Native or wild-type *P. vulgaris* bacterial strains typically can be used to produce chondroitinases ABC I, (SEQ ID NO: 1), and chondroitinase ABC II, (SEQ ID NO: 27), and mutants of these full length polypeptide under ordinary growth conditions. Wild-type strains of *P. vulgaris* can be induced to produce detectable levels of chondroitinase ABC I and its mutants by providing an inducing substrate, such as chondroitin sulfate, as the sole carbon source. Cloned chondroitinase ABC I, (SEQ ID NO: 22), chondroitinase ABC II, (SEQ ID NO: 26), and mutants of these genes in *E. coli* can be expressed using a heterologous expression system with an artificial inducer. Chondroitinase AC (SEQ ID NO: 22), and chondroitinase B (SEQ ID NO: 26), and their mutants may be cloned from *F. heparinum* and expressed in *E. coli*.

The full length proteoglycan degrading molecules like Chondroitinase AC (SEQ ID NO: 5), as well as the deletion and or substitution mutants of the proteoglycan degrading polypeptides may be cloned in a number of bacterial as well as mammalian expression vectors. Non-limiting of these vectors include pET15b, pET14b, pGEX 6P1, pDNA4HisMax, or pSECTag2b. The deletion mutants and substituted polypeptides of the present invention exhibit the ability to degrade proteoglycans such as chondroitin CS and DS, and have a smaller size and molecular weight than the mature enzyme polypeptides which is expected to facilitate their diffusion into cells, tissues and across membranes. Expression vectors can include the nucleic acid sequence that expresses a mutant proteoglycan degrading polypeptide operably linked to an expression control sequence. Operably linked can refer to a linkage between an expression control sequence and coding sequence, where the linkage permits the expression control sequence to control the expression of the coding sequence.

The properties of the naturally occurring, substituted and or deletion mutants of the proteoglycan degrading molecules may be altered by introducing a variety of mutations in the protein. Such alterations are suitably introduced using the mutagenesis techniques, for example but not limited to PRC mutagenesis, and the mutated polypeptides molecules suitably synthesized using the expression vectors.

Mutant proteoglycan degrading polypeptides of the present invention include deletions and or substitutions of amino acids from mature proteoglycan degrading polypeptides. Preferably the deletions or substitutions include any two consecutive or separated amino acids, N or C terminal amino acid deletions or substitutions, and internal amino acid deletions or substitutions in the polypeptide. The deletions and or substitutions can start with any amino acid in the molecule and it is possible to have two separated deletions in the molecule. The deletion or substitution results in mutant proteoglycan degrading polypeptide that are smaller than the mature enzyme and retain proteoglycan degrading ability. Mutant proteoglycan degrading polypeptides can be fused or linked to another polypeptide. Polypeptide is used to unambiguously encompases amino acid sequences for mutants of any length which have proteoglycan degrading activity and improve plasticity including those minus the signal sequence that is initially part of polypeptide when it is translated and that is cleaved off by a host-translational modification.

Mutant nucleic acids of the present invention include deletions and or substitutions of nucleotides from genes which express the mature proteoglycan degrading polypeptides. The deletion and substitution mutations at the DNA level are used to introduce amino acid substitutions and or deletions into the encoded protein. These nucleotide deletions and substitutions can be used to introduce deletions and or substitutions into important conformational or active regions of the polypeptide. A nucleic acid fragment is a nucleic acid having fewer nucleotides than the nucleotide sequence encoding the entire amino acid sequence of a mature proteoglycan degrading polypeptide, yet which preferably encodes a mutant polypeptide which retains some biological activity of the full length protein, e.g., the expressed polypeptide fragment retains the ability to induce degradation of proteoglycans, promote diffusion of therapeutics into cells and tissue, or promote regeneration of neurites. Genes encoding either N or C terminal mutants of proteoglycan degrading polypeptide domains linked to other polypeptides can also be used in constructs for expression of fusion proteins linked to mutant proteoglycan degrading polypeptides.

The deletion and or substitution mutant proteoglycan degrading polypeptides of the present invention may also include derivatives of these polypeptides which have been chemically or enzymatically modified, but which retain their biological activity to degrade proteoglycans. The proteoglycan degrading activity of these mutants may be controlled depending upon the deletion and or substitution made to the polypeptide or the nucleic acid used to express the polypeptide. Variants, fragments, or analogs of the mature proteoglycan degrading polypeptides or nucleic acids and vectors used to express them include mutant polypeptides and nucleic acids having a sequence which differs from the mature polypeptide or nucleic acid sequence by one or more deletions, substitutions, or a combination of both such that the mutant proteoglycan degrading polypeptides retain their biological activity and can degrade proteoglycans, and preferably degrade chondroitin sulfate proteoglycans.

Due to the degeneracy of the genetic code, one of ordinary skill in the art will recognize that a large number of the nucleic acid molecules having a sequence at least 80%, preferably 85% or 90%, still more preferably 95%, 96%, 97%, 98%, or 99% identical to a nucleic acid sequence encoding for a mutant proteoglycan degrading molecule will encode a mutant polypeptide having proteoglycan degrading activity and preferably chondroitin degrading ability. It will be further recognized that, for such nucleic acid molecules that are not degenerate variants, a reasonable number will also encode a mutant polypeptide having proteoglycan degrading activity. This is because amino acid substitutions that are either less likely or not likely to significantly effect polypeptide activity (e.g., replacing one aliphatic amino acid with a second aliphatic amino acid) to degrade proteoglycans and preferably to degrade chondroitin.

Variants included in the invention may contain individual substitutions, deletions or additions to the nucleic acid or polypeptide sequences. Such changes will alter, add or delete a single amino acid or a small percentage of amino acids in the encoded sequence. Variants are referred to as "conservatively modified variants" where the alteration results in the substitution of an amino acid with a chemically similar amino acid.

The discovery that the proteoglycan degrading activity of the deletion and substitution mutant polypeptides of the present invention can be controlled to be less, about the same, or greater than the full length proteoglycan degrading molecule has another potential advantage. A pharmaceutical composition containing the proteoglycan degrading molecules may be administered parenterally, intravenously or subcutaneously. The use of a hydrogel composed of biodegradable polymer enclosing the polypeptide and continuously releasing the polypeptide is limited by the amount of polypeptide that can be enclosed in the hydrogel. Using a deletion mutant of the polypeptide with higher specific activity implies that, on a molar basis, more of the active substance can be enclosed in the same volume, thereby increasing the time between successive administrations or possibly avoiding repeated administrations.

Purification of the polypeptide obtained after expression is dependent on the host cell and the expression construct used. Generally, the purification of proteoglycan deletion or substitution mutants can be performed in the same way as the purification of native full length polypeptides including the use of histidine-tags.

The deletion or substitution mutant proteoglycan degrading polypeptides and proteins are administered in an amount effective to degrade CSPGs. The polypeptides may be used to aid the diffusion of therapeutic and diagnostic compositions to tissues and can be used to promote the recovery of neurological function and neurite outgrowth. Once the mutant proteoglycan degrading proteins or polypeptides in the compositions have been purified to the extent desired, they may be suspended or diluted in an appropriate physiological carrier or excipient for SCI treatment or for screening assays of compositions promoting neurite growth in vitro on suitable substrates like aggrecan. In models of SCI, effective intrathecal doses of chondroitinases in rats have been about 0.06 units on alternate days for 14 days. A dose for a 70 kilogram human may be about 17 Units. At about 100 Units/milligram, this would equal about 170 micrograms. Doses of up to 20 Units appear safe in mammalian subjects like rats. Compositions may include a proteoglycan degrading mutant polypeptide, preferably mutant chondroitinase polypeptides, and more preferably still deletion mutant chondroitinase polypeptides. These compositions may also include other proteoglycan degrading molecules and deletion and or substitution mutants of them, molecules which block the action of neurite growth inhibitors, molecules which promote neurite or axon adhesion, diagnostic, therapeutic, or the proteoglycan degrading molecule mutant as part of a fusion protein. The mixture or fusion protein may be added to a carrier or pharmaceutically acceptable excipient can be injected, generally at concentrations in the range of 1 ug to 500 mg/kg of subject. Administering the agent can be by bolus injection, intravenous delivery, continuous infusion, sustained release from implants, or sustained release pharmaceuticals. Administration by injection, can be intramuscularly, peritoneally, subcutaneously, intravenously, intrathecally. Oral administration may include tablets or capsules, preferably the oral dosage is a sustained release formulation for once or twice daily administration. Percumeous administration can be once per day, and is preferably less than once per day administration. Administration to the human patient or other mammalian subject may be continued until a measurable improvement in autonomic or motor function in the patient is achieved.

The mutant proteoglycan degrading polypeptides or fusion polypeptides that include them may also be expressed or secreted by genetically modified cells. The expressed deletion or substitution proteoglycan degrading polypeptide or fusion polypeptides may be harvested and purified for a therapeutic composition, or the genetically modified cells can be implanted, either free or in a capsule, at or near the site of CNS injury or a tissue into which the controlled diffusion of therapeutic or diagnostic molecule is desired. Mutant nucleic acids for expressing mutant proteoglycan degrading polypeptides are illustrated by non-limiting examples of chondroitinase B nucleic acid mutant (SEQ ID NO: 21) which encodes for mutant polypeptide NΔ120 CΔ120 of chondroitinase B (SEQ ID NO: 21) and chondroitinase AC nucleic acid mutant (SEQ ID NO: 19) which encodes for mutant polypeptide NΔ50 CΔ275 of chondroitinase AC (SEQ ID NO: 11). A non-limiting example of a fusion nucleic acid includes a TAT-deletion mutant chondroitinase ABCI fusion DNA construct (SEQ ID NO: 23). Another example would be a nucleic acid for TAT-chondroitinase ABCI-NΔ60 SEQ ID NO: 37) and a peptide sequence for the expressed polypeptide (SEQ ID NO: 38).

Once the mutant proteoglycan degrading polypeptide are administered to cells or a tissue with CSPGs, degradation of CSPGs removes the inhibitory molecules that block neurite outgrowth, and allow the regeneration of neurites into the affected area. The removal of CSPG also promotes plasticity in the CNS. For example, the full length polypeptides of chondroitinase AC (SEQ ID NO: 5), and chondroitinase B, (SEQ ID NO: 12), degrade CS and DS, respectively, resulting in unsaturated sulfated disaccharides. Chondroitinase AC (SEQ ID NO: 5), cleaves CS at 1,4 glycosidic linkages between N-acetylgalactosamine and glucuronic acid in the polysaccharide backbone of CS. Cleavage occurs through beta-elimination in a random endolytic action pattern. Chondroitinase B (SEQ ID NO: 12) cleaves the 1,4 galactosamine iduronic acid linkage in the polysaccharide backbone of DS. The cleavage of both CS and DS occurs through a beta-elimination process which differentiates these enzymatic mechanisms from mammalian GAG degrading enzymes. Chondroitinase ABC I (SEQ ID NO: 1), chondroitinase ABC II (SEQ ID NO: 27), are exo and endo lyases that cleave both CS and DS. The removal of CS and DS from a glial scar permits the regeneration of neurite outgrowths into the injured area and promotes plasticity. For example, the proteoglycan degrading molecules illustrated in FIG. 2, Chondroitinase AC (SEQ ID NO: 5) and various mutant Chondroitinase AC (SEQ ID NO: 6-11) degrade a model proteoglycan substrate at by various amounts. Similar results are shown by in vitro zymograph for chondroitinase B (SEQ ID NO: 12) and illustrative mutants (SEQ ID NO: 13-17) in FIG. 6. It is reasonable to expect that since a proteoglycan degrading molecule like Chondroitinase ABC I (SEQ ID NO: 1) improves functional recovery in rats with contusive spinal cord injury and also facilitates the diffusion of model compounds into brain tissue, that mutant proteoglycan degrading polypeptides and compositions containing them can also improve functional recovery in mammalian subjects like rats with contusive spinal cord injury and may also facilitates the diffusion of model compounds into brain tissue.

The regeneration of the nerve cells and restoration of plasticity in the affected CNS area allows the return of motor and sensory function. Clinically relevant improvement will range from a detectable improvement to a complete restoration of an impaired or lost nervous function, varying with the individual patients and injuries. The degree of functional recovery can be demonstrated by improved corticospinal tract conduction, improved tape removal, beam walking, grid walking and paw placement following chondroitinase treatment of a dorsal column lesion. Motor skill improvement as well as autonomic function: bowel, bladder, sensory and sexual function may also be used as measures of function improvement and related to molecular structure and components in the compositions of the present invention.

A series of polynucleotides that include coding for deletion or substition mutants of proteoglycan degrading polypeptides may be generated by PCR using the full length cDNAs for the proteoglycans as templates and cloned into an expression vector such as pET 15b at the NdeI and BamHI sites for expression in *E. Coli*. After induction of gene expression with isopropyl-β-D-thiogalactopyranoside (IPTG), the bacteria can lysed by sonication with the concomitant extraction of the mutant polypeptide with a surfactant such as Triton X-114/PBS. The majority of recombinant proteoglycan degrading polypeptide may be found in the cytosolic fraction of the bacterial cell lysate and chondroitinase purification protocols can be used to obtain the mutant proteoglycan degrading enzyme with high activity at high yields. This protocol may include purification by a column having anti-His antibody to selectively bind His-tagged mutant proteoglycan degrading polypeptides and may also includes cation-exchange chromatography as a capture step and gel filtration as a polishing step. After these steps, anion exchange membrane filtration, for example Intercept Q, Millipore, can be used for endotoxin and host DNA removal. Following filtration, the proteoglycan degrading mutant polypeptides can be dialyzed into volatile buffer, pH 8.0 and lyophilized to dryness. The final product is expected to be stable at −70° C. for long term storage. The pI of the purified basic proteoglycan degrading mutant polypeptide may be determined by IEF-PAGE analysis of the samples from the crude cell lysate.

A variety of analytical methods can be used to compare the enzymatic activity of the recombinant version the deletion or substitution mutants of proteoglycan degrading polypeptides with those of full length proteoglycan degrading molecules like chondroitinase ABC I (SEQ ID NO: 1) or a commercially available form of the enzyme. The methods may also be adapted to evaluate the activity of fusion proteins including a mutant proteoglycan degrading polypeptide portion. Specific activity measurements may be obtained using an accepted spectrophotometric assay that measures the change in absorbance due to the production of reaction products from the degradation of proteoglycans. Size exclusion chromatography can be used to compare the hydrodynamic properties of the mutant enzymes.

A form of zymography can used to characterize the mature proteoglycan degrading enzyme and may be adapted for characterization of the mutants proteoglycan degrading polypeptides. Polyacrylamide gels can be polymerized in the presence of aggrecan, a substrate for proteoglycan degrading molecules like chondroitinase ABCI. The mutant proteoglycan degrading polypeptides, enzyme samples, may be resolved on the aggrecan-impregnated gels by electrophoresis in the presence of SDS. The gels can then be subjected to a renaturation step wherein the SDS can be extracted and the enzymes allowed to refold. The refolded enzyme regains activity then digests aggrecan within the gel and the resulting loss of carbohydrate in that region of the gel that can be visualized by a carbohydrate-specific stain. A similar loss of carbohydrate in the gel would be expected for equally active forms and concentration of the mutant proteoglycan degrading molecules. In the case of recombinant Chondroitinase ABCI, its activity can be visualized as a clear spot in the zymogram. The zymography results are consistent with the spectrophotometric analysis.

HPLC methods may be used for detecting the four and six sulphated disaccharides (Δ4DS and Δ6DS, respectively) liberated as a result of mutant proteoglycan degrading polypeptide digestion of CSPG. The two disaccharides can be effectively resolved by anion exchange chromatography. The HPLC assay for the quantitation of Δ4DS and Δ6DS from chromatograms is expected to yield a linear relationship proportional to the amounts injected into the HPLC. Production of Δ4DS and Δ6DS from CSPG digestion is directly related to the amount of chondroitinase specific activity as determined by the spectrophotometric assay. This assay may be used as a sensitive and accurate method to independently quantitate Δ4DS and Δ6DS released by mutant proteoglycan degrading polypeptide digestion of a variety of substrates and may also be used to determine the activity of mutant proteoglycan degrading polypeptides and fusion proteins including them.

Another functional assay that can be performed to characterize mutant proteoglycan polypeptide activity is where dorsal root ganglian (DRG) neurons are plated on aggrecan or aggrecan treated with a deletion or substitution mutant proteoglycan degrading polypeptide. It is expected that neurons plated on aggrecan will fail to adhere to the plate and extend axons. In contrast, neurons plated on aggrecan treated with a mutant proteoglycan degrading polypeptide in a composition or as part of a fusion polypeptide would be expected to adhere to the surface and extend axons. The extensive axon growth, which is observed for chondroitinase ABC I (SEQ ID NO:1) is believed to be due to the digestion of the carbohydrates on the aggrecan core protein which creates a more permissive substrate for axon growth.

Various aspects of the invention may be understood with reference to the following non-limiting examples.

EXAMPLE 1

This phrophetic example illustrates the diffusion of molecules into cells and tissue using a deletion or substitution mutant of a proteoglycan degrading polypeptide in a composition.

A brain from an adult Sprague Dawley rat may be removed from the skull and hemispheres may be soaked in buffer alone or containing about 33 U/ml of a mutant proteoglycan degrading polypeptide such as (SEQ ID NO: 9) NΔ50 CΔ200 AC ($T_{74}$-$T_{500}$) protein for 2 hours at 37° C. Hemispheres can be rinsed and immediately placed in dye such as Eosin Y (Sigma) or a saturated solution of Congo Red (Sigma) in 70% ethanol. Slabs of tissue may be cut and images acquired on a scanner. The penetration of the dyes into the brain tissue may be used as an indication of the proteoglycan degrading activity of a mutant proteoglycan degrading molecule and expectant penetration or diffusion of therapeutic and diagnostic molecules into the same type of tissue.

EXAMPLE 2

This prophetic example illustrates a Chondroitinase ABC I Assay Protocol which may be modified to measure the activity of a mutant proteoglycan degrading molecule, for example a Chondroitinase ABCI deletion mutant or a fusion proteins including a deletion and or substitution mutant of a proteoglycan degrading polypeptide.

The production of reaction products from the catalytic activity of a proteoglycan degrading molecule or fusion protein can be determined by a measurement of the absorbance of the proteoglycan degradation product at a wavelength of 232 nm. A typical reaction mixture consisted of 120 μl of reaction mixture (40 mM Tris, pH 8.0, 40 mM NaAcetate, 0.002% casein) combined with a substrate (5 μl of 50 mM chondroitin C (MW 521), chondroitin 6 $SO_4$, or dermatan sulfate) and 1.5 μl of chondroitinase ABCI (SEQ ID NO:1) or a mutant of chondroitinase like (SEQ ID NO:2). Reaction mixture aliquots of about 120 μl can be prepared at 30-37° C. for 3 min or longer. The product formation is monitored as an increase in absorbance at 232 nm as a function of time at a wavelength of 232 nm using a spectrometer. The reaction may be stopped by addition of 0.1% SDS followed by boiling for 5 minutes. The observed activity may be converted to units (μmoles of product formed per minute) using the molar absorption coefficient for the $C_4$-$C_5$ double bond formed in the reaction (3800 $cm^{-1}$ $min^{-1}$).

Knowing the molar absorption coefficient for the reaction product, measuring the change in the absorbance of the reaction product at 232 nm reading over time upon addition of a known amount of the Chondroitinase ABCI (SEQ ID NO:1) or other mutant proteoglycan degrading polypeptide to the 120 μl reaction mixture with 0002% casein and a chondroitin substrate added, the specific activity in umol/min/mg of the mutant proteoglycan degrading polypeptide can be determined. Seikagaku Chondroitinase ABC I has a specific activity under these assay conditions of about 450 μmole/min/mg.

Chondroitinase ABC I (SEQ ID NO:1), digests axon growth inhibiting chondroitin present in CNS tissue and improves functional recovery in rats having contusion spinal cord injuries. It is reasonable to expect that mutants of proteoglycan degrading molecules, such as (SEQ ID NO: 11) NΔ50 CΔ275 AC ($T_{74}$-$T_{426}$) polypeptide that show proteoglycan degrading activity may also show some regeneration of nerves, stimulate plasticity and be useful for diffusion of agents into tissues. The mode of administration, the timing of administration and the dosage are carried out such that the functional recovery from impairment of the CNS is enhanced by the promotion of neurite outgrowth and plasticity. It is reasonable to expect that once the deletion or substitution mutants of proteoglycan degrading molecules such as (SEQ ID NO: 11) NΔ50 CΔ275 AC ($T_{74}$-$T_{426}$) protein are administered, the degradation of CSPGs can remove the inhibitory molecules in tissue that block drug diffusion, block neurite outgrowth, and promote the regeneration of neurites or other therapeutics into the affected area. The regeneration and plasticity of the nerve cells into the affected CNS area may allow the return of motor and sensory function. Clinically relevant improvements will range from a detectable improvement to a complete restoration of an impaired or lost nervous function, varying with the individual patients and injuries.

EXAMPLE 3

This example shows that deletion mutants of chondroitinase are biologically active.

Recombinantly produced chondroitinases AC and B have shown efficacy in vitro by overcoming the barrier of an inhibitory substrate border, such as aggrecan and result in neurite extension for rat cortical neurons. To facilitate effective transport of the above enzymes to the injury site, deletion mutants of these chondroitinases were prepared to determine the minimally-sized polypeptides capable of degrading CSPGs. The cleavage activity of all these mutants have been screened in vitro by zymographic assay using aggrecan as substrate. A truncated polypeptide of chondroitinase AC(NΔ50-CΔ275) (SEQ ID NO:11) lacking 50 and 275 amino acids from the amino and carboxy termini respectively having a molecular weight of 38 kDa compared to 75 kDa of the full length protein was found to be about the minimal size mutant chondroitinase AC that retains activity as tested by zymography assay FIG. 4(B). However, an even smaller mutant, the deletion mutant of chondroitinase B (nΔ120-cΔ120) (SEQ ID NO:17) lacking 120 amino acids from each of the amino and carboxy termini, having a molecular weight of 26 kDa compared to 52 kDa of the full length protein has also shown to retain activity as well in zymography assay FIG. 6(B). These and other even smaller deletion mutants could be used as potential therapeutics with lesser immunogenicity and similar or higher tissue penetration ability compared to the mature enzyme and may be used for treatment of spinal cord injury.

Figure 3:
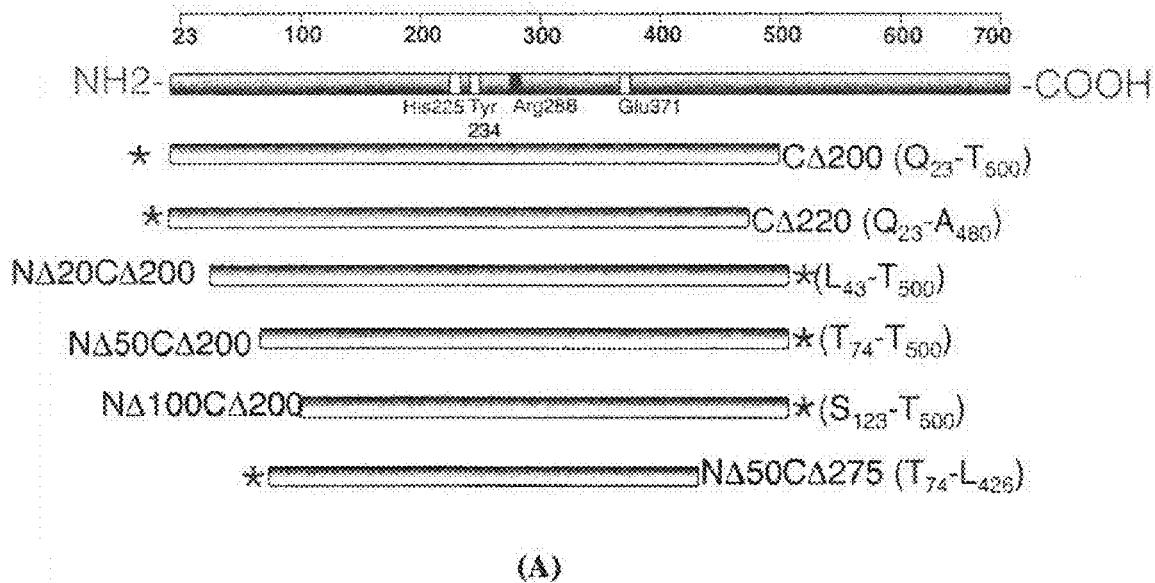
FIG. 3(A) shows a schematic of deletion mutant polypeptides of chondroitinase AC (SEQ ID NO: 6-11)
FIG. 3(B) shows confirmation of chondroitinase AC deletion mutants by Western blotting.
Figure 3:
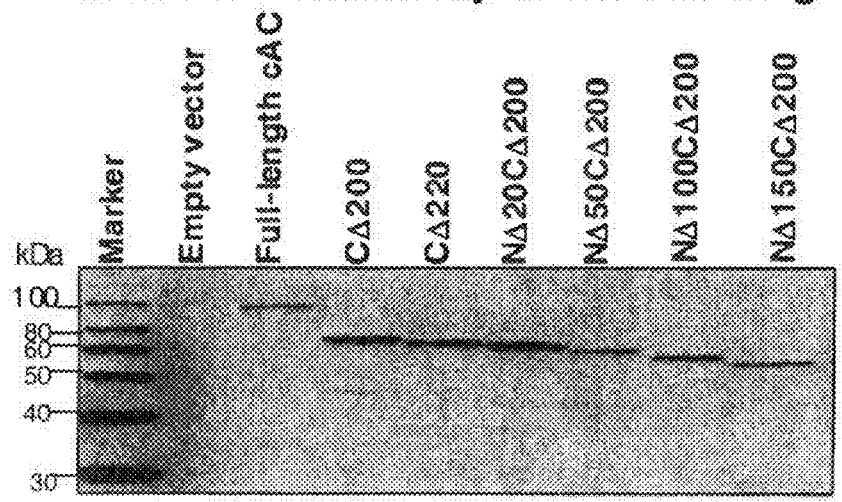
Figure 5:
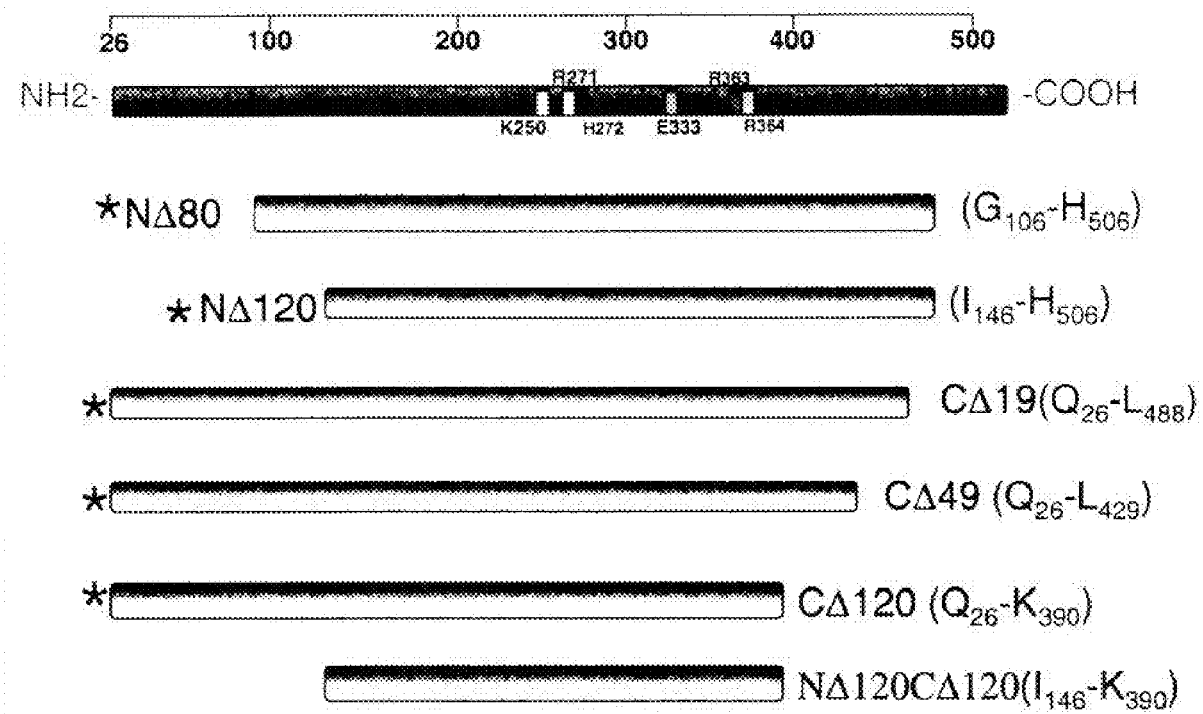
FIG. 5 shows a schematic of deletion mutant polypeptides (SEQ ID NO: 13-17) of chondroitinase B (SEQ ID NO: 12)
Figure 6:
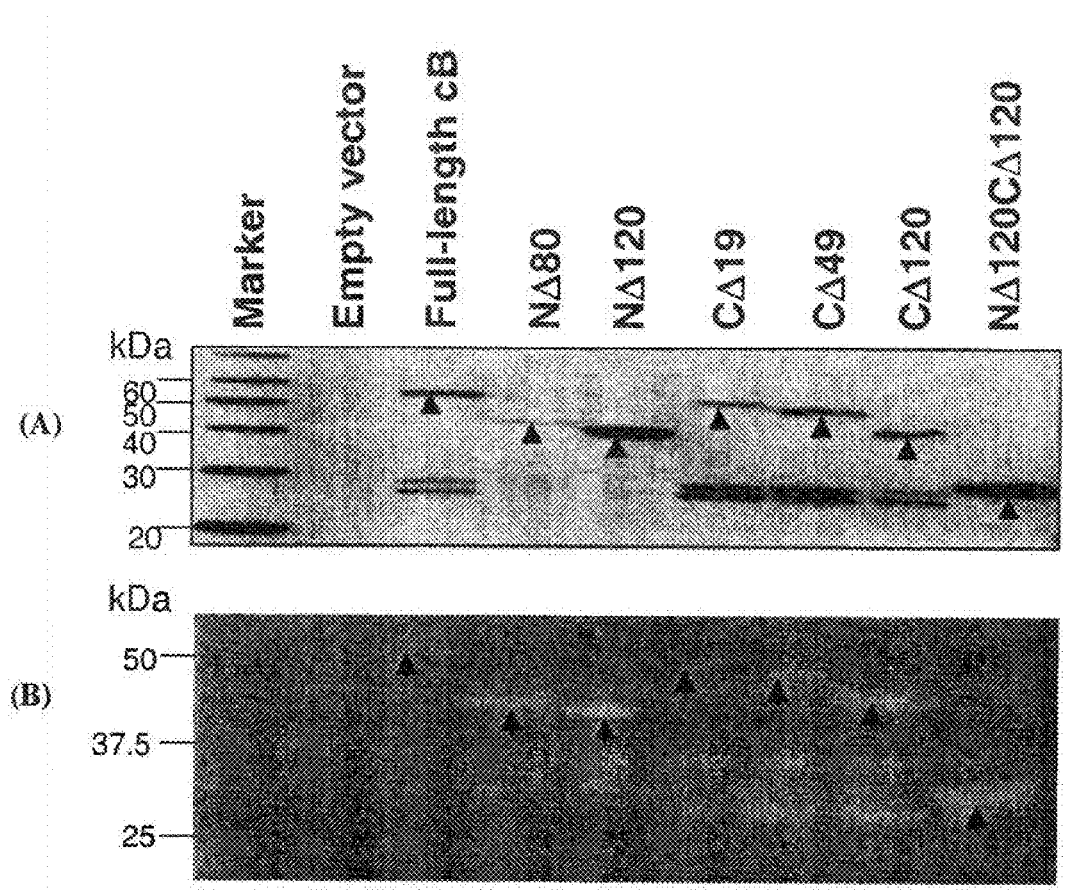
FIG. 6 shows confirmation of protein expression and catalytic activity of Chondroitinase B and deletion mutants (SEQ ID NO: 12-17) by (A) Western Blotting and (B) zymography.

A series of chondroitinase AC and B deletion mutants were generated by PCR using the full-length cDNAs for chondroitinases AC and B as templates and cloned in the pET15b expression vector at the NdeI and BamHI sites, Full length and deletion mutants were constructed with Histidine-tags for ease of detection and purification. Each of these cDNAs was induced by Isopropyl-β-D-Thiogalactopyranoside (IPTG,) and the expression was confirmed by Western blotting using anti-His antibody (Novagen). FIG. 3(A) show various non-limiting deletion mutants schematically, and FIG. 3(B) shows confirmation of expression of these chondroitinase AC mutant polypeptides by anti-histidine tag Western blotting. FIGS. 5 and 6 show the same information for chondroitinase B deletions. Western blots demonstrate proteins of predicted size. Zymographic PAGE of deletion mutants show intense bands of substrate digestion (light) and negative carbohydrate staining.

Figure 4:
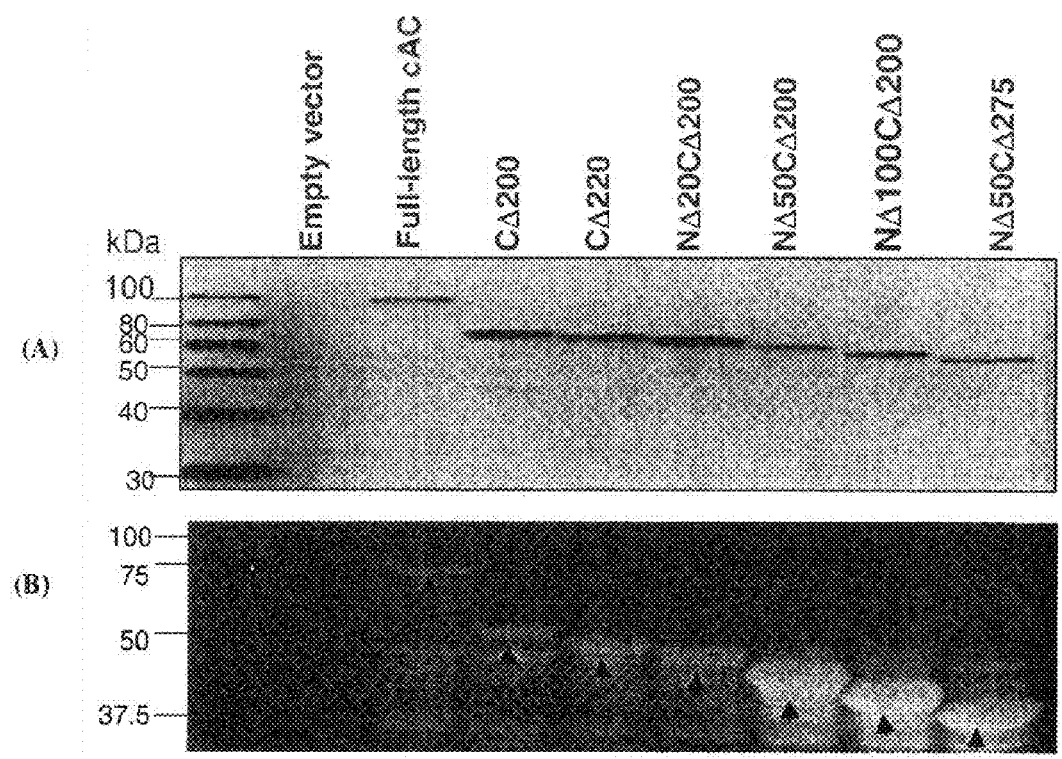
FIG. 4. shows confirmation of protein expression and catalytic activity of Chondroitinase AC deletion mutants (SEQ ID NO: 6-11) by (A) Western Blotting and (B) zymography.

Zymography assay. SDS-polyacrylamide gels were poured with aggrecan (85 µg/ml) polymerized into it. Crude extracts of deletion mutants of chondroitinases AC and B were run and renatured at 37° C. overnight. After separation the gel is incubated in 0.2% Cetylpyridinium for 90 minutes at room temperature. The digestion of the proteoglycans by the chondroitinases is visualized by staining the gel with 0.2% Toludene Blue in ethanol-$H_2O$-acetic acid (50:49:1 v/v/v) for 30 minutes and destained with ethanol-$H_2O$-acetylc acid (50:49:1 v/v/v). Following destaining the gel is incubated overnight in a 50 µg/ml solution of Stains-all in 50% ethanol in the dark and destained with $H_2O$. Appearance of clear bands on the gel shows the digestion of carboyhydrates by the chondroitinases of the CSPG leaving the core protein which remains unstained (FIG. 4. and FIG. 6).

EXAMPLE 4

This example describes the linking of a His tag to a mutant proteoglycan degrading polypeptide.

Deletion mutants of the chondroitinase ABC I enzyme where the mutant is missing a certain number of amino acids from the N-terminal and maintains proteoglycan degrading activity were generated (SEQ ID NO:2-4). These N-terminal deletion maintain a histidine-tag that is attached to the N-terminus; however similarly tagged full length chondroitinase ABC I (SEQ ID NO:1) did not maintain the histidine-tag after expression.

Figure 7:
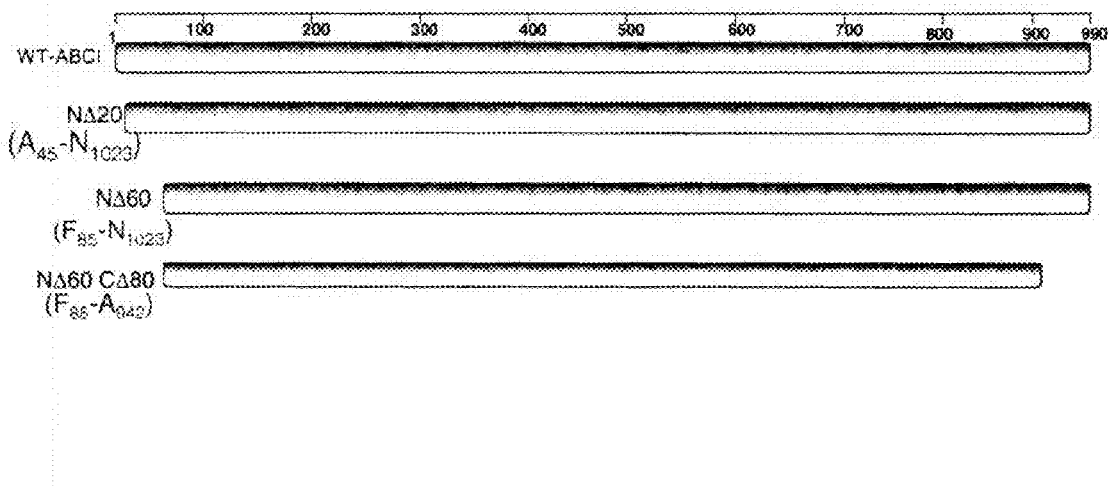
FIG. 7 shows a schematic of Chondroitinase ABC I deletion mutant polypeptides (SEQ ID NO: 2-4) of Chondroitinase ABC I SEQ ID NO: 1.

Catalytically active deletion mutants of chondroitinase ABC I can be prepared for example but not limited to deleting 20, and 60 amino acids respectively from the N-terminus of the mature ABC I protein as shown for ILLUSTRATIVE PURPOSES ONLY in FIG. 7. In addition, deletion of 80 amino acids from the C-terminal end (SEQ ID NO:38) yields a mutant of chondroitinase ABC I which has proteoglycan degrading activity as tested in a zymography assay. As a potential alternative to the full-length chondroitinase ABC I, a deletion mutant such as ABCI-NΔ20-CΔ80 with a predicted molecular weight of 89 kDa can also be made (SEQ ID NO:39).

These chondroitinase deletion mutants and mutants of other proteoglycan degrading molecules may used for construction of N-terminal fusion chimeric protein. Assay tests with these fusion polypeptides for chondroitin degradation and may be used to determine the efficacy of mature ABCI versus various deletion mutant in compositions and fusion proteins with respect to the substrate specificity, substrate binding and tissue penetration. Functional assay that can be performed to characterize the activity of mutant proteoglycan polypeptide or fusion polypeptides including them. In this functional assay, dorsal root ganglian (DRG) neurons can be plated on aggrecan or aggrecan treated with a mutant proteoglycan degrading polypeptide or a fusion polypeptide including the mutant. It is expected that neurons plated on aggrecan will failed to adhere to the plate and extend axons. In contrast, neurons plated on aggrecan treated with a mutant proteoglycan degrading polypeptide or a fusion polypeptide including the mutant in a composition or as part of a fusion polypeptide would be expected to adhere to the surface and extend axons. The extensive axon growth, which is observed for chondroitinase ABC I (SEQ ID NO:1) treated aggrecan substrate is believed to be due to the digestion of the carbohydrates on the aggrecan core protein which creates a more permissive substrate for axon growth.

EXAMPLE 5

This phrophetic example describes a mutant of chondroitinase ABC I that has native protein structure, but lacks proteoglycan degrading catalytic activity.

This mutant may be prepared as a null or a negative control for bioassays and SCI studies. Based on the crystal structure of chondroitinase ABC I a site-specific mutant designated H501a and Y508a (SEQ ID NO: 36) to knock out catalytic activity in the putative active site can be prepared. Such mutants can be tested for inactivation of catalytic activity and SEC to compare to the wild-type enzyme. The null activity mutant can also be used to provide a negative control for the various proteoglycan degrading fusion proteins for use in bioassays and ultimately in SCI animal studies.

EXAMPLE 6

This example illustrates examples of mutant proteoglycan degrading polypeptides that include both substitution and deletions from polypeptides of the present invention.

The chondroitinase ABC I sequence (SEQ ID NO: 37) is a published sequence for a mature chondroitinase ABC I peptide and includes the leader sequence. Chondroitinase ABC I sequence (SEQ ID NO: 37) is similar to (SEQ ID NO: 1), however (SEQ ID NO: 1) does not have the first 25 amino acids of (SEQ ID NO: 37), and amino acids at positions 154 and 195 of (SEQ ID NO: 37) differ from those (substitutions) found in similar positions when (SEQ ID NO: 1) and (SEQ ID NO: 37) are aligned.

(SEQ ID NO: 38-40) illustrate deletions from either the N or C terminal of the (SEQ ID NO: 37) polypeptide and substitutions relative to (SEQ ID NO: 1). These mutant polypeptides are NΔ20 (SEQ ID NO: 38), NΔ60 (SEQ ID NO: 39) and NΔ60 CΔ80 (SEQ ID NO: 40).

EXAMPLE 7

This example illustrates non-limiting illustrations of mutant polypeptides of the present invention fused with a membrane transduction polypeptide such as but not limited to a polypeptide portion of a HIV TAT protein. Full sequence listings for the mutants fusion polypeptides are provided in the Sequence listing included in the specification.

A nucleotide sequence for TAT-chondroitinase ABCI-nΔ20 (SEQ ID NO. 41), a portion of which is illustrated below, shows the TAT sequence nucleotides highlighted by underlining linked to chondroitinase nucleotides.

```
 1  ggtc gtaaaagcg tcgtcaacgt cgtcgtcctc ctcaatgcgc acaaaataac 61  ccattagcag acttctcatc agataaaaac tcaatactaa cgttatctga taaacgtagc
```

The underlined nucleotides in this portion of the nucleic acid sequence denote a TAT sequence attached to the 5' of chondroitinase ABC I-NΔ20 nucleic acid (SEQ ID NO. 47).

An amino acid sequence for TAT-chondroitinase ABCI-nΔ20 (SEQ ID NO. 42), a portion of which is shown below, illustrates the TAT sequence amino acids highlighted by underlining at the N-terminus of chondroitinase ABCI-NΔ20 (SEQ ID NO. 2).

<u>grkkrrqrrrppq</u>caqnnpladfssdknsiltlsdkrsimgnqsllwkwk
ggssfglhkkliwptdkeaskawgrsstpvfsfwlynekpidgyltidfg
eklistseaqagfkvkldftgwrtvgvslnndlenremtlnatntssdgt
qdsigrslgakvdsirfkapsnvsqgeiy A nucleotide sequence for TAT-ABCI-NΔ60 (SEQ ID NO. 43), a portion of which is illustrated below, shows the N-terminal TAT (SEQ ID NO. 49) nucleotides highlighted by underlining.

<u>ggtcgtaaagcgtcgtcaacgtcgtcgtcctcctcaatgct</u>ttactttac
ataaaaaactgattgtccccaccgataaagaagcatctaaagcatgggga
cgctcatccaccccgttttctcattttggctttacaatgaaaaaccgat
tgatggttatcttactatcgatttcgg . . .

Amino acid sequence for TAT-ABCI-nΔ60 (SEQ ID NO. 44) a portion of which is shown below, illustrates the TAT sequence (SEQ ID NO. 50) highlighted by underlining at the N-terminus of chondroitinase ABC I-NΔ60 (SEQ ID NO. 3).

<u>grkkrrqrrrppqc</u>ftlkkklivptdkeaskawgrsstpvfsfwlynekp
idgyltidfgeklistseaqagfkvkldftgwrtvgvslnndlenremtl -continued
natntssdgtqdsigrslgakvdsirfkapsnvsqgeiyidrimfsvdda
ryqwsdyqvktrlseqeiqf . . .

Nucleotide sequence for ABCI-TAT-C (SEQ ID NO. 45), a portion of which is illustrated below, shows the C-terminal TAT sequence nucleotides highlighted by underlining. The stop codon from chondroitinase ABC I (SEQ ID NO. 28) was replaced by the TAT sequence and was placed at the 3' end of the TAT sequence.

. . . gattaatggcaaatggcaatctgctgataaaaatagtgaagtga
aatatcaggtttctggtgataacactgaactgacgtttacgagttacttt
ggtattccacaagaaatcaaactctcgccactccct <u>ggtcgtaaaaagc</u>
<u>gtcgtcaacgtcgtcgtcctcctcaatgct</u>ag Amino acid sequence for ABCI-TAT-C (SEQ ID NO. 46), a portion of which is shown below, illustrates the TAT sequence highlighted by underlining at the C-terminus of the mature chondroitinase ABC I (SEQ ID NO. 1).

. . . aekvnvsrqhqvsaenknrqptegnfssawidhstrpkdasyey
mvfldatpekmgemaqkfrennglyqvlrkdkdvhiildklsnvtgyafy
qpasiedkwikkvnkpaivmthrqkdtlivsavtpdlnmtrqkaatpvti
nvtingkwqsadknsevkyqvsgdnteltftsyfgipqeiklsplp<u>grkk</u>
<u>rrqrrrppqc</u>

EXAMPLE 8

This example illustrates the sequence of chondroitinase polypeptides which may be used for deletions or substitutions in mutants of the present invention.

```
SEQ ID NO: 26 Present invention Chondroitinase ABC II Nucleic acid
>_ ABC II mature 2973 nt vs.
>_ ABC II (present invention) 2974 nt
scoring matrix:, gap penalties: -12/-2
99.0% identity; Global alignment score: 11684
              10        20        30        40        50        60
806559 TTACCCACTCTGTCTCATGAAGCTTTCGGCGATATTTATCTTTTTGAAGGTGAATTACCC
       ::::::::::::::::::::::::::::::::::::::::::::::: ::::::::::::
     _ TTACCCACTCTGTCTCATGAAGCTTTCGGCGATATTTATCTTTTTGAAGGCGAATTACCC
              10        20        30        40        50        60

70        80        90       100       110       120
806559 AATACCCTTACCACTTCAAATAATAATCAATTATCGCTAAGCAAACAGCATGCTAAAGAT
       :::: :::::::::::::::::::::::::::::::::::::::::::::::::::::::
     _ AATATCCTTACCACTTCAAATAATAATCAATTATCGCTAAGCAAACAGCATGCTAAAGAT
              70        80        90       100       110       120

130       140       150       160       170       180
806559 GGTGAACAATCACTCAAATGGCAATATCAACCACAAGCAACATTAACACTAAATAATATT
       ::::::::::::::::::::::::::::::::::::::::::::::::::::::::::::
     _ GGTGAACAATCACTCAAATGGCAATATCAACCACAAGCAACATTAACACTAAATAATATT
             130       140       150       160       170       180

190       200       210       220       230       240
806559 GTTAATTACCAAGATGATAAAAATACAGCCACACGACTCACTTTTATGATGTGGATTTAT
       :::::::::::::::::::::::::::::::::::  :::::::::::::::::::::::
     _ GTTAATTACCAAGATGATAAAAATACAGCCACACCACTCACTTTTATGATGTGGATTTAT
             190       200       210       220       230       240

250       260       270       280       290       300
806559 AATGAAAAACCTCAATCTTCCCCATTAACGTTAGCATTTAAACAAAATAATAAAATTGCA
       ::::::::::::::::::::::::::::::::::::::::::::::::::::::::::::
     _ AATGAAAAACCTCAATCTTCCCCATTAACGTTAGCATTTAAACAAAATAATAAAATTGCA
             250       260       270       280       290       300
```

```
              310       320       330       340       350       360
806559 CTAAGTTTTAATGCTGAACTTAATTTTACGGGGTGGCGAGGTATTGCTGTTCCTTTTCGT
       ::::::::::::::::::::::::::::::::::::::::::::::::::::::::::::
     _ CTAAGTTTTAATGCTGAACTTAATTTTACGGGGTGGCGAGGTATTGCTGTTCCTTTTCGT
              310       320       330       340       350       360

370       380       390       400       410       420
806559 GATATGCAAGGCTCTGTGACAGGTCAACTTGATCAATTAGTGATCACCGCTCCAAACCAA
       ::::::::::::::::::: ::::::::::::::::::::::::::::::::::::::::
     _ GATATGCAAGGCTCTGCGACAGGTCAACTTGATCAATTAGTGATCACCGCTCCAAACCAA
              370       380       390       400       410       420

430       440       450       460       470       480
806559 GCCGGAACACTCTTTTTTGATCAAATCATCATGAGTGTACCGTTAGACAATCGTTGGGCA
       ::::::::::::::::::::::::::::::::::::::::::::::::::::::::::::
     _ GCCGGAACACTCTTTTTTGATCAAATCATCATGAGTGTACCGTTAGACAATCGTTGGGCA
              430       440       450       460       470       480

490       500       510       520       530       540
806559 GTACCTGACTATCAAACACCTTACGTAAATAACGCAGTAAACACGATGGTTAGTAAAAAC
       ::::::::::::::::::::::::::::::::::::::::::::::::::::::::::::
     _ GTACCTGACTATCAAACACCTTACGTAAATAACGCAGTAAACACGATGGTTAGTAAAAAC
              490       500       510       520       530       540

550       560       570       580       590       600
806559 TGGAGTGCATTATTGATCTACGATCAGATGTTTCAAGCCCATTACCCTACTTTAAACTTC
       :::::::::::::::::: :::::::::::::::::::::::::::::::::::::::::
     _ TGGAGTGCATTATTGATGTACGATCAGATGTTTCAAGCCCATTACCCTACTTTAAACTTC
              550       560       570       580       590       600

610       620       630       640       650       660
806555 GATACTGAATTTCGCGATGACCAAACAGAAATGGCTTCGAGGTATCAGCGCTTTGAATAT
       ::::::::::::::::::::::::::::::::::::::::: :: :::::::::::::::
     _ GATACTGAATTTCGCGATGACCAAACAGAAATGGCTTCGATTTATCAGCGCTTTGAATAT
              610       620       630       640       650       660

670       680       690       700       710       720
806559 TATCAAGGAATTCGTAGTGATAAAAAAATTACTCCAGATATGCTAGATAAACATTTAGCA
       ::::: ::::::::::::::::::::::::::::::::::::::::::::::::::::: 
     _ TATCAAGGAATTCGTAGTGATAAAAAAATTACTCCAGATATGCTAGATAAACATTTAGCG
              670       680       690       700       710       720

730       740       750       780       770       780
806559 TTATGGGAAAAATTGGTGTTAACACAACACGCTGATGGTTCAATCACAGGAAAAGCCCTT
       :::::::::::::::: ::  ::::::::::::::::: : ::::::::::::::::::: 
     _ TTATGGGAAAAATTGGGGTTAACACAACACGCTGATGGCTCAATCACAGGAAAAGCCCTT
              730       740       750       780       770       780

790       800       810       820       830       840
806559 GATCACCCTAACCGGCAACATTTTATGAAAGTCGAAGGTGTATTTAGTGAGGGGACTCAA
       ::::::::::::::::::::::::::::::::::::::::::::::::::::::::::::
     _ GATCACCCTAACCGGCAACATTTTATGAAAGTCGAAGGTGTATTTAGTGAGGGGACTCAA
              790       800       810       820       830       840

850       860       870       880       880       900
806559 AAAGCATTACTTGATGCCAATATGCTAAGAGATGTGGGCAAAACGCTTCTTCAAACTGCT
       ::::::::::::::::::::::::::::::::::::::::::::::::::::::::::::
     _ AAAGCATTACTTGATGCCAATATGCTAAGAGATGTGGGCAAAACGCTTCTTCAAACTGCT
              850       860       870       880       880       900

910       920       930       940       950       960
806559 ATTTACTTGGGTAGCGATTCATTATCAGCAACTGATAGAAAAAAATTAGAAGAGCGCTAT
       :::::::: : :::::::::::::::::::::::  ::::::::::::::::::::::::
     _ ATTTACTTGCGTAGCGATTCATTATCAGCAACTGGTAGAAAAAAATTAGAAGAGCGCTAT
              910       920       930       940       950       960

970       980       990      1000      1010      1020
806559 TTATTAGGTACTCGTTATGTCCTTGAACAAGGTTTTCACCGAGGAAGTGGTTATCAAATT
       :::::::::::::::::::::::::::::::::::::  : ::::::::::::::::::: 
     _ TTATTAGGTACTCGTTATGTCCTTGAACAAGGTTTTACACGAGGAAGTGGTTATCAAATT
              970       980       990      1000      1010      1020

1030      1040      1050      1060      1070      1080
806559 ATTAGCCATGTTGGTTACCAAACCACACAACTTTTTGATGCATGGTTTATTGGTCGTCAT
       :::: :::::::::::::::::::: ::::::::::::::::::::::::::: ::::::
     _ ATTACTCATGTTGGTTACCAAACCAGAGAACTTTTTGATGCATGGTTTATTGGCCGTCAT
              1030      1040      1050      1060      1070      1080

1090      1100      1110      1120      1130      1140
806559 GTTCTTGCAAAAAATAACCTTTTAGCCCCCACTCAACAAGCTATGATGTGCTACAACGCC
```

```
             1090      1100      1110      1120      1130      1140
       GTTCTTGCAAAAAATAACCTTTTAGCCCCCACTCAACAAGCTATGATGTGGTACAACGCC
             1090      1100      1110      1120      1130      1140

1150      1160      1170      1180      1190      1200
806559 ACAGGACGTATTTTTGAAAAAAATAATGAAATTGTTGATGCAAATGTCOATATTCTCAAT
       ::::::::::::::::::::::::: :::::::::::::::::::::::: :::::::::
       ACAGGACGTATTTTTGAAAAACATAATGAAATTGTTGATGCAAATGTCGATATTCTCAAT
             1150      1160      1170      1180      1190      1200

1210      1220      1230      1240      1250      1260
806559 ACTCAATTGCAATGGATGATAAAAAGCTTATTGATGCTACCGGATTATCAACAACGTCAA
       ::::::::::::::::::::::::::::::::::::::::::::::::::::::::::::
       ACTCAATTGCAATGGATGATAAAAAGCTTATTGATGCTACCGGATTATCAACAACGTCAA
             1210      1220      1230      1240      1250      1260

1270      1280      1290      1300      1310      1320
806559 CAAGCCTTAGCGCAACTGCAACGTTGGCTAAATAAAACCATTCTAAGCTCAAAAGGTGTT
       :::::::::::::::::::::::: :::::::::::::::::::::::::::::::::::
       CAAGCCTTAGCGCAACTGCAAAGTTGGCTAAATAAAACCATTCTAAGCTCAAAAGGTGTT
             1270      1280      1290      1300      1310      1320

1330      1340      1350      1360      1370      1380
806559 GCTGGCGGTTTCAAATCTGATGGTTCTATTTTTCACCATTCACAACATTACCCCGCTTAT
       ::::::::::::::::::::::::::::::::::::::::::::::::::::::::::::
       GCTGGCGGTTTCAAATCTGATGGTTCTATTTTTCACCATTCACAACATTACCCCGCTTAT
             1330      1340      1350      1360      1370      1380

1390      1400      1410      1420      1430      1440
806559 GCTAAAGATGCATTTGGTGGTTTAGCACCCAGTGTTTATGCATTAAGTGATTCACCTTTT
       ::::::::::::::::::::::::::::::::::::::::::::::::::::::::::::
       GCTAAAGATGCATTTGGTGGTTTAGCACCCAGTGTTTATGCATTAAGTGATTCACCTTTT
             1390      1400      1410      1420      1430      1440

1450      1460      1470      1480      1490      1500
806559 CGCTTATCTACTTCAGCACATGAGCGTTTAAAAGATGTTTTGTTAAAAATGCGGATCTAC
       :::::::::::::::::::::::::: :::::::::::::::::::::::::::::::::
       CGCTTATCTACTTCAGCACATGAGCATTTAAAAGATGTTTTGTTAAAAATGCGGATCTAC
             1450      1460      1470      1480      1490      1500

1510      1520      1530      1540      1550      1560
806559 ACCAAAGAGACACAAATTCCTGCTGTATTAAGTGGTCGTCATCCAACTGGGTTGCATAAA
       :::::::::::::::::::::::: :::::::::::::::::::::::::::::::::::
       ACCAAAGAGACACAAATTCCTGTGGTATTAAGTGGTCGTCATCCAACTGGGTTGCATAAA
             1510      1520      1530      1540      1550      1560

1570      1580      1590      1600      1610      1620
806559 ATAGGGATCCCGCCATTTAAATGGATGGCATTAGCAGGAACCCCAGATGGCAAACAAAAG
       ::::::::: ::::::::::::::::::::::::::::::::::::::::::::::::::
       ATAGGGATCGCGCCATTTAAATGGATGGCATTAGCAGGAACCCCAGATGGCAAACAAAAG
             1570      1580      1590      1600      1610      1620

1630      1640      1650      1660      1670      1680
806559 TTAGATACCACATTATCCGCCGCTTATGCAAAATTAGACAACAAAACGCATTTTGAAGGC
       :::::::::::::::::::::::::::::: :::: ::::::::::::::::::::::::
       TTAGATACCACATTATCCGCCGCTTATCCAAACTTAGACAACAAAACGCATTTTGAAGGC
             1630      1640      1650      1660      1670      1680

1690      1700      1710      1720      1730      1740
806559 ATTAAGGCTGAAAGTGAGCCAGTCGGCGCATGGGCAATGAATTATGCATCAATGGCAATA
       :::::  :::::::::::::::::::::::::::::::::::::::::::::::::::::
       ATTAACGCTGAAAGTGAGCCAGTCGGCGCATGGGCAATGAATTATGCATCAATGGCAATA
             1690      1700      1710      1720      1730      1740

1750      1760      1770      1780      1790      1800
806559 CAACGAAGAGCATCGACCCAATCACCACAACAAAGCTGGCTCGCCATAGCGCGCGGTTTT
       :::: ::::::::::::::::::::::::::::::::: :::::::::::::::::::::
       CAACGAAGAGCATCGACCCAATCACCACAACAAAGCTCGCTCGCCATAGCGCGCGGTTTT
             1750      1760      1770      1780      1790      1800

1810      1820      1830      1840      1850      1860
806559 AGCCGTTATCTTGTTGGTAATGAAAGCTATGAAAATAACAACCGTTATGGTCGTTATTTA
       ::::::::::::::::::::::::::::::::::::::::::::::::::::::::::::
       AGCCGTTATCTTGTTGGTAATGAAAGCTATGAAAATAACAACCGTTATGGTCGTTATTTA
             1810      1820      1830      1840      1850      1860

1870      1880      1890      1900      1910      1920
806559 CAATATGGACAATTGGAAATTATTCCAGCTGATTTAACTCAATCAGGGTTTAGCCATGCT
       ::::::::::::::::::::::::::::::::::::::::::::::::::::::::::::
       CAATATGGACAATTGGAAATTATTCCAGCTGATTTAACTCAATCAGGGTTTAGCCATGCT
             1870      1880      1890      1900      1910      1920
```

-continued

```
              1930      1940      1950      1960      1970      1980
806559 GGATGGGATTGGAATAGATATCCAGGTACAACAACTATTCATCTTCCCTATAACGAACTT
       ::::::::::::::::::::::::::::::::::::::::::::::::::::::::::::
     _ GGATGGGATTGGAATAGATATCCAGGTACAACAACTATTCATCTTCCCTATAACGAACTT
              1930      1940      1950      1960      1970      1980

1990      2000      2010      2020      2030      2040
806559 GAAGCAAAACTTAATCAATTACCTGCTGCAGGTATTGAAGAAATGTTGCTTTCAACAGAA
       ::::::::::::::::::::::::::::::::::::::::::::::::::::::::::::
     _ GAAGCAAAACTTAATCAATTACCTGCTGCAGGTATTGAAGAAATGTTGCTTTCAACAGAA
              1990      2000      2010      2020      2030      2040

2050      2060      2070      2080      2090      2100
806559 AGTTACTCTGGTGCAAATACCCTTAATAATAACAGTATGTTTGCCATGAAATTACACGGT
       :::::::::::::::::::::::::::::::::::::::: :::::::::::::::::::
     _ AGTTACTCTGGTGCAAATACCCTTAATAATAACAGTATCTTTCCCATGAAATTACACGGT
              2050      2060      2070      2080      2090      2100

2110      2120      2130      2140      2150      2160
806559 CCAAGTAAATATCAACAACAAAGCTTAAGGGCAAATAAATCCTATTTCTTATTTGATAAT
       :  :::::::::::::::::::::::::::::::::::::::::::::::::::::::::
     _ CACAGTAAATATCAACAACAAAGCTTAAGGGCAAATAAATCCTATTTCTTATTTGATAAT
              2110      2120      2130      2140      2150      2160

2170      2180      2190      2200      2210      2220
806559 AGAGTTATTGCTTTAGGCTCAGGTATTGAAAATGATGATAAACAACATACGACCGAAACA
       :::::::::::::::::::::::::::::::::::::::::::::::::::::::::::
     _ AGAGTTATTGCTTTAGGCTCAGGTATTGAAAATGATGATAAACAACATACGACCGAAACA
              2170      2180      2190      2200      2210      2220

2230      2240      2250      2260      2270      2280
806559 ACACTATTCCAGTTTGCCGTCCCTAAATTACAGTCAGTGATCATTAATGGCAAAAAGGTA
       ::::::::::::::::::::::::::::::::::::::::::::::::::::::::::::
     _ ACACTATTCCAGTTTGCCGTCCCTAAATTACAGTCAGTGATCATTAATGGCAAAAAGGTA
              2230      2240      2250      2260      2270      2280

2290      2300      2310      2320      2330      2340
806559 AATCAATTAGATACTCAATTAACTTTAAATAATGCAGATACATTAATTGATCCTGCCGGC
       ::::::::::::::::::::::::::::::::::::::::::::::::::::::::::::
     _ AATCAATTAGATACTCAATTAACTTTAAATAATGCAGATACATTAATTGATCCTGCCGGC
              2290      2300      2310      2320      2330      2340

2350      2360      2370      2380      2390      2400
806559 AATTTATATAAGCTCACTAAAGGACAAACTGTAAAATTTACTTATCAAAAACAACATTCA
       :::::::::::::::::::::::::::::::::::::::: :::::::::::::::::::
     _ AATTTATATAAGCTCACTAAAGGACAAACTGTAAAATTTAGTTATCAAAAACAACATTCA
              2350      2360      2370      2380      2390      2400

2410      2420      2430      2440      2450      2460
806559 CTTGATGATAGAAATTCAAAACCAACAGAACAATTATTTGCAACAGCTGTTATTTCTCAT
       ::::::::::::::::::::::::::::::::::::::::::::::::::::::::::::
     _ CTTGATGATAGAAATTCAAAACCAACAGAACAATTATTTGCAACAGCTGTTATTTCTCAT
              2410      2420      2430      2440      2450      2460

2470      2480      2490      2500      2510      2520
806559 GGTAAGGCACCGAGTAATGAAAATTATGAATATGGAATAGCTATCGAAGCACAAAATAAT
       :::::::::::::::::::::::::::::::::::::: :::::::::::::::::::::
     _ GGTAAGGCACCGAGTAATGAAAATTATGAATATGCAATAGCTATCGAAGCACAAAATAAT
              2470      2480      2490      2500      2510      2520

2530      2540      2550      2560      2570      2580
806559 AAAGCTCCGGAATACACAGTATTACAACATAATGATCAGCCCCATGCGGTAAAAGATAAA
       :::::::: ::::::::::::::::::::::::::::::: :::::::::::::::::::
     _ AAAGCTCCCCAAATACACAGTATTACAACATAATGATCAGCTCCATGCGGTAAAAGATAAA
              2530      2540      2550      2560      2570      2580

2590      2600      2610      2620      2630
806559 ATAACCCAAGAAGAGGGATATGCTTTTTTTGAAGCCACTAAGTTAAAATCAGCGGATGC
       :::::::::::::::::::::: :::::::::::::::::::::::::::::::::::
     _ ATAACCCAAGAAGAGGGATATGGTTTTTTTGAAGCCACTAAGTTAAAATCAGCGGATGC
              2590      2600      2610      2620      2630      2640

2640      2650      2660      2670      2680      2690
806559 AACATTATTATCCAGTGATGCGCCGGTTATGGTCATGGCTAAAATACAAAATCAGCAATT
       ::::::::::::::::::::::::::::::::::::::::::::::::::::::::::::
     _ AACATTATTATCCAGTGATGCGCCGGTTATGGTCATGGCTAAAATACAAAATCAGCAATT
              2650      2660      2670      2680      2690      2700

2700      2700      2710      2720      2730      2740
806559 AACATTAAGTATTGTTAATCCTGATTTAAATTTATATCAAGGTAGAGAAAAAGATCAATT
```

```
                  AACATTAAGTATTGTTAATCGTGATTTAAATTTATATCAAGGTAGAGAAAAAGATCAATT
                          2700      2710      2720      2730      2740      2750

2760      2770      2780      2790      2800      2810      2810
    806559 TGATGATAAAGGTAATCAAATCGAAGTTAGTGTTTATTCTCGTCATTGGCTTACAGCAGA
                  ::::::::::::::::::::::::::::::::::::::::::::::::::::::::::::
                  TGATCATAAAGGTAATCAAATCGAAGTTAGTGTTTATTCTCGTCATTGGCTTACAGCAGA
                          2770      2780      2790      2800      2810      2820

2820      2820      2830      2840      2850      2860      2870
    806559 ATCGCAATCAACAAATAGTACTATTAGCGTAAAAGGAATATGGAAATTAACGACACCTCA
                  ::::::::::::::::::::::::::::::::::::::::::::::::::::::::::::
                  ATCGCAATCAACAAATAGTACTATTAGCGTAAAAGGAATATGGAAATTAACGACACCTCA
                          2820      2830      2840      2850      2860      2880

2820      2880      2890      2900      2910      2920      2930
    806559 ACCCGGTGTTATTATTAAGCACCACAATAACAACACTCTTATTACGACAACAACCATACA
                  ::::::::::::::::::::::::::::::::::::::::::::::::::::::::::::
                  ACCCGGTGTTATTATTAAGCACCACAATAACAACACTCTTATTACGACAACAACCATACA
                          2880      2890      2900      2910      2920      2930

2940      2940      2950      2960      2970
    806559 GGCAACACCTACTGTTATTAATTTAGTTAAGTAA
                  ::::::::::::::::::::::::::::::::::
                  GGCAACACCTACTGTTATTAATTTAGTTAAGTAA
                          2990      2960      2970
```

The above discrepancies, bold text, at the nucleotide level resulted in 98.3% identity at the amino acid level and the substituted residues are marked in bold text in the following.

```
SEQ ID NO: 27 Present Invention Chondroitinase ABC II protein
>_ ABC (present invention) 990 aa vs.
>_ ABC (matare) 990 as
scoring matrix: gap penalties: -12/-2
98.3% identIty; Global alignment score: 6393
                  10        20        30        40        50        60
    457676 LPTLSHEAFGDIYLFEGELPNILTTSNNNQLSLSKQHAKDGEQSLKWQYQPQATLTLNNI
           ::::::::::::::::::::::: ::::::::::::::::::::::::::::::::::::
           LPTLSHEAFGDIYLFEGELPNTLTTSNNNQLSLSKQHAKDGEQSLKWQYQPQATLTLNNI
                  10        20        30        40        50        60

70        80        90       100       110       120
    457676 VNYQDDKNTATPLTFMMWIYNEKPQSSPLTLAFKQNNKIALSFNAELNFTGWRGTAVPFR
           :::::::::::::::::::::::::::::::::::::::::::::::::::::  :::::
           VNYQDDKNTATPLTFMMWIYNEKPQSSPLTLAFKQNNKIALSFNAELNFTGWRGIAVPFR
                  70        80        90       100       110       120

130       140       150       160       170       180
    457676 DMQGSATGQLDQLVITAPNQAGTLFFDQIIMSVPLDNRWAVPDYQTPYVNNAVNTMVSKN
           :::::.:::::.::::::::::::::::::::::::::::::::::::::::::::::::
           DMQGSVTGQLEQLVITAPNQAGTLFFDQIIMSVPLDNRWAVPDYQTPYVNNAVNTMVSKN
                 130       140       150       160       170       180

190       200       210       220       230       240
    457676 WSALLMYDQMFQAHYPTLNFDTEFRDDQTEMASIYQRFEYYQGIRSDKKITPDMLDKHLA
           :::::::::::::::::::::::::::::::::: :::::::::::::::::::::::::
           WSALLMYDQMFQAHYPTLNFDTEFRDDQTEMASRYQRFEYYQGIRSDKKITPDMLDKHLA
                 190       200       210       220       230       240

250       260       270       280       290       300
    457676 LWEKLGLTQHADGSITCRALDHPNRQEEMKVEGVFSEGTQKALLDANMLRDVGKTLLQTA
           ::::: : ::::::::  :::::::: ::::::::::::::::::::::: :::::::::
           LWEKLVLTQHADGSITGKALDHPNRQHFMKVEGVFSEGTQKALLDANMLRDGKTLLQTA
                 250       260       270       280       290       300

310       320       330       340       350       360
    457676 IYLRSDSLSATGRKKLEERYLLGTRYVLEQGFTRGSGYOIITHVGYQTRELFDAWFIGRH
           :::::::::::::::::::::::::::::::::::::::::::::::::::::::::::
           IYLRSDSLSATGRKKLEERYLLGTRYVLEQGFHRGSGYQIISHVGYQTRELFDAWFIGRH
                 310       320       330       340       350       360

370       380       390       400       410       420
    457676 VLAKNNLLAPTQQAMMWYNATGRIFEKDNEIVDANVDILNTQLQWMIKSLLMLPDYQQRQ
           ::: .:::::::::::::::::::::: ::::::::::::::::::::::::::::::::
           VLASNNLLAPTQQAMMWYNATGRIFEKNNEIVDANVDILNTQLQWMIKSLLMLPDYQQRQ
                 370       380       390       400       410       420
```

-continued

```
           430        440        450        460        470        480
457676 QALAQLQSNLNKTILSSKGVAGGFKSDGSIFHHSQEYPAYAKDAFGGLAPSVYALSDSPF
       ::::::: :::::::::::::::::::::::::: :::::::::::::::::::::::::
     _ QALAQLQRWLNKTILSSKGVAGGFKSDGSIFHHSQHYPAYAKDAFGGLAPSVYALSDSPF
           430        440        450        460        470        480

490        500        510        520        530        540
457676 RLSTSAHEHLKDVLLKNRIYTKETQIPVVLSGRHPTGLHKIGIAPFKWMALAGTPDGKQK
       :::::::::: :::::::: :::::::::: :::::::::::::::::::::::::::::
     _ RLSTSAHERLKDVLLKMRTYTKETQIPAVLSGRHPTGLHKIGIAPFKWMALAGTPDGKQK
           490        500        510        520        530        540

550        560        570        580        590        600
457676 LDTTLSAAYANLDNKTHFEGINAESEPVGAWANNYASMAIQRRASTQSPQQSWLAIARGF
       :::::::::: ::::::::::: ::::::::: :::::::::::::::::::::::::::
     _ LDTTLSAAYAKLDNKTHFEGIKAESEPVGAWAMNYASMAIQRRASTQSPQQSWLAIARGF
           550        560        570        580        590        600

610        620        630        640        650        660
457676 SRYLVGNESYENNNRYGRYLQYGQLEIIPADLTQSGFSHAGWDWNRYPGTTTIHLPYNEL
       ::::: :::::::::::::::::::::::::::::::::::::::::::::::::::::
     _ SRYLVQNESYENNNRYGRYLQYGQLEIIPADLTQSGFSHAGWDWNRYPGTTTIHLPYNEL
           610        620        630        640        650        660

670        680        690        700        710        720
457676 EAKLNQLPAAGIEEMLLSTESYSGANTLNNNSMFAMKLHGHSKYQQQSLRANKSYFLFDN
       :::::::::::::::::::::::::::::::::::::: :::::::::::::::::::::
     _ EAKLNQLPAAGIEEMLLSTESYSGANTLNNNSMFAMKLEGPSKYQQQSLRANKSYFLFDN
           670        680        690        700        710        720

730        740        750        760        770        780
457676 RVIALGSGIENDDKQHTTSTTLFQFAVPKLQSVIINGKKVNQLDTQLTLNNADTLIDPAG
       :::::::::::::::::: ::::::::::::::::::::::::::::::::::::::::
     _ RVIALGSGIENDDKQHTTETTLFQFAVPKLQSVIINGKKVNQLDTQLTLNNADTLIDPAG
           730        740        750        760        770        780

790        800        810        820        830        840
457676 NLYKLTKGQTVKFSYQKQHSLDDRNSKPTEQLFATAVISHGKAPSNENYEYAIAIEAQNN
       ::::::::::::::::::::::::::::::::::::::::::::::::::::::::::::
     _ NLYKLTKGQTVKFSYQKQHSLDDRNSKPTEQLFATAVISHGKAPSNENYEYAIAIEAQNN
           790        800        810        820        830        840

850        860        870        880        890        900
457676 KAPKYTVLQHNDQLHAVKDKITQEEGYGFFEATKLKSADATLLSSDAPVMVNAKIQNQQL
       :::.:::::::::: ::::::::::::::: :::::::::::::::::::::::::::::
     _ KAPEYTVLQHNDQPHAVKDKITQEEGYAFFEATKLKSADATLLSSDAPVMVNAKIQNQQL
           850        860        870        880        890        900

910        920        930        940        960        960
457676 TLSIVNPDLNLYQGREKDQFDDKGNQIEVSVYSRHWLTAESQSTNSTITVKGIWKLTTPQ
       ::::::::::::::::::::::::::::::::::::::::::::::::::::::::::::
     _ TLSIVNPDLNLYQGREKDQFDDKGNQIEVSVYSRHWLTAESQSTNSTITVKGIWKLTTPQ
           910        920        930        940        960        960

970        980        990
457676 PGVIIKHHNNNTLITTTTIQATPTVINLVK
       :::::::::::::::::::::::::::::
     _ PGVIIKHHNNNTLITTTTIQATPTVINLVK
           970        980        990

SEQ ID NO: 28 Present Invention Chondroitinase ABC I nucleic acid
>_ ABCI present invention 2994 nt va.
>_ ABCI mature 2994 nt
scoring matrix gap penalties: -12/-2
99.7% identity; Global aligneent score: 11909
            10         20         30         40         50         60
806659 GCCACCAGCAATCCTGCATTTGATCCTAAAAATCTGATGCAGTCAGAAATTTACCATTTT
       ::::::::::::::::::::::::::::::::::::::::::::::::::::::::::::
     _ GCCACCAGCAATCCTGCATTTGATCCTAAAAATCTGATGCAGTCAGAAATTTACCATTTT
            10         20         30         40         50         60

70         80         90        100        110        120
806659 GCACAAAATAACCCATTAGCAGACTTCTCATCAGATAAAAACTCAATACTAACGTTATCT
       ::::::::::::::::::::::::::::::::::::::::::::::::::::::::::::
     _ GCACAAAATAACCCATTAGCAGACTTCTCATCAGATAAAAACTCAATACTAACGTTATCT
            70         80         90        100        110        120

130        140        150        160        170        180
906659 GATAAACGTAGCATTATGGGAAACCAATCTCTTTTATGGAAATGGAAAGGTGGTAGTAGC
       ::::::::::::::::::::::::::::::::::::::::::::::::::::::::::::
```

-continued

```
        GATAAACGTAGCATTATGGGAAACCAATCTCTTTTATGGAAATGGAAAGGTGGTAGTAGC
            130       140       150       160       170       180

190       200       210       220       230       240
806559  TTTACTTTACATAAAAAACTGATTGTCCCCACCGATAAAGAAGCATCTAAAGCATGGGGA
        ::::::::::::::::::::::::::::::::::::::::::::::::::::::::::::
_       TTTACTTTACATAAAAAACTGATTGTCCCCACCGATAAAGAAGCATCTAAAGCATGGGGA
            190       200       210       220       230       240

250       260       270       280       290       300
806559  CGCTCATCCACCCCCGTTTTCTCATTTTGGCTTTACAATGAAAAACCGATTGATGGTTAT
        :::::::::: :::::::::::::::::::::::::::::::::::::::::::::::::
_       CGCTCATCTACCCCCGTTTTCTCATTTTGGCTTTACAATGAAAAACCGATTGATGGTTAT
            250       260       270       280       290       300

310       320       330       340       350       360
806559  CTTACTATCGATTTCGGAGAAAAACTCATTTCAACCAGTGAGGCTCAGGCAGGCTTTAAA
        :::::::::::::::::::::::::::::::::::::::::::::::::: :::::::::
_       CTTACTATCGATTTCGGAGAAAAACTCATTTCAACCAGTGAGGCTCAGGCACGCTTTAAA
            310       320       330       340       350       360

370       380       390       400       410       420
806559  GTAAAATTAGATTTCACTCGCTGGCGTACTGTGGGAGTCTCTTTAAATAACGATCTTGAA
        :::::: ::::::::::: :::::::: ::::::::::::::::::::::::::::::::
_       GTAAAATTAGATTTCACTGGCTGGCGTGCTGTGGGAGTCTCTTTAAATAACGATCTTGAA
            370       380       390       400       410       420

430       440       450       460       470       480
806559  AATCGAGAGATGACCTTAAATGCAACCAATACCTCCTCTGATGGTACTCAAGACAGCATT
        ::::::::::::::::::::::::::::::::::::::::::::::::::: ::::::::
_       AATCGAGAGATGACCTTAAATGCAACCAATACCTCCTCTGATGGTACTCAACACAGCATT
            430       440       450       460       470       480

490       500       510       520       530       540
806559  GGGCGTTCTTTAGGTCCTAAAQTCGATAGTATTCGTTTTAAAGCGCCTTCTAATGTGAGT
        :::::::::::::: ::::: ::::::::::::::::::::::::::::::::::::::
_       GGGCGTTCTTTAGGTGCTAAAGTCGATAGTATTCGTTTTAAAGCGCCTTCTAATGTGAGT
            490       500       510       520       530       540

550       560       570       580       590       600
806559  CAGGGTGAAATCTATATCGACCGTATTATGTTTTCTGTCGATGATGCTCGCTACCAATGG
        ::::::::::::::::::::::::::::::::::::::::::::::::::::::::::::
_       CAGGGTGAAATCTATATCGACCGTATTATGTTTTCTGTCGATGATGCTCGCTACCAATGG
            550       560       570       580       590       600

610       620       630       640       650       660
806559  TCTGATTATCAAGTAAAAACTCGCTTATCAGAACCTGAAATTCAATTTCACAACGTAAAG
        ::::::::::::::::::::::::::::::::::::::::::::::::::::::::::::
_       TCTGATTATCAAGTAAAAACTCGCTTATCAGAACCTGAAATTCAATTTCACAACGTAAAG
            610       620       630       640       650       660

670       680       690       700       710       720
806859  CCACAACTACCTGTAACACCTGAAAATTTAGCGGCCATTGATCTTATTCGCCAACGTCTA
        ::::::::::::::::::::::::::::::::::::::::::::::::::::::::::::
_       CCACAACTACCTGTAACACCTGAAAATTTAGCGGCCATTGATCTTATTCGCCAACGTCTA
            670       680       690       700       710       720

730       740       750       760       770       780
806589  ATTAATGAATTTGTCGGAGGTGAAAAAGAGACAAACCTCGCATTAGAAGAG;ATATCAGC
        :::::::::::::::::::::::::::: : ::::::::::::::::::: ::::::::
_       ATTAATGAATTTGTCGGAGGTGAAAAAOAOACAAACCTCGCATTAGAAGAGAATATCAGC
            730       740       750       760       770       780

790       800       810       820       830       840
806559  AAATTAAAAAGTGATTTCGATGCTCTTAATACTCACACTTTAGCAAATGGTGGAACGCAA
        :::::::::::::::::::::::::::::: :::::::::::::::::::::::::::::
_       AAATTAAAAAGTGATTTCGATGCTCTTAATATTCACACTTTAGCAAATGGTGGAACGCAA
            790       800       810       820       830       840

850       860       870       880       890       900
806559  GGCAGACATCTGATCACTGATAAACAAATCATTATTTATCAACCAGAGAATCTTAACTCT
        :::::::::::::::::::::::::::::::::::::::::::: ::::::::::::: 
_       GGCAGACATCTGATCACTGATAAACAAATCATTATTTATCAACCAGAGAATCTTAACTCC
            850       860       870       880       890       900

910       920       930       940       950       960
806559  CAAGATAAACAACTATTTGATAATTATGTTATTTTAGGTAATTACACGACATTAATGTTT
        ::: ::::::::::::::::::::::::::::::::::::::::::::::::::::::::
_       CAACATAAACAACTATTTGATAATTATGTTATTTTAGGTAATTACACGACATTAATGTTT
            910       920       930       940       950       960
```

```
               970       980       990      1000      1010      1020
806559 AATATTAGCCGTGCTTATGTGCTGGAAAAAGATCCCACACAAAAGGCGCAACTAAAGCAG
       ::::::::::::::::::::::::::::::::::::::::::::::::::::::::::::
     _ AATATTAGCCGTGCTTATGTGCTGGAAAAAGATCCCACACAAAAGGCGCAACTAAAGCAG
               970       980       990      1000      1010      1020

1030      1040      1050      1060      1070      1080
806559 ATGTACTTATTAATGACAAAGCATTTATTAGATCAAGGCTTTGTTAAAGGGAGTGCTTTA
       ::::::::::::::::::::::::::::::::::::::::::::::::::::::::::::
     _ ATGTACTTATTAATGACAAAGCATTTATTAGATCAAGGCTTTGTTAAAGGGAGTGCTTTA
              1030      1040      1050      1060      1070      1080

1090      1100      1110      1120      1130      1140
806559 GTGACAACCCATCACTGGGGATACAGTTCTCGTTGGTGGTATATTTCCACGTTATTAATG
       ::::::::::::::::::::::::::::::::::::::::::::::::::::::::::::
     _ GTGACAACCCATCACTGGGGATACAGTTCTCGTTGGTGGTATATTTCCACGTTATTAATG
              1090      1100      1110      1120      1130      1140

1150      1160      1170      1180      1190      1200
806559 TCTGATGCACTAAAAGAAGCGAACCTACAAACTCAAGTTTATGATTCATTACTGTGGTAT
       ::::::::::::::::::::::::::::::::::::::::::::::::::::::::::::
     _ TCTGATGCACTAAAAGAAGCGAACCTACAAACTCAAGTTTATGATTCATTACTGTGGTAT
              1150      1160      1170      1180      1190      1200

1210      1220      1230      1240      1250      1260
806559 TCACGTGAGTTTAAAAGTAGTTTTGATATGAAAGTAAGTGCTGATAGCTCTGATCTAGAT
       ::::::::::::::::::::::::::::::::::::::::::::::::::::::::::::
     _ TCACGTGAGTTTAAAAGTAGTTTTGATATGAAAGTAAGTGCTGATAGCTCTGATCTAGAT
              1210      1220      1230      1240      1250      1260

1270      1280      1290      1300      1310      1320
806559 TATTTCAATACCTTATCTCGCCAACATTTAGCCTTATTACTACTAGAGCCTGATGATCAA
       ::::::::::::::::::::::::::::::::::::::::::::::::::::::::::::
     _ TATTTCAATACCTTATCTCGCCAACATTTAGCCTTATTATTACTAGAGCCTGATGATCAA
              1270      1280      1290      1300      1310      1320

1330      1340      1350      1360      1370      1380
806859 AAGCGTATCAACTTAGTTAATACTTTCAGCCATTATATCACTGGCGCATTAACGCAAGTG
       ::::::::::::::::::::::::::::::::::::::::::::::::::::::::::::
     _ AAGCGTATCAACTTAGTTAATACTTTCAGCCATTATATCACTGGCGCATTAACGCAAGTG
              1330      1340      1350      1360      1370      1380

1390      1400      1410      1420      1430      1440
806559 CCACCGGGTGGTAAAGATGGTTTACGCCCTGATGGTACAGCATGGCGACATGAAGGCAAC
       ::::::::::::::::::::::::::::::::::::::::::::::::::::::::::::
     _ CCACCGGGTGGTAAAGATGGTTTACGCCCTGATGGTACAGCATGGCGACATGAAGGCAAC
              1390      1400      1410      1420      1430      1440

1450      1460      1470      1480      1490      1500
806559 TATCCGGGCTACTCTTTCCCAGCCTTTAAAAATGCCTCTCAGCTTATTTATTTATTACGC
       ::::::::::::::::::::::::::::::::::::::::::::::::::::::::::::
     _ TATCCGGGCTACTCTTTCCCAGCCTTTAAAAATGCCTCTCAGCTTATTTATTTATTACGC
              1450      1460      1470      1480      1490      1500

1510      1520      1530      1540      1550      1560
806559 GATACACCATTTTCAGTGGGTGAAAGTGGTTGGAATAGCCTGAAAAAAGCGATGGTTTCA
       ::::::::::::::::::::::::::::::::::::::::::::::::::::::::::::
     _ GATACACCATTTTCAGTGGGTGAAAGTGGTTGGAATAACCTGAAAAAAGCGATGGTTTCA
              1510      1520      1530      1540      1550      1560

1570      1580      1590      1600      1610      1620
806559 GCGTGGATCTACAGTAATCCAGAAGTTGGATTACCGCTTGCAGGAAGACACCCTCTTAAC
       ::::::::::::::::::::::::::::::::::::::::::::::::::::::::::::
     _ GCGTGGATCTACAGTAATCCAGAAGTTGGATTACCGCTTGCAGGAAGACACCCTTTTAAC
              1570      1580      1590      1600      1610      1620

1630      1640      1650      1660      1670      1680
806559 TCACCTTCGTTAAAATCAGTCGCTCAAGGCTATTACTGGCTTGCCATGTCTGCAAAATCA
       ::::::::::::::::::::::::::::::::::::::::::::::::::::::::::::
     _ TCACCTTCGTTAAAATCAGTCGCTCAAGGCTATTACTGGCTTGCCATGTCTGCAAAATCA
              1630      1640      1650      1660      1670      1680

1690      1700      1710      1720      1730      1740
806559 TCGCCTGATAAAACACTTGCATCTATTTATCTTGCGATTAGTGATAAAACACAAAATGAA
       ::::::::::::::::::::::::::::::::::::::::::::::::::::::::::::
     _ TCGCCTGATAAAACACTTGCATCTATTTATCTTGCGATTAGTGATAAAACACAAAATGAA
              1690      1700      1710      1720      1730      1740

1750      1760      1770      1780      1790      1800
806559 TCAACTGCTATTTTTGGAGAAACTATTACACCAGCGTCTTTACCTCAAGGTTTCTATGCC
       ::::::::::::::::::::::::::::::::::::::::::::::::::::::::::::
```

-continued

```
        TCAACTGCTATTTTTGGAGAAACTATTACACCAGCGTCTTTACCTCAAGGTTTCTATGCC
          1750      1760      1770      1780      1790      1800

1810      1820      1830      1840      1850      1860
806559  TTTAATGGCGGTGCTTTTGGTATTCATCGTTGGCAAGATAAAATGGTGACACTGAAAGCT
        ::::::::::::::::::::::::::::::::::::::::::::::::::::::::::::
        TTTAATGGCGGTGCTTTTGGTATTCATCGTTGGCAAGATAAAATGGTGACACTGAAAGCT
          1810      1820      1830      1840      1850      1860

1570      1880      1890      1900      1910      1920
806559  TATAACACCAATGTTTGGTCATCTGAAATTrATAACAAAGATAACCGTTATGGCCGTTAC
        ::::::::::::::::::::::::::::::: ::::::::::::::::::::::::::::
        TATAACACCAATGTTTGGTCATCTGAAATTTATAACAAAGATAACCGTTATGGCCGTTAC
          1570      1880      1890      1900      1910      1920

1930      1940      1950      1960      1970      1980
808559  CAAAGTCATGGTGTCGCTCAAATAGTGAGTAATGGCTCGCAGCTTTCACAGGGCTATCAG
        ::::::::::: ::::::::::::::::::::::::::::::::::::::::::::::::
        CAAAGTCATGCTGTCGCTCAAATAGTGAGTAATGGCTCGCAGCTTTCACAGGGCTATCAG
          1930      1940      1950      1960      1970      1980

1990      2000      2010      2020      2030      2040
806959  CAAGAAGGTTGGGATTGGAATAGAATGCCAGGGGCAACCACTATCCACCTTCCTCTTAAA
        :::::::::::::::::::::::::::::  :::::::::::::: :: :::::::::::
        CAAGAAGGTTGGGATTGGAATAGAATGCAAGGGGCAACCACTATTCACCTTCCTCTTAAA
          1990      2000      2010      2020      2030      2040

2050      2060      2070      2090      2090      2100
806555  GACTTAGACAGTCCTAAACCTCATACCTTAATGCAACGTGGAGAGCGTGGATTTAGCGGA
        ::::::::::::::::::::::::::::::::::::::::::::::::::::::::::::
        GACTTAGACAGTCCTAAACCTCATACCTTAATGCAACGTGGAGAGCGTGGATTTAGCGGA
          2050      2060      2070      2090      2090      2100

2110      2120      2130      2140      2150      2160
806599  ACATCATCCCTTGAAGGTCAATATGGCATGATGGCATTCGATCTTATTTATCCCGCCAAT
        :::::::::::::::  :::::::::::::::::::::::::::::::::::::::::::
        ACATCATCCCTTGAACGTCAATATGGCATGATGGCATTCGATCTTATTTATCCCGCCAAT
          2110      2120      2130      2140      2150      2160

2170      2180      2190      2200      2210      2220
805559  CTTGAGCGTTTTGATCCTAATTTCACTGCGAAAAAGAGTGTATTAGCCGCTGATAATCAC
        ::::::::::::::::::::::::::::::::::::::::::::::::::::::::::::
        CTTGAGCGTTTTGATCCTAATTTCACTGCGAAAAAGAGTGTATTAGCCGCTGATAATCAC
          2170      2180      2190      2200      2210      2220

2230      2240      2250      2260      2270      2280
806559  TTAATTTTTATTGGTAGCAATATAAATAGTAGTGATAAAAATAAAAATGTTGAAACGACC
        ::::::::::::::::::::::::::::::::::::::::::::::::::::::::::::
        TTAATTTTTATTGGTAGCAATATAAATAGTAGTGATAAAAATAAAAATGTTGAAACGACC
          2230      2240      2250      2260      2270      2280

2290      2300      2310      2320      2330      2340
806555  TTATTCCAACATGCCATTACTCCAACATTAAATACCCTTTGGATTAATGGACAAAACATA
        :::::::::::::::::::::::::::::::::::::::::::::::::::::::::: :
        TTATTCCAACATGCCATTACTCCAACATTAAATACCCTTTGGATTAATGGACAAAAGATA
          2290      2300      2310      2320      2330      2340

2350      2360      2370      2380      2390      2400
806559  CAAACATGCCTTATCAAACAACACTTCAACAAGGTGATTGGTTAATTGATAGCAATGGC
         ::::::::::::::::::::::::::::::::::::::::::::::::::::::::::
        GAAACATGCCTTATCAAACAACACTTCAACAAGGTGATTGGTTAATTGATAGCAATGGC
          2350      2360      2370      2380      2390      2400

2410      2420      2430      2440      2450      2460
806559  AATGGTTACTTAATTACTCAAGCAGAAAAAGTAAATGTAAGTCGCCAACATCAGGTTTCA
        ::::::::::::::::::::::::::::::::::::::::::::::::::::::::::::
        AATGGTTACTTAATTACTCAAGCAGAAAAAGTAAATGTAAGTCGCCAACATCAGGTTTCA
          2410      2420      2430      2440      2450      2460

2470      2480      2490      2500      2510      2520
806559  GCGGAAAATAAAAATCGCCAACCGACAGAAGGAAACTTTAGCTCGCCATGGATCGATCAC
        ::::::::::::::::::::::::::::::::::::::::::::::::::::::::::::
        GCGGAAAATAAAAATCGCCAACCGACAGAAGGAAACTTTAGCTCGGCATGGATCGATCAC
          2470      2480      2490      2500      2510      2520

2530      2540      2550      2860      2570      2580
808559  AGCACTCGCCCCAAAGATGCCAGTTATGAGTATATGGTCTTTTTAGATGCGACACCTGAA
        ::::::::::::::::::::::::::::::::::::::::::::::::::::::::::::
        AGCACTCGCCCCAAAGATGCCAGTTATGAGTATATGGTCTTTTTAGATGCGACACCTGAA
          2530      2540      2550      2860      2570      2580
```

```
                 2590      2600      2610      2620      2630      2640
806559 AAAATGCGAGAGATGGCACAAAAATTCCGTGAAAATAATGGGTTATATCAGGTTCTTCGT
       ::::::::::::::::::::::::::::::::::::::::::::::::::::::::::::
     _ AAAATGGGAGAGATGGCACAAAAATTCCGTGAAAATAATGGGTTATATCAGGTTCTTCGT
                 2590      2600      2610      2620      2630      2640

2650      2660      2670      2680      2690      2700
806559 AAGGATAAAGACGTTCATATTATTCTCGATAAACTCAGCAATGTAACGGGATATGCCTTT
       ::::::::::::::::::::::::::::::::::::::::::::::::::::::::::::
     _ AAGGATAAAGACGTTCATATTATTCTCGATAAACTCAGCAATGTAACGGGATATGCCTTT
                 2650      2660      2670      2680      2690      2700

2710      2720      2730      2740      2750      2760
806559 TATCAGCCAGCATCAATTGAAGACAAATGGATCAAAAAGGTTAATAAACCTGCAATTGTG
       ::::::::::::::::::::::::::::::::::::::::::::::::::::::::::::
     _ TATCAGCCAGCATCAATTGAAGACAAATGGATCAAAAAGGTTAATAAACCTGCAATTGTG
                 2710      2720      2730      2740      2750      2760

2770      2780      2790      2800      2810      2820
806559 ATGACTCATCGACAAAAAGACACTCTTATTGTCAGTGCAGTTACACCTGATTTAAATATG
       ::::::::::::::::::::::::::::::::::::::::::::::::::::::::::::
     _ ATGACTCATCGACAAAAAGACACTCTTATTGTCAGTGCAGTTACACCTGATTTAAATATG
                 2770      2780      2790      2800      2810      2820

2830      2840      2850      2860      2870      2880
806559 ACTCGCCAAAAAGCAGCAACTCCTGTCACCATCAATGTCACGATTAATGGCAAATGGCAA
       ::::::::::::::::::::::::::::::::::::::::::::::::::::::::::::
     _ ACTCGCCAAAAAGCAGCAACTCCTGTGACCATCAATGTCACGATTAATGGCAAATGGCAA
                 2830      2840      2850      2860      2870      2880

2890      2900      2910      2920      2930      2940
806559 TCTGCTGATAAAAATAGTGAAGTGAAATATCAGGTTTCTGGTGATAACACTGAACTGACG
       ::::::::::::::::::::::::::::::::::::::::::::::::::::::::::::
     _ TCTGCTGATAAAAATAGTGAAGTGAAATATCAGGTTTCTGGTGATAACACTGAACTGACG
                 2890      2900      2910      2920      2930      2940

2950      2960      2970      2980      2990
806559 TTTACGAGTTACTTTGGTATTCCACAAGAAATCAAACTCTCGCCACTCCCTTGA
       ::::::::::::::::::::::::::::::::::::::::::::::::::::::
     _ TTTACGAGTTACTTTGGTATTCCACAAGAAATCAAACTCTCGCCACTCCCTTGA
                 2950      2960      2970      2980      2990
```

The sequence identity at the amino acid level is shown below:

```
SEQ ID NO: 29 Present Invention Chondroitinase ABC I protein
>_ ASCI Present invention 997 aa vs.
>_ ABCI mature 997 aa
scoring matrix: gap penalties: -12/-2
99.5% identity; Global alignment score: 6595
              10        20        30        40        50        60
365019 ATSNPAFDPKNLMQSEIYHFAQNNPLADFSSDKNSILTLSDKRSIMGNQSLLWKWKGGSS
       ::::::::::::::::::::::::::::::::::::::::::::::::::::::::::::
     _ ATSNPAFDPKNLMQSEIYHFAQNNPLADFSSDKNSILTLSDKRSIMGNQSLLWKWKGGSS
              10        20        30        40        50        60

70        80        90       100       110       120
365019 FTLHKKLIVPTDKEASKAWGRSSTPVFSFWLYNEKPIDGYLTIDFGEKLISTSEAQAGFK
       ::::::::::::::::::::::::::::::::::::::::::::::::::::::::::::
     _ FTLHKKLIVPTDKEASKAWGRSSTPVFSPWLYNEKPIDGYLTIDFGEKLISTSEAQAGFK
              70        80        90       100       110       120

130       140       150       160       170       180
365019 VKLDFTGWRTVGVSLNNDLENREMTLNATNTSSDGTQDSIGRSLGAKVDSIRFKAPSNVS
       ::::::::::::::::::::::::::::::::::::::::::::::::::::::::::::
     _ VKLDFTGWRAVGVSLNNDLENREMTLNATNTSSDGTQDSIGRSLGAKVDSIRFKAPSNVS
             130       140       150       160       170       180

190       200       210       220       230       240
365019 QGEIYIDRIMFSVDDARYQWSDYQVKTRLSEPEIQFHNVKPQLPVTPENLAAIDLIRQRL
       ::::::::::::::::::::::::::::::::::::::::::::::::::::::::::::
     _ QGEIYIDRIMFSVDDARYQWSDYQVKTRLSEPEIQFHNVKPQLPVTPENLAAIDLIRQRL
             190       200       210       220       230       240

250       260       270       280       290       300
365019 INEFVGGEKETNLALEENISKLKSDFDALNTHTLANGGTQGRHLITDKQIIIYGPENLNS
       ::::::::::::::::::::::::::::::::::::::::::::::::::::::::::::
     _ INEFVGGEKETNLALEENISKLKSDFDALNIHTLANGGTQGRHLITDKQIIIYQPENLNS
             250       260       270       280       290       300

310       320       330       340       350       360
```

```
365019  QDKQLFDNYVILGNYTTLMFNISRAYVLEKDPTQKAQLKQMYLLMTKHLLDQGFVKGSAL
        ::::::::::::::::: ::::::::::::::::::::::::::::::::::::::::
    _   QDKQLFDNYVILGNYTTLMENISRAYVLEKDPTQKAQLKQMYLLMTKHLLDQGFVKGSAL
           310       320       330       340       350       360

370       380       390       400       410       420
365019  VTTHHWGYSSRWWYISTLLMSDALKEANLQTQVYDSLLWYSREFKSSFDMKVSADSSDLD
        ::::::::::: ::::::::::::::::::::::::::::::::::::::::::::::::
    _   VTTHHWGYSSRWWYISTLLMSDALKEANLQTQVYDSLLWYSREFKSSFDMKVSADSSDLD
           370       380       390       400       410       420

430       440       450       460       470       480
365019  YFNTLSRQHLALLLLEPDDQKRINLVNTFSHYITGALTQVPPGGKDGLRPDGTAWRHEGN
        ::::::::::::::::::: ::::::::::::::::::::::::::::::::::::::::
    _   YFNTLSRQHLALLLLEPODQKRINLVNTFSHYITGALTQVPPGGKDGLRPDGTAWRHEGN
           430       440       450       460       470       480

490       500       510       520       530       540
365019  YPGYSFPAFKNASQLIYLLRDTPFSVGESGWNSLKKAMVSAWIYSNPEVGLPLAGRHPLN
        :::::::::::::::::::::::::::::::: ::::::::::::::::::::::::: :
    _   YPGYSFPAFKNASQLIYLLRDTPFSVGESGWNNLKKAMVSAWIYSNPEVGLPLAGRHPFN
           490       500       510       520       530       540

550       560       570       580       590       600
365019  SPSLKSVAQGYYWLAMSAKSSPDKTLASIYLAISDKTQNESTAIFGETITPASLPQGFYA
        :::::::::::::::::::::::::::::::::::::::::::::::::::::::::::
    _   SPSLKSVAQGYYWLAMSAKSSPDKTLASIYLAISDKTQNESTAIFGETITPASLPQGFYA
           550       560       570       580       590       600

610       620       630       640       650       660
365019  FNGGAFGIHRWQDKMVTLKAYNTNVWSSEIYNKDNRYGRYQSHGVAQIVSNGSQLSQGYQ
        ::::::::::::::::::::::::::::::::::::::::::::::::::::: ::::::
    _   FNGGAFGIHRWQDKMVTLKAYNTNVWSSEIYNKDNRYGRYQSHGVAQIVSNGSOLSQGYQ
           610       620       630       640       650       660

670       680       690       700       710       720
365019  QEGWDWNRMPGATTIHLPLKDLDSPKPHTLMQRGERGFSGTSSLEGQYGMMAFDLIYPAN
        ::::::::: ::::::::::::::::::::::::::::::::::::::::::::::::::
    _   QEGWDWNRMQGATTIHLPLKDLDSPKPHTLMQRGERGFSGTSSLEGQYGMMAFDLIYPAN
           670       680       690       700       710       720

730       740       750       760       770       780
365019  LERFDPNFTAKKSVLAADNHLIFIGSNINSSDKNKNVETTLFQHAITPTLNTLWINGQKI
        ::::::::::::::::::::::::::::::::::::::::::::::::::::::::::::
    _   LERFDPNFTAKKSVLAADNHLIFIGSNINSSDKNKNVETTLFQHAITPTLNTLWINGQKI
           730       740       750       760       770       780

790       800       810       820       830       840
365019  ENMPYQTTLQQGDWLIDSNGNGYLITQAEKVNVSRQHQVSAENKNRQPTEGNFSSAWIDH
        ::::::::::::::::::::::::::::::::::::::::::::::::::::::::::::
    _   ENMPYQTTLQQGDWLIDSNGNGYLITQAEKVNVSRQHQVSAENKNRQPTEGNFSSAWIDH
           790       800       810       820       830       840

850       860       870       880       890       900
365019  STRPKDASYEYMVFLDATPEKMGEMAQKFRENNGLYQVLRKDKDVHIILDKLSNVTGYAF
        ::::::::::::::::::::::::::::::::::::::::::::::::::::::::::::
    _   STRPKDASYEYMVFLDATPEKMGEMAQKFRENNGLYQVLRKDKDVHIILDKLSNVTGYAF
           850       860       870       880       890       900

910       920       930       940       950       960
365019  YQPASIEDKWIKKVNKPAIVMTHRQKDTLIVSAVTPDLNMTRQKAATPVTINVTINGKWQ
        ::::::::::::::::::::::::::::::::::::::::::::::::::::::::::::
    _   YQPASIEDKWIKKVNKPAIVMTHRQKDTLIVSAVTPDLNMTRQKAATPVTINVTINGKWQ
           910       920       930       940       950       960

970       980       990
365019  SADKNSEVKYQVSGONTELTFTSYFGIPQEIKLSPLP
        ::::::::::::::: :::::::::::::::::::::
    _   SADKNSEVKYQVSGDNTELTFTSYFGIPQEIKLSPLP
           970       980       990
```

REFERENCES

1. Fethiere J, Eggimann B, Cygler M (1999) Crystal structure of chondroitin AC lyase, a representative of a family of glycosaminoglycan degrading enzymes. J. Mol. Biol. 288: 635-47.

2. Pojasek K, Shriver Z, Kiley, P Venkataraman G and Sasisekharan R. (2001) Biochem Biophys Res Commun. 286:343-51.

3. Huang W, Matte A, Li Y, Kim Y S, Linhardt R J, Su H, Cygler M. (1999) Crystal structure of chondroitinase B from *Flavobacterium heparinum* and its complex with a disaccharide product at 1.7 A resolution. J. Mol. Biol. 294:1257-69.
4. Miura R O, Yamagata S, Miura Y, Harada T and Yamagata T. (1995) Anal Biochem. 225:333-40.
5. Yamagata T, Saito H, Habuchi O and Suzuki S. (1968) J. Biol. Chem. 243:1536-42.

Although the present invention has been described in considerable detail with reference to certain preferred embodiments thereof, other versions are possible. Therefore the spirit and scope of the appended claims should not be limited to the description and the preferred versions contain within this specification.

What is claimed:

1. A method of treating a tissue, the method comprising: administering a mutant proteoglycan degrading polypeptide composition to the tissue, wherein the polypeptide is selected from the group consisting of SEQ ID NO: 2, SEQ ID NO: 3, and SEQ ID NO: 4.

2. The method of claim 1, wherein the tissue is from the CNS.

3. The method of claim 1, further comprising the act of identifying tissue from a contusive spinal cord injury.

4. The method of claim 1, wherein the composition promotes neurite regeneration.

5. The method of claim 1, wherein the composition further includes molecules which block the action of neurite growth inhibitors, molecules which promote neurite adhesion, diagnostic molecules or a combination of these.

6. The method of claim 1, wherein the plasticity of the nervous system is improved.

7. The method of claim 1, wherein the mutant proteoglycan degrading polypeptide degrades a proteoglycan in a tissue of the central nervous system.

8. The method of claim 7, wherein the proteoglycan degradation promotes diffusion of molecules into the tissue.

9. The method of claim 1, wherein the composition includes cells.

10. The method of claim 1, wherein the composition comprises a pharmaceutically acceptable excipient.

11. A method of treating a tissue, the method comprising: administering a mutant proteoglycan degrading polypeptide composition to the tissue, wherein the proteoglycan degrading polypeptide is SEQ ID NO: 2.

12. The method of claim 11, wherein the mutant proteoglycan degrading polypeptide degrades a proteoglycan in a tissue of the central nervous system.

13. The method of claim 12, wherein the proteoglycan degradation promotes diffusion of molecules into the tissue.

14. The method of claim 11, wherein the composition includes cells.

15. The method of claim 11, wherein the composition comprises a pharmaceutically acceptable excipient.

16. The method of claim 11, wherein the composition includes molecules that block the action of neurite growth inhibitors, molecules which promote neurite adhesion, diagnostic molecules or a combination of any thereof.

17. The method of claim 11, wherein the composition promotes neurite regeneration.

18. The method of claim 11, wherein the plasticity of the nervous system is improved.

19. A method of treating a tissue, the method comprising: administering a mutant proteoglycan degrading polypeptide composition to the tissue, wherein the proteoglycan degrading polypeptide is SEQ ID NO: 3.

20. The method of claim 19, wherein the mutant proteoglycan degrading polypeptide degrades a proteoglycan in a tissue of the central nervous system.

21. The method of claim 20, wherein the proteoglycan degradation promotes diffusion of molecules into the tissue.

22. The method of claim 19, wherein the composition includes cells.

23. The method of claim 19, wherein the composition comprises a pharmaceutically acceptable excipient.

24. The method of claim 19, wherein the composition includes molecules that block the action of neurite growth inhibitors, molecules which promote neurite adhesion, diagnostic molecules or a combination of any thereof.

25. The method of claim 19, wherein the composition promotes neurite regeneration.

26. The method of claim 19, wherein the plasticity of the nervous system is improved.

27. A method of treating a tissue, the method comprising: administering a mutant proteoglycan degrading polypeptide composition to the tissue, wherein the proteoglycan degrading polypeptide is SEQ ID NO: 4.

28. The method of claim 27, wherein the mutant proteoglycan degrading polypeptide degrades a proteoglycan in a tissue of the central nervous system.

29. The method of claim 28, wherein the proteoglycan degradation promotes diffusion of molecules into the tissue.

30. The method of claim 27, wherein the composition includes cells.

31. The method of claim 27, wherein the composition comprises a pharmaceutically acceptable excipient.

32. The method of claim 27, wherein the composition includes molecules that block the action of neurite growth inhibitors, molecules which promote neurite adhesion, diagnostic molecules or a combination of any thereof.

33. The method of claim 27, wherein the composition promotes neurite regeneration.

34. The method of claim 27, wherein the plasticity of the nervous system is improved.

* * * * *